US008609413B2

(12) United States Patent
Suter et al.

(10) Patent No.: US 8,609,413 B2
(45) Date of Patent: Dec. 17, 2013

(54) NEURONS, ASTROCYTES AND OLIGODENDROCYTES DIFFERENTIATED FROM A MAMMALIAN PLURIPOTENT OR NEURAL STEM CELLS EXPOSED TO A PYRIDINE DERIVIATIVE

(75) Inventors: David M. Suter, Geneva (CH); Olivier Preynat-Seauve, Habare-Lullin (FR); Karl-Heinz Krause, Geneva (CH)

(73) Assignee: Research Development Foundation, Carson CIty, NV (US)

( * ) Notice: Subject to any disclaimer, the term of this patent is extended or adjusted under 35 U.S.C. 154(b) by 497 days.

(21) Appl. No.: 12/747,116

(22) PCT Filed: Dec. 11, 2008

(86) PCT No.: PCT/US2008/086430
§ 371 (c)(1),
(2), (4) Date: Sep. 29, 2010

(87) PCT Pub. No.: WO2009/076529
PCT Pub. Date: Jun. 18, 2009

(65) Prior Publication Data
US 2011/0046092 A1    Feb. 24, 2011

Related U.S. Application Data

(60) Provisional application No. 61/007,344, filed on Dec. 11, 2007.

(51) Int. Cl.
*C12N 5/00* (2006.01)

(52) U.S. Cl.
USPC .......................................... 435/377; 435/383

(58) Field of Classification Search
None
See application file for complete search history.

(56) References Cited

U.S. PATENT DOCUMENTS

| 5,843,780 A | 12/1998 | Thomson | 435/363 |
| 6,200,806 B1 | 3/2001 | Thomson | 435/366 |
| 7,029,913 B2 | 4/2006 | Thomson | 435/363 |
| 2007/0049576 A1 | 3/2007 | Barlow et al. | 514/214.03 |
| 2007/0078083 A1 | 4/2007 | Barlow et al. | 514/9 |
| 2007/0112017 A1 | 5/2007 | Barlow et al. | 514/282 |

FOREIGN PATENT DOCUMENTS

| EP | 1529838 | 5/2005 |
| EP | 1970446 | 9/2008 |
| WO | WO 2007/025177 | 3/2007 |
| WO | WO 2007/030697 | 3/2007 |
| WO | WO 2007/047978 | 4/2007 |
| WO | WO 2007/053596 | 5/2007 |

OTHER PUBLICATIONS

Ikeuchi et al. MS-430, A Synthetic Pyrimidine Derivative, Influences the Intracellular Signal Transduction Pathway Leading to Neuronal Differentiation of PC12h Cells Journal of Biochemistry, 1998, vol. 123, pp. 423-430.*
Castren et al. Altered differentiation of neural stem cells in fragile X syndrome PNAS, 2005, vol. 102, pp. 17834-17839.*
Smukler et al. Embryonic stem cells assume a primitive neural stem cell fate in the absence of extrinsic influences. J. Cell Biology, Jan. 2006, vol. 172, pp. 79-90.*
Cappuccio et al. Endogenous activation of mGlu5 metabotropic glutamate receptors supports self-renewal of cultured mouse embryonic stem cells. Neuropharmacology, 2005, vol. 49, pp. 196-205.*
Pau et al. Derivation and characterization of monkey embryonic stem cells. Reproductive Biol. Endocrinol., 2004, vol. 2, pp. 41-51.*
Reubinoff et al. Neural progenitors from human embryonic stem cells. Nature Biotechnology, 2001, vol. 19, 1134-1140.*
Barberi et al., "Neural subtype specification of fertilization and nuclear transfer embryonic stem cells and application in parkinsonian mice," *Nat. Biotechnol.*, 21(10):1200-1207, 2003.
Bayatti et al., "A Molecular Neuroanatomical Study of the Developing Human Neocortex from 8 to 17 Postconceptional Weeks Revealing the Early Differentiation of the Subplate and Subventricular Zone," *Cereb. Cortex*, 18(7):1536-1548, 2007.
Bruno et al., "Selective blockade of metabotropic glutamate receptor subtype 5 is neuroprotective," *Neuropharmacology*, 28(12):2223-2230, (2000).
Byrne et al., "Producing primate embryonic stem cells by somatic cell nuclear transfer," *Nature*, 450:497-504, 2007.
Cappuccio et al., "Context-dependent regulation of embryonic stem cell differentiation by mGLu5R metabotropic glutamate receptors," *Neuropharmacology*, 51(3):606-611, 2006.
Cappuccio et al., "Endogenous activation of mGlu5 metabotropic glutamate receptors supports self-renewal of cultured mouse embryonic stem cells," *Neuropharmacology*, 49:196-205, 2005.
Chen et al., "Dedifferentiation of Lineage-Committed Cells by a Small Molecule," *J. Am. Chem. Soc.*, 126(2):410-411, 2004.
Chen et al., "Exploring stem cell biology with small molecules," *Molecular Biosystems*, 2(1): 18-24, 2006.
Chen et al., "Reversine increases the plasticity of lineage-committed mammalian cells," *Proc. Natl. Acad. Sci. USA*, 104(25):10482-10487, 2007.
Chen et al., "Self-renewal of embryonic stem cells by a small molecule," *Proc. Natl. Acad. Sci. USA*, 103(46):17266-17271, 2006a.
Cho et al., "Highly efficient and large-scale generation of functional dopamine neurons from human embryonic stem cells," *Proc. Natl. Acad. Sci. USA*, 105:3392-3397, 2008.

(Continued)

*Primary Examiner* — Deborah Crouch
(74) *Attorney, Agent, or Firm* — Parker Highlander PLLC

(57) ABSTRACT

A method of preparing neural precursor cells by exposing pluripotent stem cells or neural stem cells to a differentiation agent. The agent is a pyridine analog, which in preferred embodiments is a phenylethynyl-substituted or phenylazo-substituted pyridine. In other embodiments, a method of enhancing neural precursor cell survival is provided in which the survival is enhanced by exposure to the pyridine analog. In further embodiments, a method of preparing neuronal cells is provided in which pluripotent or neural stem cells exposed to the pyridine analog are then incubated without the pyridine analog, resulting in differentiation into neurons, astrocytes and oligodendrocytes. These methods may be used in toxicological screens, e.g., to evaluate the neurotoxicity of a test compound.

19 Claims, 9 Drawing Sheets

(56) References Cited

OTHER PUBLICATIONS

Desbordes et al., "High-Throughput Screening Assay for the Identification of Compounds Regulating Self-Renewal and Differentiation in Human Embryonic Stem Cells," *Cell Stem Cell*, 2(6):602-612, 2008.

Ding et al., "Synthetic small molecules that control stem cell fate," *Proc. Natl. Acad. Sci. USA*, 100 (13): 7632-76337, 2003.

Doetsch et al., "Subventricular Zone Astrocytes Are Neural Stem Cells in the Adult Mammalian Brain," *Cell*, 97:703-716, 1999.

Elkabetz et al., "Human ES cell-derived neural rosettes reveal a functionally distinct early neural stem cell stage," *Genes Dev.*, 22:152-165, 2008.

Gaines, "Phenazopyridine hydrochloride: the use and abuse of an old standby for UTI."*Urol Nurs.*, 24(2):207-209, 2004.

Gustafsson et al., "Hypoxia Requires Notch Signaling to Maintain the Undifferentiated Cell State," *Dev Cell.*, 9:617-628, 2005.

Jaeschke et al., "mGlu5 receptor antagonists and their therapeutic potential," *Expert Opinion on Therapeutic Patents*, 18(2):123-142, 2008.

Joannides et al., "A Scaleable and Defined System for Generating Neural Stem Cells from Human Embryonic Stem Cells" *Stem Cells*, 25:731-737, 2007.

Joannides et al., "Environmental signals regulate lineage choice and temporal maturation of neural stem cells from human embryonic stem cells," *Brain*, 130:1263-1275, 2007.

Lee et al., "Directed Differentiation and Transplantation of Human Embryonic Stem Cell-Derived Motoneurons," *Stem Cells*, 25:1931-1939, 2007.

Lee et al., "Isolation and directed differentiation of neural crest stem cells derived from human embryonic stem cells," *Nat. Biotechnol.*, 25:1468-1475, 2007.

Merkle and Alvarez-Buylla, "Neural stem cells in mammalian development," *Curr. Opin. Cell Biol.*, 18:704-709, 2006.

Metallo et al., "Retinoic Acid and Bone Morphogenetic Protein Signaling Synergize to Efficiently Direct Epithelial Differentiation of Human Embryonic Stem Cells," *Stem Cells*, 26(2):372-380.

Mo and Zecevic, "Is Pax6 Critical for Neurogenesis in the Human Fetal Brain?," *Cereb Cortex*, 18(6):1455-1465, 2008.

Nat et al., "Neurogenic neuroepithetial and radial glial cells generated from six human embryonic stem cell lines in serum-free suspension and adherent cultures," *Glia.*, 55(4):385-399, 2007.

O'Connor et al., "Alkaline phosphatase-positive colony formation is a sensitive, specific, and quantitative indicator of undifferentiated human embryonic stem cells," *Stem Cells*, 26(5):1109-1116, 2008.

Osafune et al., "Marked differences in differentiation propensity among human embryonic stem cell lines," *Nat. Biotechnol.*, 26:313-315, 2008.

Perrier et al., "Derivation of midbrain dopamine neurons from human embryonic stem cells," *Proc. Natl. Acad. Sci. USA*, 101(34):12543-12125, 2004.

Pruszak et al., "Markers and methods for cell sorting of human embryonic stem cell-derived neural cell populations," *Stem Cells*, 25(9):2257-2268, 2007.

Quinones-Hinojosa et al., "Cellular composition and cytoarchitecture of the adult human subventricular zone: A niche of neural stem cells," *J. Comp. Neurol.*, 494:415-434, 2006.

Sachinidis et al., "Identification of Small Signalling Molecules Promoting Cardiac-Specific Differentiation of Mouse Embryonic Stem Cells," *Cell Physiol. Biochem.*, 18(6):303-314, 2006.

Sarichelou et al., "Metabotropic glutamate receptors regulate differentiation of embryonic stem cells into GABAergic neurons," *Cell Death Differ.*, 15(4): 700-707, 2008.

Sonntag et al., "Enhanced yield of neuroepithelial precursors and midbrain-like dopaminergic neurons from human embryonic stem cells using the bone morphog protein antagonist noggin," *Stem Cells*, 25:411-418, 2007.

Stoppini et al., "A simple method for organotypic cultures of nervous tissue," *J. Neurosci. Methods*, 37(2):173-182, 1991.

Suter et al., "Phenazopyridine induces and synchronizes neuronal differentiation of embryonic stem cells," *J. of Cellular and Molecular Medicine*, 13(9):3517-3527, 2009.

Suter et al., "Rapid generation of stable transgenic embryonic stem cell lines using modular lentivectors," *Stem Cells*, 24(3):615-623, 2006.

Takahashi et al., "Induction of Pluripotent Stem Cells from Adult Human Fibroblasts by Defined Factors," *Cell*, 131:861-872, 2007.

Takahashi et al., "Induction of Pluripotent Stem Cells from Mouse Embryonic and Adult Fibroblast Cultures by Defined Factors," *Cell*, 126(4):663-676, 2006.

Vazin et al., "Assessment of stromal-derived inducing activity in the generation of dopaminergic neurons from human embryonic stem cells," *Stem Cells*, 26:1517-1525, 2008.

Wu et al., "Integrative genomic and functional analyses reveal neuronal subtype differentiation bias in human embryonic stem cell lines," *Proc. Natl. Acad. Sci. USA*, 104:13821-13826, 2007.

Yang et al., "Human embryonic stem cell-derived dopaminergic neurons reverse functional deficit in parkinsonian rats," *Stem Cells*, 26:55-63, 2008.

Yu et al., "Induced Pluripotent Stem Cell Lines Derived from Human Somatic Cells," *Science*, 318: 1917-1920, 2007.

* cited by examiner

FIG. 3
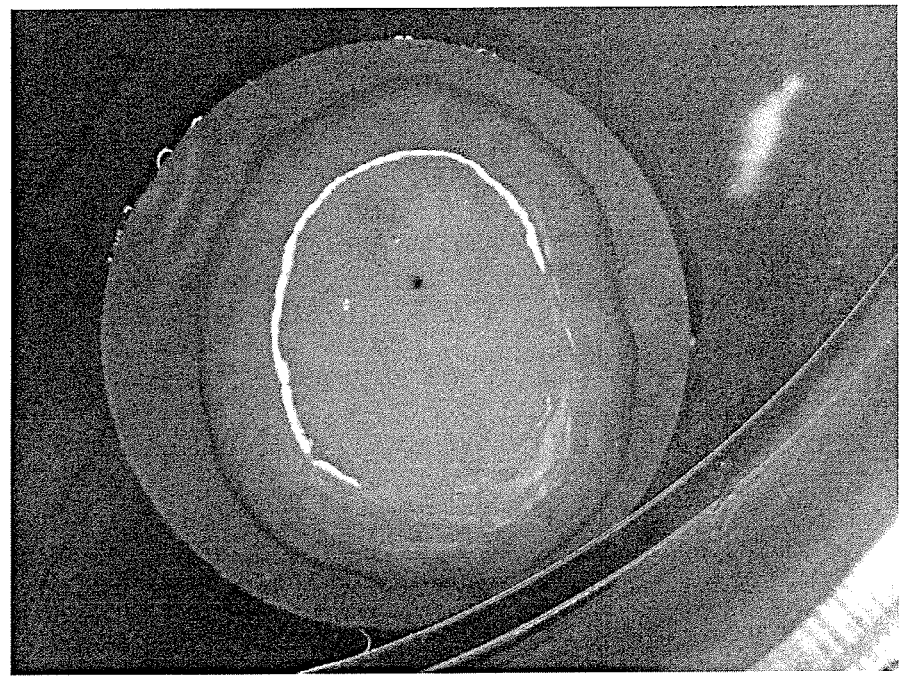
phenazopyridine
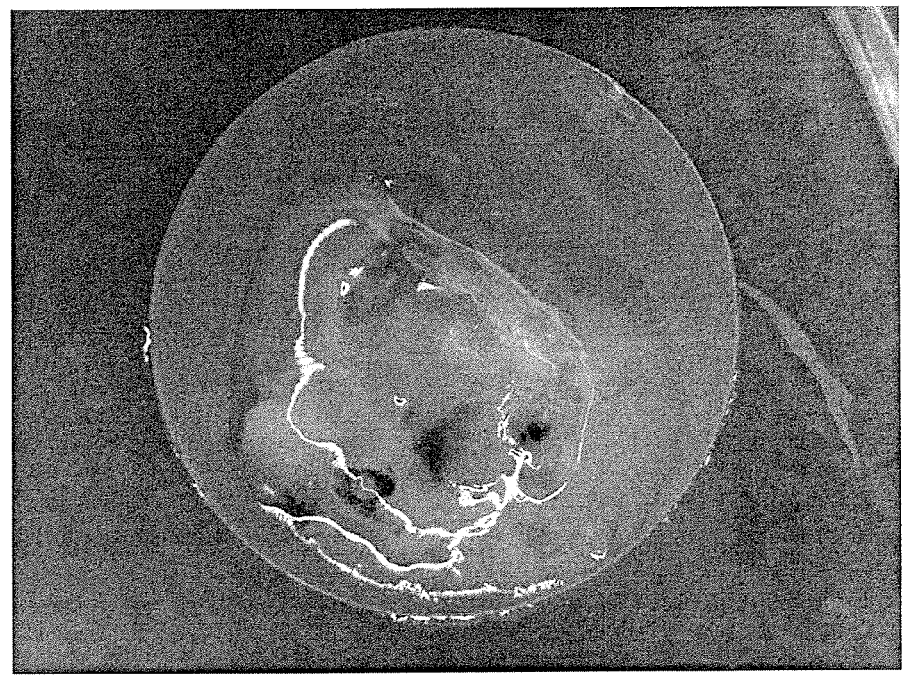
control

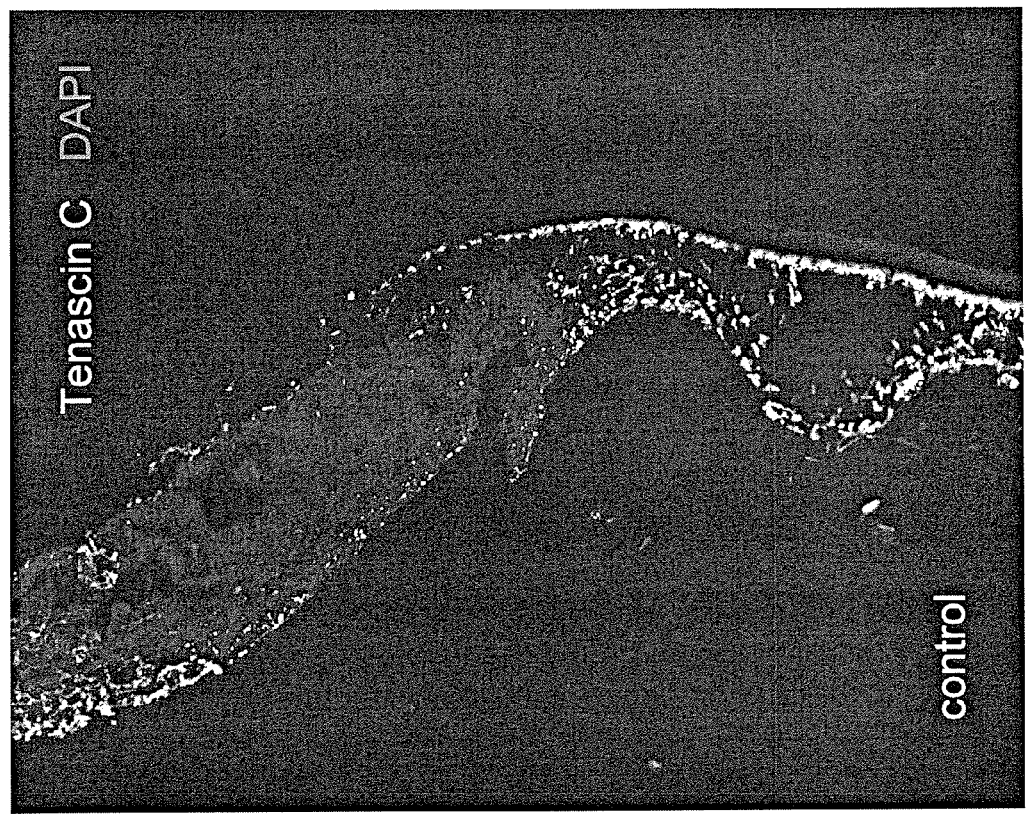
FIG. 4

FIGS. 5A-I
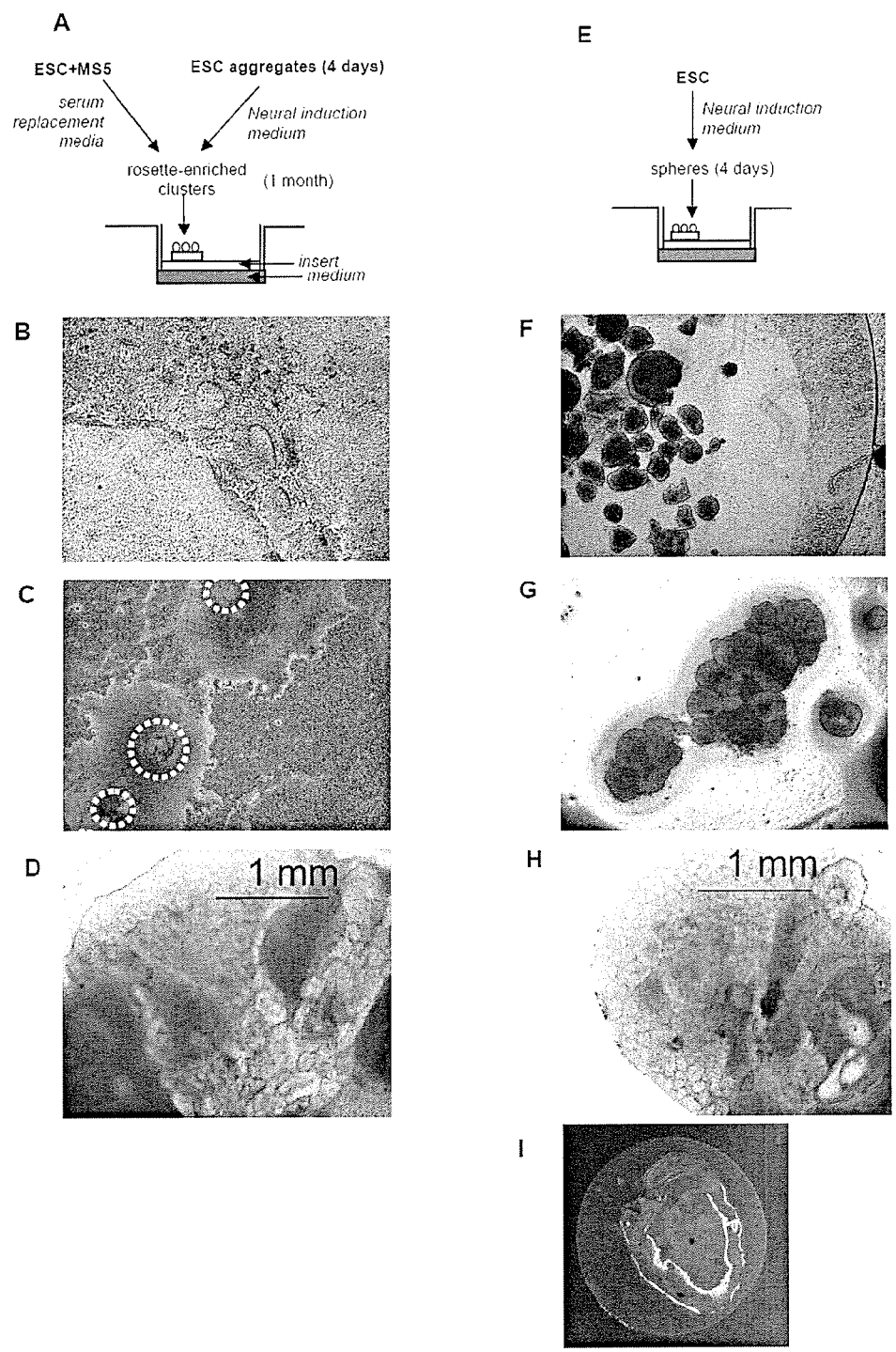

FIGS. 6A-F
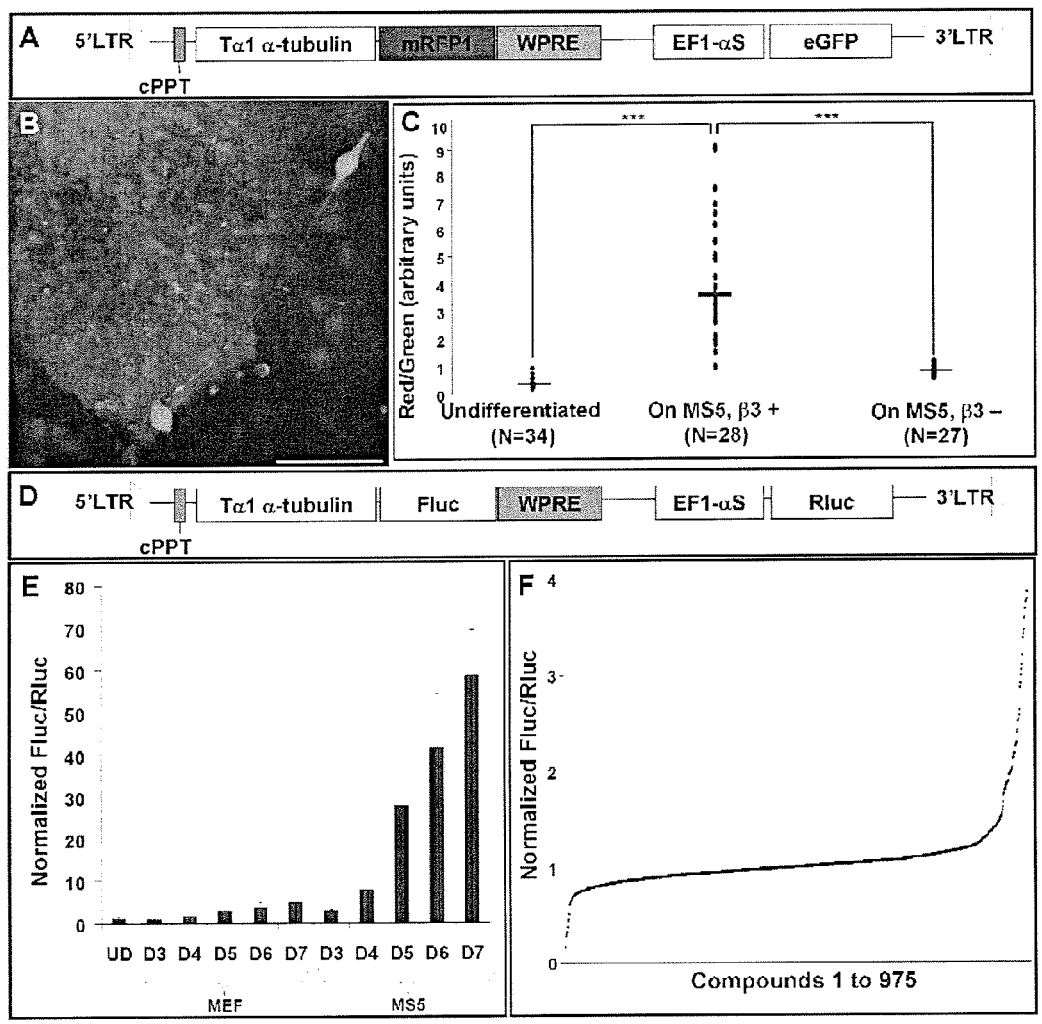

FIGS. 7A-B
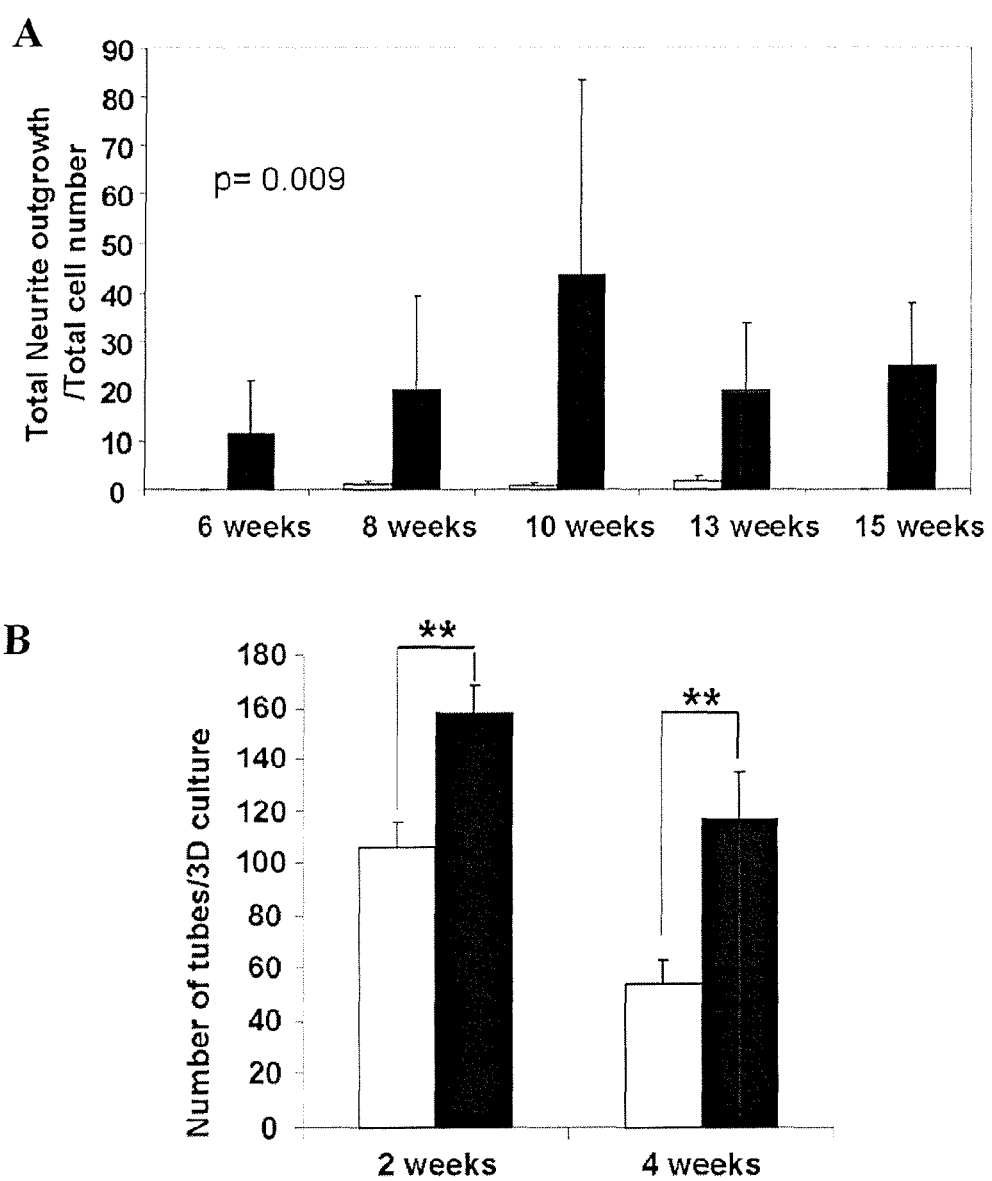

FIGS. 8A-B
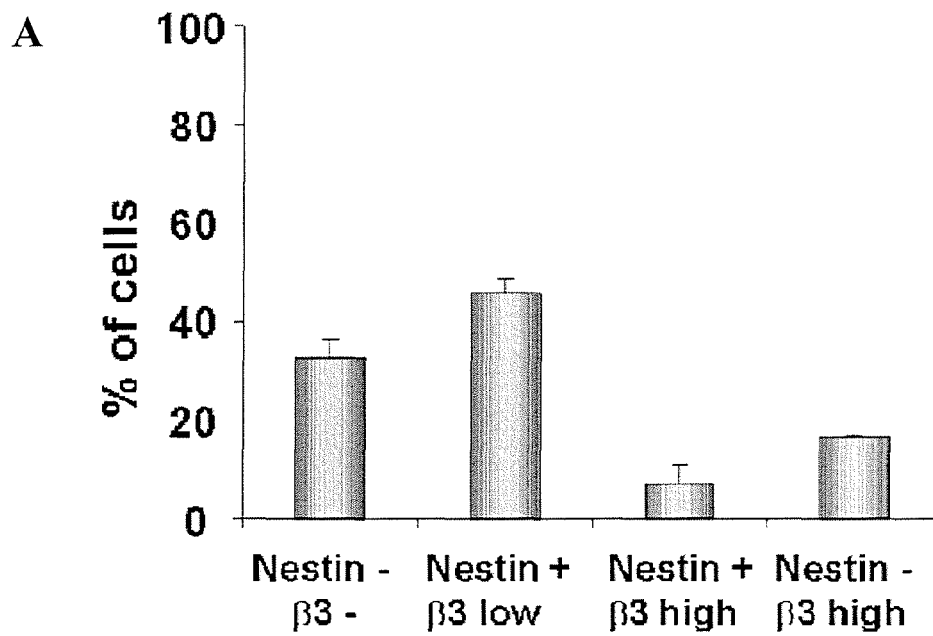
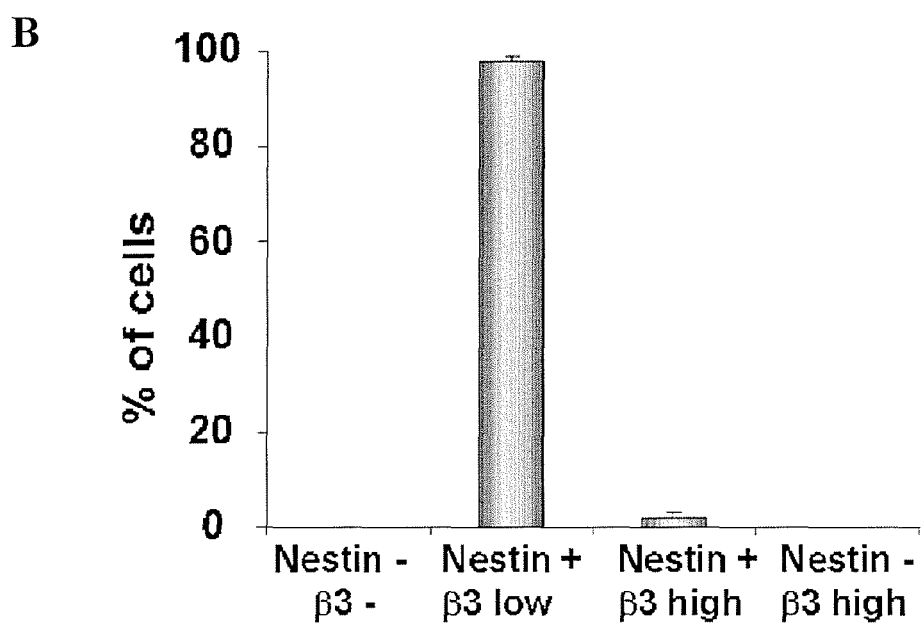

FIGS. 9A-C
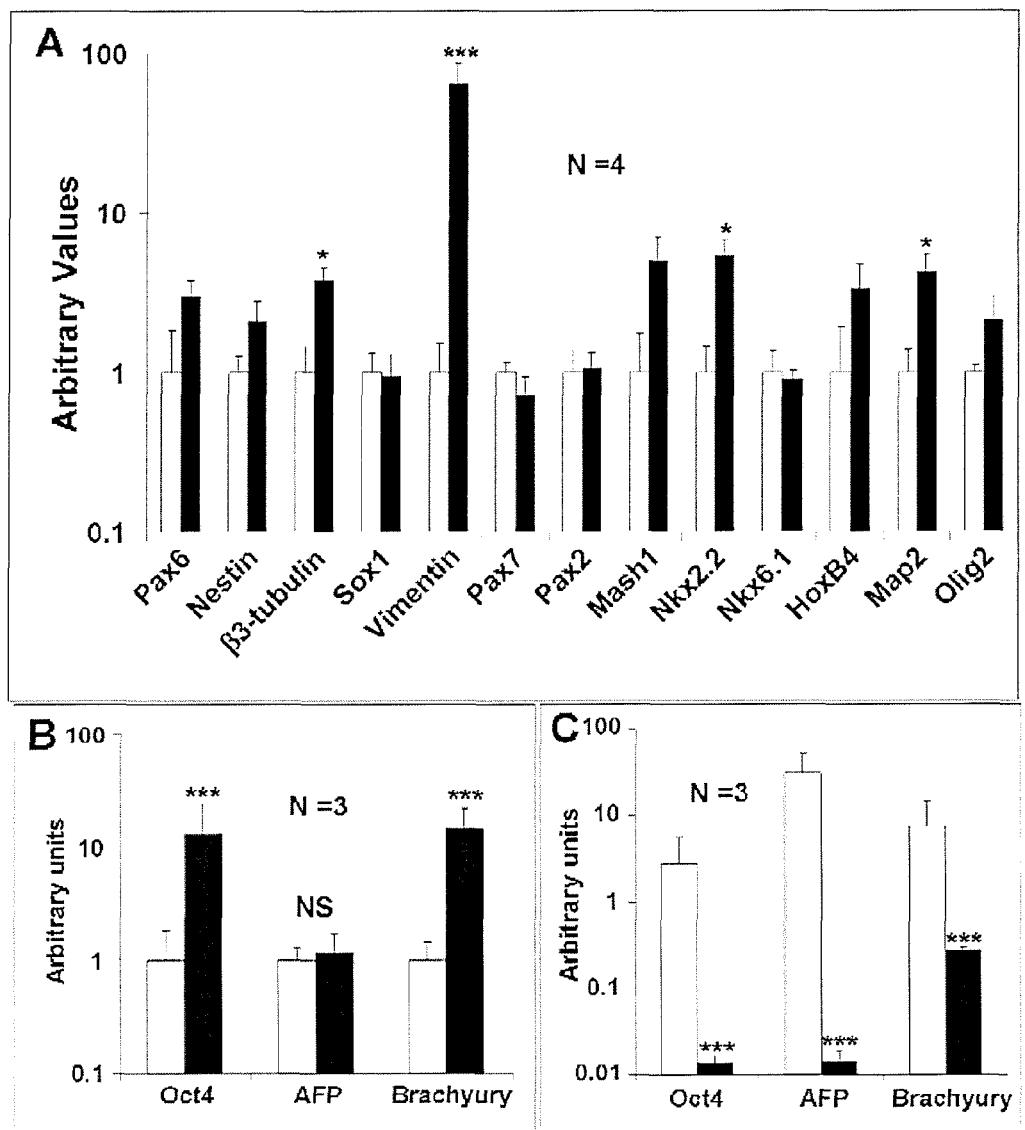

NEURONS, ASTROCYTES AND OLIGODENDROCYTES DIFFERENTIATED FROM A MAMMALIAN PLURIPOTENT OR NEURAL STEM CELLS EXPOSED TO A PYRIDINE DERIVIATIVE

BACKGROUND OF THE INVENTION

This application is a national phase application under 35 U.S.C. §371 of International Application No. PCT/US2008/086430 filed Dec. 11, 2008 which claims priority to U.S. provisional Application No. 61/007,344 filed on Dec. 11, 2007, the entire disclosure of which is specifically incorporated herein by reference in its entirety without disclaimer.

FIELD OF THE INVENTION

This invention generally relates to the field of stem cell development, and in particular to the use of chemical agents to influence the differentiation of pluripotent stem cells and neural stem cells.

RELATED ART

Pluripotent stems cells, including embryonic stem (ES) cells and induced pluripotent stem cells, hold great promise for studying early development and for use in cell therapy. The same is true of adult and embryonic neural stem cells. Because such cells can proliferate in culture and maintain their potential for differentiating into different cell types, they can provide an almost unlimited supply of cells for treating a variety of diseases. A particularly active area of research is the treatment of nervous system diseases using cell therapy. One approach to the treatment of degenerative nervous system diseases is to transplant neural precursor cells into affected areas of the nervous system. Another approach is to stimulate a patient's own neural stem cells to repair the nervous system.

Potential sources of neural precursor cells are cultures of neural precursor cells prepared by differentiating ES cells and other types of stem cells in vitro. Methods of preparing primate ES cell cultures have been described for human, rhesus monkey, and marmoset ES cells. (U.S. Pat. Nos. 5,843,780; 6,200,806; 7,029,913). The methods involve removing the trophoectoderm layers from blastocysts, then plating the remaining inner cell mass cells onto a feeder layer of gamma-irradiated mouse embryonic fibroblasts. After 7-21 days in culture, cell outgrowths are removed, dissociated, then replated onto embryonic feeder layers. Colonies that form are then picked, briefly trypsinized to dissociate, then replated on embryonic feeder layers. The cells can be routinely split every 1-2 weeks using brief trypsinization. Although primate ES cells spontaneously differentiated in culture into cells of endoderm origin, differentiation of ES cells into neural cells was not reported.

Unfortunately, although a heterogeneous mixture of different cell types derived from ES cells is easy to obtain in culture, their targeted differentiation towards a specific lineage remains challenging. Even more difficult is to obtain cell populations which are synchronized at a particular differentiation stage (Pruszak et al., 2007). In general, spontaneous differentiation of ES cells in culture produces a heterogeneous mixture of cells, only some of which may be neural cells. Thus, spontaneous differentiation is not an effective means of providing neural precursor cells.

Methods of differentiating human ES cells into neural precursor cells have been developed that involve coculture of ES cells with mouse bone marrow feeder cells. However, the use of mouse feeder cells is not compatible with transplantation of cells into humans due to safety concerns.

Small molecules have also been tested for their ability to influence ES cell differentiation. For example, retinoic acid has been used to induce neuronal differentiation of ES cells. However, exposure to retinoic acid leads to differentiation mainly of glial cells, while human ES cells exposed to retinoic acid differentiate towards epithelial cells (Metallo et al., 2007). Thus, additional compounds and alternative methods of preparing neural precursor cells from human ES cells and other types of stem cells are needed to exploit the uses of cell therapy for treatment of neurological diseases.

SUMMARY OF THE INVENTION

In one aspect, the present invention provides a method of preparing one or more neural precursor cells in vitro. The method comprises exposing substantially, essentially, or completely undifferentiated mammalian pluripotent stem cells or neural stem cells to an effective amount of a differentiation agent under conditions sufficient to increase differentiation of the stem cells to neural precursor cells or neurons. The increased differentiation is determined by comparing the differentiation of the exposed cells to the differentiation that occurs when undifferentiated mammalian stem cells are treated under similar conditions but without exposure to the differentiation agent.

The differentiation agent is a compound having the following structure (I):

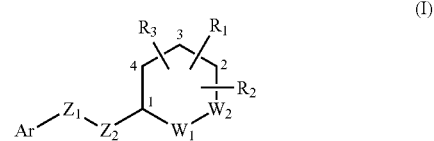

wherein:
the six membered ring defined by $W_1$, $W_2$ and carbon atoms 1, 2, 3 and 4, may be aromatic or non-aromatic, and further wherein any two neighboring atoms of this six membered ring may be singly or doubly bonded to one another;

$Z_1$ and $Z_2$ are either carbon or nitrogen, further wherein $Z_1$ and $Z_2$ may be singly, doubly, or triply bonded to one another and wherein $Z_2$ and carbon atom 1 may be singly or doubly bonded to one another, provided that the bond between $Z_1$ and $Z_2$ is not triple when $Z_1$ and $Z_2$ are nitrogen, further provided that the bond between $Z_1$ and $Z_2$ is single when the bond between $Z_2$ and carbon atom 1 is double;

Ar is a heteroatom-substituted or heteroatom-unsubstituted $\text{aryl}_{(C1-C12)}$;

one of either $W_1$ and $W_2$ is nitrogen and the other is carbon;

$R_1$, $R_2$, and $R_3$ are independently hydrogen, hydroxy, amino, cyano, halo, nitro, mercapto, or a heteroatom-substituted or heteroatom-unsubstituted $\text{alkyl}_{(C1-C8)}$, $\text{aryl}_{(C1-C8)}$, $\text{aralkyl}_{(C2-C8)}$, $\text{acyl}_{(C1-C8)}$, $\text{alkoxy}_{(C1-C8)}$, $\text{alkylamino}_{(C1-C8)}$, or $=O$;

or pharmaceutically acceptable salts, hydrates, tautomers, acetals, ketals, hemiacetals, hemiketals, or optical isomers thereof.

Preferably, $Z_1$ and $Z_2$ are both carbon triply bonded to each other, or $Z_1$ and $Z_2$ are both nitrogen doubly bonded to each other.

The differentiation agent can be: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl)diazenylpyridine-2,6-diamine; 3-[(2-methyl-1,3-thiazol-4-yl)ethynyl]pyridine (MTEP); a physiologically acceptable salt thereof; or any combination thereof.

SIB 1893 has the structure:

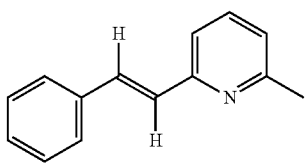

SIB 1757 has the structure:

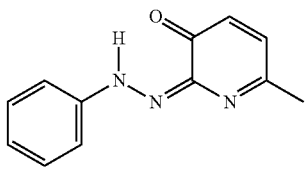 [SMILES: CC1=N/C(=N/Nc2ccccc2)C(=O)C=C1]

NSC41777 has the structure:

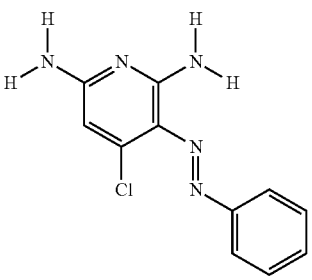 [SMILES: Nc1cc(Cl)c(/N=N/c2ccccc2)c(N)n1]

Phenazopyridine has the structure:

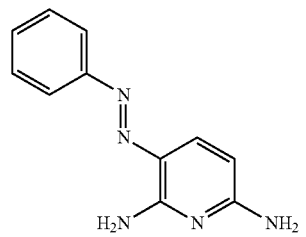

As shown in the below examples, phenazopyridine was tested in human ES cells, and phenazopyridine i) enhanced neuronal differentiation, ii) increased cell survival, iii) decreased amounts of non-neuronal and undifferentiated cells, and iv) synchronized the cellular differentiation state. Phenazopyridine was successfully used to promote differentiation of pluripotent cells into clinical grade neural precursors, which were then shown to have the ability to differentiate into different neuronal subtypes, including astrocytes and oligodendrocytes.

In certain embodiments, the method further comprises a method of measuring a pharmacological or toxicological property (e.g., neurotoxicity) of a test compound comprising contacting said neural precursor cells or neurons with the test compound. The neural precursor cells or neurons may be comprised in an engineered neural tissue (ENT). Cell survival, oxidative stress, or neural function of the neural precursor cells or neurons may be measured during or subsequent to said contacting. The neural precursor cells or neurons may transgenically express a protein marker or tag, such as a luminescent or fluorescent protein. The luminescent or fluorescent protein may be selected from the group consisting of GFP, eGFP, EBFP, EBFP2, Azurite, mKalama1, ECFP, Cerulean, CyPet, YFP, Citrine, Venus, YPet, firefly luciferase (Fluc) and Renilla luciferase (Rluc). Expression of the luminescent or fluorescent protein may be measured optically or via fluorescence activated cell sorting (FACS). The method may be automated or may comprise a high-throughput method. The pluripotent or neural stem cells may be differentiated into neural precursor cells or neurons.

In certain embodiments, the undifferentiated mammalian stem cells are pluripotent stem cells, which can be embryonic stem (ES) cells, induced pluripotent stem cells, or embryonic stem cells derived by somatic cell nuclear transfer. In other embodiments, the mammalian stem cells are adult or embryonic neural stem cells. In preferred embodiments, the undifferentiated stem cells are obtained from a cell culture. The cell culture can be a primary cell culture, a subculture of a primary cell culture, or a cell line. Preferably, the undifferentiated stem cells are of mouse, primate, mammal, human or monkey origin. In some embodiments, the stem cells are ES cells obtained from an embryo or a blastocyst. In other embodiments, the stem cells are ES cells obtained from a cell culture of undifferentiated ES cells.

It is anticipated that the differentiation of virtually any pluripotent stem cell or cell line, e.g., human embryonic stem cells or induced pluripotent stem cells (iPS cells), may be promoted via contacting the cell with a differentiation agent (e.g., phenazopyridine). For example, human embryonic stem cell line H1, H9, hES2, hES3, hES4, hES5, hES6, BG01, BG02, BG03, HSF1, HSF6, H1, H7, H9, H13B, and/or H14 etc. may be used in various embodiments according to the present invention. It is further anticipated that stem cell lines which subsequently become available may also be utilized in certain embodiments of the present invention. Teratoma cells may also be differentiated into a neuronal or neural-committed cell. In certain embodiments, the differentiation agent selectively promotes differentiation of the pluripotent cell into a neuronal or neural-committed cell.

Differentiation of induced pluripotent cells may also be promoted by contacting the induced pluripotent cell with a differentiation agent of the present invention. Induced pluripotent stem cells, commonly abbreviated as iPS cells or iPSCs, are a type of pluripotent stem cell artificially derived from a non-pluripotent cell, typically an adult somatic cell, by inserting certain genes, such as the combination of (Oct4, Sox2, Nanog, and Lin28) or (Oct 3/4, Sox2, Klf4, and c-myc). Induced pluripotent stem cells are believed to be essentially identical to natural pluripotent stem cells, such as embryonic stem cells, in many respects including the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed. IPS cells have been described previously (see, e.g., Takahashi et al., 2006; Takahashi et al., 2007; Yu et al, 2007). Generation of iPS cells is described, e.g., in U.S. Patent Application 2008/0233610 and European Patent Application EP1970446A1, which are incorporated herein by reference in their entirety.

A population of neural precursor cells prepared by exposure to the differentiation agent can have various characteristics. In certain embodiments, the neural precursor cells are synchronized such that a population of synchronized neural precursor cells is provided. In other embodiments, non-neural cells and undifferentiated cells are eliminated from cultures such that a more homogeneous population of neural precursor cells is provided.

In another aspect, the present invention provides a population of neuronal precursor cells prepared by the forgoing method of preparing one or more neural precursor cells in vitro.

In a further aspect, the present invention provides a method of enhancing neural precursor cell survival in vitro. The method comprises exposing a neural precursor cell to an effective amount of an active agent under conditions sufficient to enhance cell survival of the neural precursor cell. Cell survival is determined by comparing the survival of the exposed cell to cell survival under similar conditions but without exposure to the active agent. The neural precursor cell is of mammalian origin, and is preferably a mouse, human or monkey cell. In certain embodiments, the neural precursor cell can be prepared by exposing undifferentiated mammalian pluripotent stem cells or neural stem cells to the active agent. In other embodiments, the neural precursor cell is obtained from a culture of neural precursor cells, such as a primary cell culture from brain tissue, or a culture of neural precursor cells differentiated in vitro.

The active agent is a compound having the structure (I). In the compound of structure (I), $Z_1$ and $Z_2$ are preferably both carbon triply bonded to each other, or preferably both nitrogen doubly bonded to each other. The active agent can be: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

In another aspect, the present invention provides a method of preparing neuronal cells in vitro, including neurons, astrocytes and oligodendrocytes. The method comprises a) exposing substantially, essentially, or completely undifferentiated mammalian pluripotent stem cells or neural stem cells to an effective amount of a differentiation agent under conditions sufficient to enhance differentiation of the stem cells to neural precursor cells as compared to differentiation under similar conditions without the differentiation agent; and b) then incubating the neural precursor cells in the absence of the differentiation agent under conditions sufficient to differentiate the neural precursor cells into neurons, astrocytes or oligodendrocytes. In certain embodiments, the neurons, astrocytes or oligodendrocytes are present in an engineered neural tissue (ENT).

The differentiation agent is the compound of structure (I). Preferably, $Z_1$ and $Z_2$ are both carbon triply bonded to each other, or both nitrogen doubly bonded to each other. The differentiation agent is preferably: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

In some embodiments, the undifferentiated mammalian stem cells are pluripotent stem cells, which can be ES cells, induced pluripotent stem cells, or embryonic stem cells derived by somatic cell nuclear transfer. In other embodiments, the mammalian stem cells are adult or embryonic neural stem cells. Preferably, the undifferentiated stem cells are of mouse, human or monkey origin. In some embodiments, the stem cells are ES cells obtained from an embryo or a blastocyst. In other embodiments, the stem cells are ES cells obtained from a cell culture of undifferentiated ES cells.

In a further aspect, the present invention provides a method of directing the differentiation of pluripotent stem cells or neural stem cells into neural cells in vitro. The method comprises exposing the substantially, essentially, or completely undifferentiated stem cells to an effective amount of a differentiation compound under conditions sufficient to enhance differentiation of the stem cells to neural cells as compared to differentiation under similar conditions without the compound.

The differentiation compound is a compound of structure (I). Preferably, $Z_1$ and $Z_2$ are both carbon triply bonded to each other, or both nitrogen doubly bonded to each other. In certain embodiments, the differentiation compound is: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

With respect to the exposure of cells in vitro to a pyridine derivative or other compounds of the present invention, the term "effective amount" means an amount sufficient to bring about the desired in vitro result, such as enhancing differentiation of stem cells or enhancing neural precursor cell survival.

In another aspect, the present invention provides a method of treating nervous system damage, comprising administering to a patient in need of such treatment an effective amount of a pyridine derivative of structure (I). Preferably, $Z_1$ and $Z_2$ are both carbon triply bonded to each other, or both nitrogen doubly bonded to each other.

The pyridine derivative is preferably: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof or any combination thereof.

The nervous system damage can be due to a neurodegenerative disorder, such as Alzheimer's disease, frontotemporal dementia, dementia with Lewy bodies, amyotrophic lateral sclerosis, Parkinson's disease and Huntington's disease, or to nervous system injury from trauma such as ischemic cerebral stroke, spinal cord lesions and brain injury.

In certain embodiments, neuronal or neuronal-committed cells differentiated or cultured according to the present invention may be used to evaluate a test compound, e.g., for neuronal activity or toxicity. In certain embodiments, a property of one or more compounds (e.g., toxicity) may be evaluated by contacting the neuronal or neuronal-committed cells of the present invention with the test compound(s). In embodiments where the toxicity of a test compound is evaluated, parameters such as cell death (necrosis, apoptosis), excitotoxicity, altered neuronal function (e.g., altered generation of action potentials or long-term potentiation, etc.), altered brain receptor function, decreased resistance to challenge with a known toxic compound, synaptic toxicity, developmental neurotoxicity, neural lineage-specific toxicity (e.g., in oligodendrocytes, astrocytes, or dopaminergic neurons) may be assessed in the cells. In certain embodiments, dose-response relationships may be generated to assess the toxicity of a test compound. Multiple compounds or part or all of a small molecule library may be screened for toxicity or neuronal activity in cells cultured according to the present invention. Some or essentially all of the neuronal or neuronal-committed cells may be further differentiated into dopaminergic cells prior to the assessment of the toxicity of a test compound; this may be particularly useful in instances where it may be desirable to understand the dopaminergic toxicity of a compound. In certain embodiments, one or more of the steps involved with culturing cells, differentiating cells, and/or evaluating the a property (e.g., the toxicity) of a test compound may be standardized and/or automated, e.g., via the use of robotics. For example, various robotics may be used to culture cells, add or remove media from the cells, add a test compound to media comprising neuronal or neuronally-committed cells differentiated according to the present invention. Specific robotics which may be used with the methods of the present invention include cell dispensers that allow automated and standardized distribution of cells in multiwells which typically range from 12 to 384 wells although a higher or lower number of wells can be used as desired (e.g., Matrix Well-Mate™ from Thermo Fisher Scientific, Inc.) and multichannel liquid handlers that allow automated distribution of library compounds into multiwell plates and automated dilutions of compounds, e.g., for $IC_{50}$ calculations (e.g., Zephyr from Caliper Life Sciences).

The novel features which are believed to be characteristic of the invention, both as to its organization and method of operation, together with further objects and advantages will be better understood from the following description when considered in connection with the accompanying figures. It is to be expressly understood, however, that each of the figures and examples is provided for the purpose of illustration and description only and is not intended as a definition of the limits of the present invention It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

FIGS. 1A-H: phase contrast pictures of control (FIGS. 1A-D) and phenazopyridine (FIGS. E-H) treated cells at different time points. FIG. 1I: percentage of living single cells by trypan blue exclusion at different time points in control (blue bars) or phenazopyridine-treated cells (purple bars). PAP: phenazopyridine. Scale bars: 50:m. : $p<0.01$; *: $p<0.001$.

FIG. 3: A macroscopic view of ENTs grown in the presence or absence of phenazopyridin. Exposure to phenazopridine resulted in ENT which were more homogenous and appeared to contain a reduced amount of non-neural cells.

FIG. 4: Staining for the presence or absence of the cartilage marker tenascin C in ENTs grown in the presence or absence of phenazopyridine. As shown in FIG. 6, cartilage was not observed in ENTs grown in the presence of phenazopyridine based on immunofluorescent staining of tenascin C.

FIGS. 5A-I: Three-dimensional air-liquid interface culture of ESC-derived neural precursors. (FIG. 5A): Schematic representations of air/liquid interface culture. (FIG. 5A) Colonies of human ESC (H1 line) were induced to differentiate towards neural precursor cells (NPC) through coculture with MS5 stromal cells or culture in chemically-defined neural induction medium; after one month, rosette-rich clusters were mechanically removed and plated on semipermeable membranes. (FIG. 5B-D): Expansion on membrane of MS5-induced rosette clusters. Rosette cluster before removal and plating (FIG. 5B). Cell growth one week after plating; dotted zones indicate the location of three initially plated clusters (FIG. 5C). Development of a compact cell mass one month after plating, showing numerous newly-formed rosettes (FIG. 5D). FIG. 5E: Early aggregates of human ESC after 4 days of suspension culture in a chemically-defined neural induction medium were directly plated on semipermeable membranes. (FIG. 5F-I) Expansion of early ESC aggregates. 10-20 four day old ESC aggregates were plated (FIG. 5F). Two days after plating, ESC aggregates attached and rapidly fused to form clusters (FIG. 5G). One month after plating, ESC aggregates develop to a compact cell mass similarly to that observed with rosette-rich clusters (FIG. 5H). Macroscopic view after one month culture (FIG. 5I).

FIGS. 6A-F: Primary screen on mouse ES cells. FIGS. 6A-C: CGR8 mouse ES cells were transduced with a lentivector expressing mRFP1 under the control of the Tα1 α-tubulin neuron-specific promoter (Tα1) and GFP under the control of the ubiquitous EF1-α short promoter (EF1-αS) (FIG. 6A). cPPT: central polypurine tract. WPRE: Woodchuck Hepatitis Virus Posttranscriptional Regulatory Element. FIG. 6B: Cells undergoing neuronal differentiation were immunostained against β3-tubulin (blue). Scale bar: 100 μm. The ratio between red and green fluorescence was quantified in undifferentiated cells as well as β3 tubulin-positive and β3 tubulin-negative cells undergoing neuronal differentiation (FIG. 6C). Red bars indicate mean values. FIG. 6D: Lentiviral construct used for the primary screening assay. Firefly luciferase (Fluc) expression is controlled by the Tα1 α-tubulin promoter, and Renilla luciferase (Rluc) expression is controlled by the EF1-α short promoter. FIG. 6E: Mouse ES cells were transduced with the construct described in panel FIG. 6D; the ratio between Firefly luciferase and Renilla luciferase activities (Fluc/Rluc) was measured in undifferentiated cells (ES) and in cells induced towards neuronal differentiation (MS5) or not (MEF) at different time points. Values were normalized on those obtained with MEFs at day 3. FIG. 6F: Results of the primary screening assay, shown as Fluc/Rluc ratio values of CGR8$_{dual\,luc}$ treated with each compound of the small molecule library, normalized to values obtained with DMSO alone. ***: p<0.001. Error bars: standard error of the mean.

FIGS. 7A-B: Phenazopyridine enhances neuronal differentiation of human ES cells. Human ES cells were cultured for 6 weeks with phenazopyridine (PAP) at 3 μM or DMSO only, and subsequently replated without further treatment. Cells were immunostained for neuronal markers at different time points. FIG. 7A: quantification of neurite outgrowth divided by total cell number at different time points. Blue: control-treated cells; purple: phenazopyridine-treated cells. Scale bars: 100 μm. FIG. 7B: quantification of neural tube number per three-dimensional human ES cell neuronal differentiation culture after 2 weeks and 4 weeks of differentiation. White: control-treated cells; black: phenazopyridine-treated cells. **: p<0.01. Error bars: standard error of the mean.

FIG. 8A-B: Phenazopyridine treatment allows the generation of a homogenous monolayer of synchronized neuronal precursors. Human ES cells were cultured for 4 weeks using the differentiation protocol 2 (see Methods), treated with DMSO alone or phenazopyridine (3 μM). Cells were subsequently immunostained for markers of neuronal differentiation and for alkaline phosphatase, marking undifferentiated ES cells. Quantification of cells expressing different markers in DMSO-treated cells (FIG. 8A) and phenazopyridine-treated cells (FIG. 8B). Error bars: standard error of the mean.

FIGS. 9A-C: Real Time PCR analysis of phenazopyridine-treated ES cells. Human ES cells were differentiated into neuronal precursors using the second differentiation protocol with DMSO or phenazopyridine (3 μM), and Real Time PCR was performed. FIG. 9A: Neural marker expression after two weeks of differentiation. B-C: Non-neural marker expression after two (FIG. 9B) or four weeks of differentiation (FIG. 9C). Data were normalized to values obtained with DMSO-treated cells at 2 weeks of differentiation. White bars: DMSO-treated cells. Black bars: phenazopyridine-treated cells. NS: no statistical differences. *: p<0.05; ***: p<0.001. Error bars: standard error of the mean.

DETAILED DESCRIPTION OF THE INVENTION

Differentiation Agent and Chemical Groups

Figure 1:
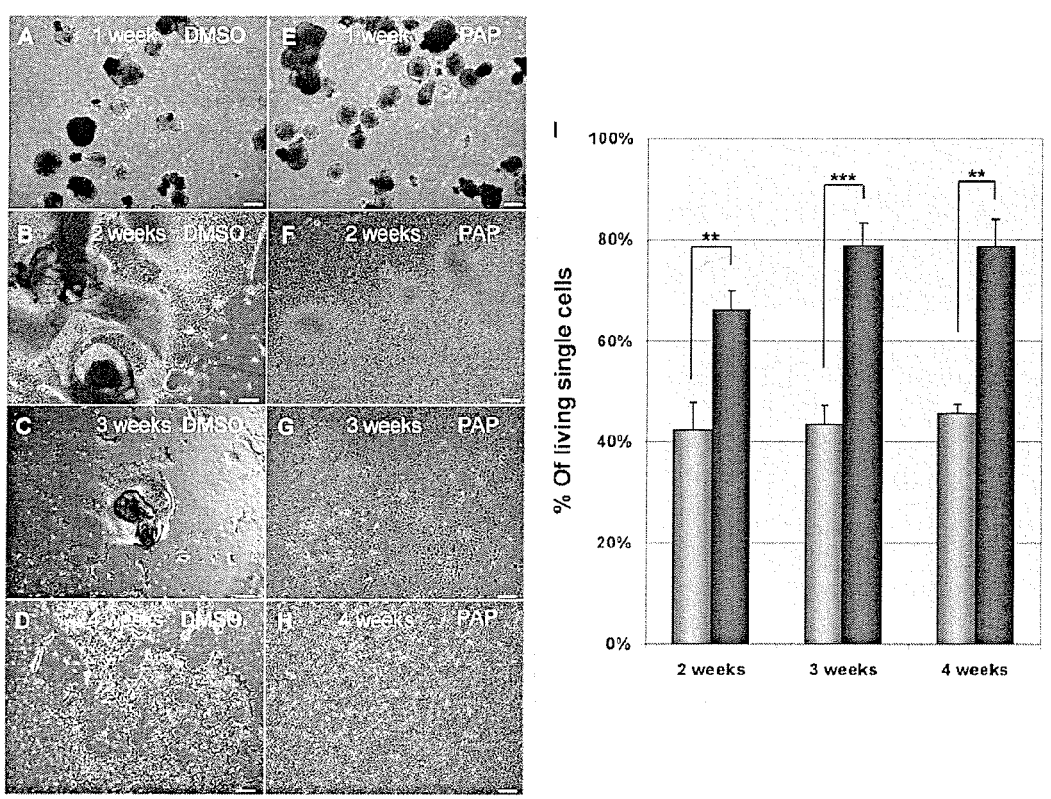
FIGS. 1A-I: A panel of photographs showing the effect of phenazopyridine on the differentiation of human ES cells.

In some embodiments of the present invention, undifferentiated mammalian pluripotent stem cells or neural stem cells are exposed to a differentiation agent for the preparation of neural precursor cells. As used herein, the term "differentiation agent" means one or more compounds that enhance the differentiation of stem cells to neural precursor cells without any restriction as to the mode of action of the compound(s). For example, the agent may assist the differentiation process by acting on a cell surface receptor, acting in the nucleus to regulate gene expression, acting on a protein in the cytoplasm, inducing or assisting a change in cell phenotype, promoting growth of cells with a particular phenotype or retarding the growth of others, or acting in concert with other agents through unknown mechanisms.

A differentiation agent in accordance with the present invention is a compound having the following structure (I):

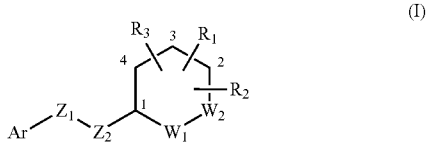

wherein:

the six membered ring defined by $W_1$, $W_2$ and carbon atoms 1, 2, 3 and 4, may be aromatic or non-aromatic, and further wherein any two neighboring atoms of this six membered ring may be singly or doubly bonded to one another;

$Z_1$ and $Z_2$ are either carbon or nitrogen, further wherein $Z_1$ and $Z_2$ may be singly, doubly, or triply bonded to one another and wherein $Z_2$ and carbon atom 1 may be singly or doubly bonded to one another, provided that the bond between $Z_1$ and $Z_2$ is not triple when $Z_1$ and $Z_2$ are nitrogen, further provided that the bond between $Z_1$ and $Z_2$ is single when the bond between $Z_2$ and carbon atom 1 is double;

Ar is a heteroatom-substituted or heteroatom-unsubstituted aryl$_{(C1-C12)}$;

one of either $W_1$ and $W_2$ is nitrogen and the other is carbon;

$R_1$, $R_2$, and $R_3$ are independently hydrogen, hydroxy, amino, cyano, halo, nitro, mercapto, or a heteroatom-substituted or heteroatom-unsubstituted alkyl$_{(C1-C8)}$, aryl$_{(C1-C8)}$, aralkyl$_{(C2-C8)}$, acyl$_{(C1-C8)}$, alkoxy$_{(C1-C8)}$, alkylamino$_{(C1-C8)}$, or =O;

or pharmaceutically acceptable salts, hydrates, tautomers, acetals, ketals, hemiacetals, hemiketals, or optical isomers thereof.

In preferred embodiments, $Z_1$ and $Z_2$ are both carbon triply bonded to each other. In other preferred embodiments, $Z_1$ and $Z_2$ are both nitrogen doubly bonded to each other.

Particularly preferred embodiments include: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

As used herein, the term "amino" means —NH$_2$; the term "nitro" means —NO$_2$; the term "halo" designates —F, —Cl, —Br or —I; the term "mercapto" means —SH; the term "cyano" means —CN; the term "azido" means —N$_3$; the term "silyl" means —SiH$_3$, and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted alkyl$_{(Cn)}$, and heteroatom-substituted alkyl$_{(Cn)}$. The term "heteroatom-unsubstituted alkyl$_{(Cn)}$" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted alkyl$_{(C1-C10)}$ has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tent-butyl), —CH$_2$C(CH$_3$)$_3$ (neopentyl), cyclobutyl, cyclopentyl, and cyclohexyl, are all non-limiting examples of heteroatom-unsubstituted alkyl groups. The term "heteroatom-substituted alkyl$_{(C_n)}$" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted alkyl$_{(C1-C10)}$ has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" includes straight-chain alkanediyl, branched-chain alkanediyl, cycloalkanediyl, cyclic alkanediyl, heteroatom-unsubstituted alkanediyl, heteroatom-substituted alkanediyl, heteroatom-unsubstituted alkanediyl$_{(C_n)}$, and heteroatom-substituted alkanediyl$_{(C_n)}$. The term "heteroatom-unsubstituted alkanediyl$_{(C_n)}$" refers to a diradical, having a linear or branched, cyclic or acyclic structure, further having no carbon-carbon double or triple bonds, further having a total of n carbon atoms, all of which are nonaromatic, 2 or more hydrogen atoms, and no heteroatoms. For example, a heteroatom-unsubstituted alkanediyl$_{(C1-C10)}$ has 1 to 10 carbon atoms. The groups, —CH$_2$— (methylene), —CH$_2$CH$_2$, and —CH$_2$CH$_2$CH$_2$, are all non-limiting examples of heteroatom-unsubstituted alkanediyl groups. The term "heteroatom-substituted alkanediyl$_{(C_n)}$" refers to a radical, having two points of attachment to one or two saturated carbon atoms, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted alkanediyl$_{(C1-C10)}$ has 1 to 10 carbon atoms. The following groups are all non-limiting examples of heteroatom-substituted alkanediyl groups: —CH(F)—, CF$_2$—, —CH(Cl)—, —CH(OH)—, —CH(OCH$_3$)—, and —CH$_2$CH(Cl)—.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted alkenyl$_{(C_n)}$, and heteroatom-substituted alkenyl$_{(C_n)}$. The term "heteroatom-unsubstituted alkenyl$_{(C_n)}$" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted alkenyl$_{(C2-C10)}$ has 2 to 10 carbon atoms. Heteroatom-unsubstituted alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "heteroatom-substituted alkenyl$_{(C_n)}$" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted alkenyl$_{(C2-C10)}$ has 2 to 10 carbon atoms. The groups, —CH=CHF, —CH=CHCl and —CH=CHBr, are non-limiting examples of heteroatom-substituted alkenyl groups.

The term "alkynyl" includes straight-chain alkynyl, branched-chain alkynyl, cycloalkynyl, cyclic alkynyl, heteroatom-unsubstituted alkynyl, heteroatom-substituted alkynyl, heteroatom-unsubstituted alkynyl$_{(C_n)}$, and heteroatom-substituted alkynyl$_{(C_n)}$. The term "heteroatom-unsubstituted alkynyl$_{(C_n)}$" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted alkynyl$_{(C2-C10)}$ has 2 to 10 carbon atoms. The groups, —C≡CH, —C≡CCH$_3$, and —C≡CC$_6$H$_5$ are non-limiting examples of heteroatom-unsubstituted alkynyl groups. The term "heteroatom-substituted alkynyl$_{(C_n)}$" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted alkynyl$_{(C2-C10)}$ has 2 to 10 carbon atoms. The group, —C≡CSi(CH$_3$)$_3$, is a non-limiting example of a heteroatom-substituted alkynyl group.

The term "aryl" includes heteroatom-unsubstituted aryl, heteroatom-substituted aryl, heteroatom-unsubstituted aryl$_{(C_n)}$, heteroatom-substituted aryl$_{(C_n)}$, heteroaryl, heterocyclic aryl groups, carbocyclic aryl groups, biaryl groups, and single-valent radicals derived from polycyclic fused hydrocarbons (PAHs). The term "heteroatom-unsubstituted aryl$_{(C_n)}$" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted aryl$_{(C6-C10)}$ has 6 to 10 carbon atoms. Non-limiting examples of heteroatom-unsubstituted aryl groups include phenyl (Ph), methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-substituted aryl$_{(C_n)}$" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-substituted heteroaryl$_{(C1-C10)}$ has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, C$_6$H$_4$CONH$_2$, C$_6$H$_4$CONHCH$_3$, —C$_6$H$_4$CON(CH$_3$)$_2$, furanyl, thienyl, pyridyl, pyrrolyl, pyrimidyl, pyrazinyl, quinolyl, indolyl, and imidazoyl.

The term "aralkyl" includes heteroatom-unsubstituted aralkyl, heteroatom-substituted aralkyl, heteroatom-unsubstituted aralkyl$_{(C_n)}$, heteroatom-substituted aralkyl$_{(C_n)}$, heteroaralkyl, and heterocyclic aralkyl groups. The term "heteroatom-unsubstituted aralkyl$_{(Cn)}$" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted aralkyl$_{(C7-C10)}$ has 7 to 10 carbon atoms. Non-limiting examples of heteroatom-unsubstituted aralkyls are: phenylmethyl (benzyl, Bn) and phenylethyl. The term "heteroatom-substituted aralkyl$_{(Cn)}$" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted heteroaralkyl$_{(C2-C10)}$ has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted acyl$_{(Cn)}$, heteroatom-substituted acyl$_{(Cn)}$, alkylcarbonyl, alkoxycarbonyl and aminocarbonyl groups. The term "heteroatom-unsubstituted acyl$_{(Cn)}$" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted acyl$_{(C1-C10)}$ has 1 to carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and COC$_6$H$_3$(CH$_3$)$_2$, are non-limiting examples of heteroatom-unsubstituted acyl groups. The term "heteroatom-substituted acyl$_{(Cn)}$" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted acyl$_{(C1-C10)}$ has 1 to 10 carbon atoms. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted alkoxy$_{(Cn)}$, and heteroatom-substituted alkoxy$_{(Cn)}$. The term "heteroatom-unsubstituted alkoxy$_{(Cn)}$" refers to a group, having the structure —OR, in which R is a heteroatom-unsubstituted alkyl$_{(Cn)}$, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted alkoxy$_{(Cn)}$" refers to a group, having the structure —OR, in which R is a heteroatom-substituted alkyl$_{(Cn)}$, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted alkenyloxy$_{(Cn)}$, and heteroatom-substituted alkenyloxy$_{(Cn)}$. The term "heteroatom-unsubstituted alkenyloxy$_{(Cn)}$" refers to a group, having the structure —OR, in which R is a heteroatom-unsubstituted alkenyl$_{(Cn)}$, as that term is defined above. The term "heteroatom-substituted alkenyloxy$_{(Cn)}$" refers to a group, having the structure —OR, in which R is a heteroatom-substituted alkenyl$_{(Cn)}$, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted alkynyloxy$_{(Cn)}$, and heteroatom-substituted alkynyloxy$_{(Cn)}$. The term "heteroatom-unsubstituted alkynyloxy$_{(Cn)}$" refers to a group, having the structure —OR, in which R is a heteroatom-unsubstituted alkynyl$_{(Cn)}$, as that term is defined above. The term "heteroatom-substituted alkynyloxy$_{(Cn)}$" refers to a group, having the structure —OR, in which R is a heteroatom-substituted alkynyl$_{(Cn)}$, as that term is defined above.

The term "aryloxy" includes heteroatom-unsubstituted aryloxy, heteroatom-substituted aryloxy, heteroatom-unsubstituted aryloxy$_{(Cn)}$, heteroatom-substituted aryloxy$_{(Cn)}$, heteroaryloxy, and heterocyclic aryloxy groups. The term "heteroatom-unsubstituted aryloxy$_{(Cn)}$" refers to a group, having the structure —OAr, in which Ar is a heteroatom-unsubstituted aryl$_{(Cn)}$, as that term is defined above. A non-limiting example of a heteroatom-unsubstituted aryloxy group is —OC$_6$H$_5$. The term "heteroatom-substituted aryloxy$_{(Cn)}$" refers to a group, having the structure —OAr, in which Ar is a heteroatom-substituted aryl$_{(Cn)}$, as that term is defined above.

The term "aralkyloxy" includes heteroatom-unsubstituted aralkyloxy, heteroatom-substituted aralkyloxy, heteroatom-unsubstituted aralkyloxy$_{(Cn)}$, heteroatom-substituted aralkyloxy$_{(Cn)}$, heteroaralkyloxy, and heterocyclic aralkyloxy groups. The term "heteroatom-unsubstituted aralkyloxy$_{(Cn)}$" refers to a group, having the structure —OAr, in which Ar is a heteroatom-unsubstituted aralkyl$_{(Cn)}$, as that term is defined above. The term "heteroatom-substituted aralkyloxy$_{(Cn)}$" refers to a group, having the structure —OAr, in which Ar is a heteroatom-substituted aralkyl$_{(Cn)}$, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted acyloxy$_{(Cn)}$, heteroatom-substituted acyloxy$_{(Cn)}$, alkylcarbonyloxy, arylcarbonyloxy, alkoxycarbonyloxy, aryloxycarbonyloxy, and carboxylate groups. The term "heteroatom-unsubstituted acyloxy$_{(Cn)}$" refers to a group, having the structure —OAc, in which Ac is a heteroatom-unsubstituted acyl$_{(Cn)}$, as that term is defined above. For example, —OC(O)CH$_3$ is a non-limiting example of a heteroatom-unsubstituted acyloxy group. The term "heteroatom-substituted acyloxy$_{(Cn)}$" refers to a group, having the structure —OAc, in which Ac is a heteroatom-substituted acyl$_{(Cn)}$, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted alkylamino$_{(Cn)}$, and heteroatom-substituted alkylamino$_{(Cn)}$. The term "heteroatom-unsubstituted alkylamino$_{(Cn)}$" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted alkylamino$_{(C_1-C_{10})}$ has 1 to 10 carbon atoms. The term "heteroatom-unsubstituted alkylamino$_{(C_n)}$" includes groups, having the structure —NHR, in which R is a heteroatom-unsubstituted alkyl$_{(C_n)}$, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted alkylamino$_{(C_n)}$" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkylamino$_{(C_1-C_{10})}$ has 1 to 10 carbon atoms. The term "heteroatom-substituted alkylamino$_{(C_n)}$" includes groups, having the structure —NHR, in which R is a heteroatom-substituted alkyl$_{(C_n)}$, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted alkenylamino$_{(C_n)}$, heteroatom-substituted alkenylamino$_{(C_n)}$, dialkenylamino, and alkyl(alkenyl)amino groups. The term "heteroatom-unsubstituted alkenylamino$_{(C_n)}$" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted alkenylamino$_{(C_2-C_{10})}$ has 2 to 10 carbon atoms. The term "heteroatom-unsubstituted alkenylamino$_{(C_n)}$" includes groups, having the structure —NHR, in which R is a heteroatom-unsubstituted alkenyl$_{(C_n)}$, as that term is defined above. The term "heteroatom-substituted alkenylamino$_{(C_n)}$" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkenylamino$_{(C_2-C_{10})}$ has 2 to 10 carbon atoms. The term "heteroatom-substituted alkenylamino$_{(C_n)}$" includes groups, having the structure —NHR, in which R is a heteroatom-substituted alkenyl$_{(C_n)}$, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, hetero atom-unsubstituted alkynylamino$_{(C_n)}$, heteroatom-substituted alkynylamino$_{(C_n)}$, dialkynylamino, alkyl(alkynyl)amino, and alkenyl(alkynyl)amino groups. The term "heteroatom-unsubstituted alkynylamino$_{(C_n)}$" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted alkynylamino$_{(C_2-C_{10})}$ has 2 to 10 carbon atoms. The term "heteroatom-unsubstituted alkynylamino$_{(C_n)}$" includes groups, having the structure —NHR, in which R is a heteroatom-unsubstituted alkynyl$_{(C_n)}$, as that term is defined above. The term "heteroatom-substituted alkynylamino$_{(C_n)}$" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted alkynylamino$_{(C_2-C_{10})}$ has 2 to 10 carbon atoms. The term "heteroatom-substituted alkynylamino$_{(C_n)}$" includes groups, having the structure —NHR, in which R is a heteroatom-substituted alkynyl$_{(C_n)}$, as that term is defined above.

The term "arylamino" includes heteroatom-unsubstituted arylamino, heteroatom-substituted arylamino, heteroatom-unsubstituted arylamino$_{(C_n)}$, heteroatom-substituted arylamino$_{(C_n)}$, heteroarylamino, heterocyclic arylamino, and alkyl(aryl)amino groups. The term "heteroatom-unsubstituted arylamino$_{(C_n)}$" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted arylamino$_{(C_6-C_{10})}$ has 6 to 10 carbon atoms. The term "heteroatom-unsubstituted arylamino$_{(C_n)}$" includes groups, having the structure —NHR, in which R is a heteroatom-unsubstituted aryl$_{(C_n)}$, as that term is defined above. The term "heteroatom-substituted arylamino$_{(C_n)}$" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted arylamino$_{(C_6-C_{10})}$ has 6 to 10 carbon atoms. The term "heteroatom-substituted arylamino$_{(C_n)}$" includes groups, having the structure —NHR, in which R is a heteroatom-substituted aryl$_{(C_n)}$, as that term is defined above.

The term "aralkylamino" includes heteroatom-unsubstituted aralkylamino, heteroatom-substituted aralkylamino, heteroatom-unsubstituted aralkylamino$_{(C_n)}$, heteroatom-substituted aralkylamino$_{(C_n)}$, heteroaralkylamino, heterocyclic aralkylamino groups, and diaralkylamino groups. The term "heteroatom-unsubstituted aralkylamino$_{(C_n)}$" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted aralkylamino$_{(C7-C10)}$ has 7 to 10 carbon atoms. The term "heteroatom-unsubstituted aralkylamino$_{(Cn)}$" includes groups, having the structure —NHR, in which R is a heteroatom-unsubstituted aralkyl$_{(Cn)}$, as that term is defined above. The term "heteroatom-substituted aralkylamino$_{(Cn)}$" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted aralkylamino$_{(C7-C10)}$ has 7 to 10 carbon atoms. The term "heteroatom-substituted aralkylamino$_{(Cn)}$" includes groups, having the structure —NHR, in which R is a heteroatom-substituted aralkyl$_{(Cn)}$, as that term is defined above.

The term "amido" includes straight-chain amido, branched-chain amido, cycloamido, cyclic amido, heteroatom-unsubstituted amido, heteroatom-substituted amido, heteroatom-unsubstituted amido$_{(Cn)}$, heteroatom-substituted amido$_{(Cn)}$, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted amido$_{(Cn)}$" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted amido$_{(C1-C10)}$ has 1 to 10 carbon atoms. The term "heteroatom-unsubstituted amido$_{(Cn)}$" includes groups, having the structure —NHR, in which R is a heteroatom-unsubstituted acyl$_{(Cn)}$, as that term is defined above. The group, —NHC(O)CH$_3$, is a non-limiting example of a heteroatom-unsubstituted amido group. The term "heteroatom-substituted amido$_{(Cn)}$" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted amido$_{(C1-C10)}$ has 1 to 10 carbon atoms. The term "heteroatom-substituted amido$_{(Cn)}$" includes groups, having the structure —NHR, in which R is a heteroatom-unsubstituted acyl$_{(Cn)}$, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted alkylthio$_{(Cn)}$, and heteroatom-substituted alkylthio$_{(Cn)}$. The term "heteroatom-unsubstituted alkylthio$_{(Cn)}$" refers to a group, having the structure —SR, in which R is a heteroatom-unsubstituted alkyl$_{(Cn)}$, as that term is defined above. The group, —SCH$_3$, is an example of a heteroatom-unsubstituted alkylthio group. The term "heteroatom-substituted alkylthio$_{(Cn)}$" refers to a group, having the structure —SR, in which R is a heteroatom-substituted alkyl$_{(Cn)}$, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted alkenylthio$_{(Cn)}$, and heteroatom-substituted alkenylthio$_{(Cn)}$. The term "heteroatom-unsubstituted alkenylthio$_{(Cn)}$" refers to a group, having the structure —SR, in which R is a heteroatom-unsubstituted alkenyl$_{(Cn)}$, as that term is defined above. The term "heteroatom-substituted alkenylthio$_{(Cn)}$" refers to a group, having the structure —SR, in which R is a heteroatom-substituted alkenyl$_{(Cn)}$, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted alkynylthio$_{(Cn)}$, and heteroatom-substituted alkynylthio$_{(Cn)}$. The term "heteroatom-unsubstituted alkynylthio$_{(Cn)}$" refers to a group, having the structure —SR, in which R is a heteroatom-unsubstituted alkynyl$_{(Cn)}$, as that term is defined above. The term "heteroatom-substituted alkynylthio$_{(Cn)}$" refers to a group, having the structure —SR, in which R is a heteroatom-substituted alkynyl$_{(Cn)}$, as that term is defined above.

The term "arylthio" includes heteroatom-unsubstituted arylthio, heteroatom-substituted arylthio, heteroatom-unsubstituted arylthio$_{(Cn)}$, heteroatom-substituted arylthio$_{(Cn)}$, heteroarylthio, and heterocyclic arylthio groups. The term "heteroatom-unsubstituted arylthio$_{(Cn)}$" refers to a group, having the structure —SAr, in which Ar is a heteroatom-unsubstituted aryl$_{(Cn)}$, as that term is defined above. The group, —SC$_6$H$_5$, is an example of a heteroatom-unsubstituted arylthio group. The term "heteroatom-substituted arylthio$_{(Cn)}$" refers to a group, having the structure —SAr, in which Ar is a heteroatom-substituted aryl$_{(Cn)}$, as that term is defined above.

The term "aralkylthio" includes heteroatom-unsubstituted aralkylthio, heteroatom-substituted aralkylthio, heteroatom-unsubstituted aralkylthio$_{(Cn)}$, heteroatom-substituted aralkylthio$_{(Cn)}$, heteroaralkylthio, and heterocyclic aralkylthio groups. The term "heteroatom-unsubstituted aralkylthio$_{(Cn)}$" refers to a group, having the structure —SAr, in which Ar is a heteroatom-unsubstituted aralkyl$_{(Cn)}$, as that term is defined above. The group, —SCH$_2$C$_6$H$_5$, is an example of a heteroatom-unsubstituted aralkyl group. The term "heteroatom-substituted aralkylthio$_{(Cn)}$" refers to a group, having the structure —SAr, in which Ar is a heteroatom-substituted aralkyl$_{(Cn)}$, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted acylthio$_{(Cn)}$, heteroatom-substituted acylthio$_{(Cn)}$, alkylcarbonyloxy, arylcarbonyloxy, alkoxycarbonyloxy, aryloxycarbonyloxy, and carboxylate groups. The term "heteroatom-unsubstituted acylthio$_{(Cn)}$" refers to a group, having the structure —SAc, in which Ac is a heteroatom-unsubstituted acyl$_{(Cn)}$, as that term is defined above. The group, —SCOCH$_3$, is an example of a heteroatom-unsubstituted acylthio group. The term "heteroatom-substituted acylthio$_{(Cn)}$" refers to a group, having the structure —SAc, in which Ac is a heteroatom-substituted acyl$_{(Cn)}$, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted alkylsilyl$_{(C_n)}$, and heteroatom-substituted alkylsilyl$_{(C_n)}$. The term "heteroatom-unsubstituted alkylsilyl$_{(C_n)}$" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted alkylsilyl$_{(C1-C10)}$ has 1 to 10 carbon atoms. An alkylsilyl group includes dialkylamino groups. The groups, —Si(CH$_3$)$_3$ and —Si(CH$_3$)$_2$C(CH$_3$)$_3$, are non-limiting examples of heteroatom-unsubstituted alkylsilyl groups. The term "heteroatom-substituted alkylsilyl$_{(C_n)}$" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted alkylsilyl$_{(C1-C10)}$ has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted phosphonate$_{(C_n)}$, and heteroatom-substituted phosphonate$_{(C_n)}$. The term "heteroatom-unsubstituted phosphonate$_{(C_n)}$" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted phosphonate$_{(C0-C10)}$ has 0 to 10 carbon atoms. The groups, —P(O)(OH)$_2$, —P(O)(OH)OCH$_3$, —P(O)(OH)OCH$_2$CH$_3$, —P(O)(OCH$_3$)$_2$, and —P(O)(OH)(OC$_6$H$_5$) are non-limiting examples of heteroatom-unsubstituted phosphonate groups. The term "heteroatom-substituted C$_n$-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted phosphonate $_{(C0-C10)}$ has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted phosphinate$_{(C_n)}$, and heteroatom-substituted phosphinate$_{(C_n)}$. The term "heteroatom-unsubstituted phosphinate$_{(C_n)}$" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted phosphinate$_{(C0-C10)}$ has 0 to 10 carbon atoms. The groups, —P(O)(OH)H, —P(O)(OH)CH$_3$, —P(O)(OH)CH$_2$CH$_3$, —P(O)(OCH$_3$)CH$_3$, and —P(O)(OC$_6$H$_5$)H are non-limiting examples of heteroatom-unsubstituted phosphinate groups. The term "heteroatom-substituted phosphinate$_{(C_n)}$" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted phosphinate$_{(C0-C10)}$ has 0 to 10 carbon atoms.

As used herein, a "chiral auxiliary" refers to a removable chiral group that is capable of influencing the stereoselectivity of a reaction. Persons of skill in the art are familiar with such compounds, and many are commercially available.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use,* 2002), which is incorporated herein by reference.

An "isomer" of a first compound is a separate compound in which each molecule contains the same constituent atoms as the first compound, but where the configuration of those atoms in three dimensions differs.

A "stereoisomer" is an isomer in which the same atoms are bonded to the same other atoms, but where the configuration of those atoms in three dimensions differs.

"Enantiomers" are stereoisomers that are mirror images of each other, like left and right hands.

"Diastereomers" are stereoisomers that are not enantiomers.

Stem Cells

The term "pluripotent stem cell" refers to a cell capable of giving rise to cells of all three germinal layers, that is, endoderm, mesoderm and ectoderm. Although in theory a pluripotent cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming differentiated cells. In certain embodiments, the pluripotent stem cell is an embryonic stem cell derived by somatic cell nuclear transfer.

A "neural stem cell" is an undifferentiated cell from neural tissue that is capable of giving rise to more neural stem cells (i.e., exhibits self renewal) and to progeny cells that will terminally differentiate into neural cells. The neural stem cell can be an adult or embryonic neural stem cell.

In certain embodiments of the present invention, pluripotent stem cells and neural stem cells are exposed in vitro to a differentiation agent, resulting in the differentiation of the stem cells into neural precursor cells. A neural precursor cell is a cell that can generate neuronal cells (i.e. neurons or neuronal precursors) and glial cells (i.e., astrocytes, oligodendrocytes, or glial cell precursors), but cannot give rise to a pluripotent or neural stem cell.

Mammalian Embryonic Stem Cells

Mammalian embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

Depending on culture conditions, ES cells can produce colonies of differentiated cells or undifferentiated cells. The term "differentiate" means the progression of a cell down a developmental pathway. The term "differentiated" is a relative term describing a cell=s progression down a developmental pathway in comparison with another cell. For example, a pluripotent cell can give rise to any cell of the body, while a more differentiated cell such a hematopoetic cell will give rise to fewer cell types. As used herein, "undifferentiated ES cells" refers to ES cells that do not show the characteristics of more specialized cells.

Mouse and human ES cells can be maintained in an undifferentiated state by culturing the cells in the presence of serum and a feeder layer, typically mouse embryonic fibroblasts. Other methods for maintaining ES cells in an undifferentiated state are also known. For example, mouse ES cells can be maintained in an undifferentiated state by culturing in the presence of LIF without a feeder layer. However, unlike mouse ES cells, human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel or laminin, without a feeder layer and in the presence of fibroblast-conditioned medium plus basic fibroblast growth factor, (Xu et al., 2001; U.S. Pat. No. 6,833,269).

A pluripotent cell is capable of differentiating into any cell of the body. The pluripotency of ES cells has been determined in various ways (Martin, 1982). In one test, mouse ES cells derived from the inner cell mass of a blastocyst are injected into the cavity of another blastocyst. The injected blastocyst is deposited into the uterus of a pseudopregnant female mouse to produce progeny that are chimeras of injected and recipient blastocyst cells. In another test, mouse ES cells are injected into adult mice to produce tumors called teratomas. Such tumors can contain a variety of cell types derived from endoderm, mesoderm, and ectoderm. In certain embodiments, one or more treatoma-derived cells may be cultured or differentiated into neuronal or neuronal-committed cells according to the present invention. The pluripotency of human ES cells can also be tested by the formation of teratomas in immunodeficient mice. A third test is to alter culture conditions to allow ES cells to differentiate into more specialized cells. For example, mouse ES cells can spontaneously differentiate into various cell types by removing the feeder layer and adding LIF to the culture medium. Similarly, human ES cells can spontaneously differentiate by removing the feeder layer and growing the ES cells on a non-adherent surface in suspension (Itskovitz-Eldor et al., 2000; Reubinoff et al., 2000; Roach et al., 1993). Under such conditions, the ES cells can form cell aggregates called embryoid bodies which contain cells having characteristics of neurons and heart muscle cells. In all of these tests, the pleuripotency of ES cells is shown by their ability to generate cells of endoderm, mesoderm, and ectoderm origin.

Cultures of ES cells are described as "undifferentiated" when a substantial proportion of stem cells and their derivatives in the population display morphological characteristics of undifferentiated cells, clearly distinguishing them from differentiated cells of embryo or adult origin. Undifferentiated ES cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

ES cells can be characterized by the proteins they produce. For example, the following marker proteins have been used to characterize ES cells: stage-specific embryonic antigen SSEA-1, stage-specific embryonic antigen SSEA-3, stage-specific embryonic antigen SSEA-4, tumor rejection antigen-1-60 (TRA1-60), tumor rejection antigen-1-81 (TRA1-81), alkaline phosphatase (AP), and transcription factor Oct-4. As shown in Table 1, mouse, human and primate cells differ in their pattern of expression of these markers. For example, SSEA-1 is expressed in mouse ES cells, but not human or monkey ES cells, while TRA1-60 is expressed in human and monkey ES cells but not mouse ES cells.

TABLE 1

ES Cell Marker Expression

| Marker | Mouse | Human | Monkey |
|---|---|---|---|
| SSEA-1 | Yes | No | No |
| SSEA-2 | No | Yes | Yes |
| SSEQ-3 | No | Yes | Yes |
| TRA1-60 | No | Yes | Yes |
| TRA1-81 | No | Yes | Yes |
| AP | Yes | Yes | Yes |
| Oct-4 | Yes | Yes | Yes |

Methods for preparing and culturing ES cells can be found in standard textbooks and reviews in cell biology, tissue culture, and embryology, including Teratocarcinomas and embryonic stem cells: A practical approach (1987); Guide to Techniques in Mouse Development (1993); Embryonic Stem Cell Differentiation in Vitro (1993); Properties and uses of Embryonic Stem Cells: Prospects for Application to Human Biology and Gene Therapy (1998), all incorporated herein by reference.

Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct3/4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF. Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007, doi:10.1038/nature06357). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

Neural Stem Cells

Neural stem cells are undifferentiated cells from neural tissue that are capable of giving rise to neural stem cells (capable of self-renewal) or to cells that will terminally differentiate into neural cells. A neural stem cell can be an adult neural stem cell or an embryonic neural stem cell. As used herein, the term "adult" neural stem cell refers to stem cells derived from somatic tissue whether from an adult or a child.

Methods for isolating adult and embryonic neural stem cells from humans and other animals are well known (Rietze and Reynolds, 2006; Svendsen et al., 1999).

Differentiation of Stem Cells

In accordance with the present invention, exposure of undifferentiated mammalian pluripotent stem cells or neural stem cells in vitro to a differentiation agent of structure (I) results in the formation of neural precursor cells. To prepare neural precursor cells, the undifferentiated stem cells can be cultured for a time in the presence of the differentiation agent, then allowed to proliferate in the absence of the differentiation agent. Variations of this basic procedure are contemplated so long as the result of exposure to the differentiation agent is the differentiation of stem cells to neural precursor cells. For example, in a first step, undifferentiated stem cells can be cultured in suspension on a non-adherent surface in the presence of the differentiation agent. In a second step, after exposure of the stem cells to the differentiation agent for an appropriate amount time, the cells can be cultured in suspension on a non-adherent surface in the presence of the differentiation agent, with fresh culture medium. In a third step, the exposed cells can be plated and grown in the absence of the differentiation agent. Proliferating cells can be split and passaged when the cells reach about 80-90% confluency.

In the first step, the culture medium can be any medium that supports the survival and growth of pluripotent stem cells or neural stem cells. For example, the culture medium can be DMEM, RPMI 1640, GMEM, or neurobasal medium. The culture medium can contain serum, or can be a serum-free medium. The serum-free medium can be used without the addition of an exogenous growth factor, or can be supplemented with a growth factor such as basic fibroblast growth factor (bFGF), insulin-like growth factor-2 (IGF-2), epidermal growth factor (EGF), fibroblast growth factor 8 (FGF8), Sonic hedgehog (Shh), brain derived neurotrophic factor (BDNF), glial cell line-derived neurotrophic factor (GDNF), or Vitamin C. The non-adherent surface can be low-attachment tissue culture plastic.

As in the first step, the culture medium of the second step can be any medium that supports the growth of pluripotent stem cells or neural stem cells. The medium can contain serum, or can be a serum-free medium with or without the addition of a growth factor. Similarly, the cells can be grown in suspension on a non-adherent tissue culture surface.

In the third step, exposed cells can be plated on an adherent surface in culture medium containing serum, in serum-free culture medium without a growth factor, or in serum-free culture medium containing a growth factor such as bFGF, IGF-2, EGF, FGF8, Shh, BDNF, GDNF, or Vitamin C. The adherent surface can be tissue culture plastic, or can be a coated tissue culture surface such as a tissue culture plate coated with polyornithine/laminin, bovine collagen I, human extracellular extract, porcine skin gelatin or Matrigel. Cells can be passaged when they reach confluency, 80-90% confluency, or at any other level of confluency. Either aggregates of cells, single cell suspensions, or both, can be plated. To prepare cells for passaging, cells can be mechanically removed from adherent surfaces, for example by pipetting, or chemically removed by treatment with a protease such as trypsin-EDTA, collagenase or dispase.

All possible combinations of the first, second and third steps are contemplated. For example, in one procedure, the first step involves the use of serum-free medium without a growth factor, while the second and third steps involve the use of serum-free medium with a growth factor. In another procedure, all three steps involve the use of serum-free medium with a growth factor. In other procedures, the first and second steps are combined such that cells are exposed to the differentiation agent without a change in culture medium before being plated in the third step.

Effective concentrations of a differentiation agent can be determined by a dose-response analysis. The differentiation agent can be dissolved in a solvent such as dimethyl sulfoxide (DMSO), then added at various concentrations to ES cell cultures. The extent of differentiation of ES cell cultures after exposure to different amounts of the differentiation agent can be determined by measuring the expression of promoters, genes and proteins active in neural precursor cells and/or neuronal cells. For example, expression of the Tα-1 promoter, the β3-tubulin gene and protein, the nestin gene and protein, the double-cortin gene and protein, the vimentin gene and protein, the NeuN gene and protein, or the MAP2 gene and protein can be analyzed. A typical range of concentrations for the dose-response analysis are 100 nM to 100:M of the differentiation agent.

Differentiated cells prepared by exposure of undifferentiated stem cells to the differentiation agent can be characterized morphologically, immunochemically and in other ways to confirm their status as neural precursor cells.

Neural Precursor Cells, Neuronal Cells and Glial Cells

Neural cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Certain cells embodied in this invention have morphological features characteristic of neuronal cells or glial cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells. Markers of interest include but are not limited to: a) β3-tubulin, microtubule-associated protein 2 (MAP-2), or neurofilament, characteristic of neurons; b) glial fibrillary acidic protein (GFAP), present in astrocytes; c) 2',3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax 6 and nestin, characteristic of neural precursors and other cells; f) Sox 1, characteristic of developing central nervous system; g) tyrosine hydroxylase (TH), present in catecholamine neurons; h) glutamic acid decarboxylase, isoform 67 (GAD67), present in neurons containing gamma-aminobutyric acid; and i) vimentin, characteristic of intermediate neuronal differentiation.

Tissue-specific markers listed in this disclosure and known in the art can be detected using any suitable immunological technique, such as flow immunocytochemistry and fluorescence activated cell sorting for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Antibody binding to an antigen can be observed by standard immunocytochemistry or flow cytometry assay, after fixation of the cells, using a labeled secondary antibody or other conjugate (such as a biotin-avidin conjugate) to amplify labeling, or other immunological methods well known in the art. In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference.

The expression of tissue-specific gene products can also be detected at the mRNA level by Northern blot analysis or dot-blot hybridization analysis, or by reverse transcriptase initiated polymerase chain reaction (RT-PCR) using sequence-specific primers in standard amplification methods which are described in detail in U.S. Pat. Nos. 4,683,195, 4,683,202 and 4,800,159, and in Innis et al., 1988, each of which is incorporated herein by reference in their entirety. Sequence data for the particular markers listed in this disclosure can be obtained from public databases, such as Gen-BANK. Expression of tissue-specific markers as detected at the protein or mRNA level is considered positive if the level is at least 2-fold, and preferably more than 10- or 50-fold above that of a control cell, such as an undifferentiated ES cell.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

Homogeneous and Synchronized Cell Populations

A culture of neural precursor cells prepared by exposing pluripotent stem cells or neural stem cells to a differentiation agent of the present invention can comprise a homogeneous or nearly homogeneous population of neural precursor cells. As used herein, a "nearly homogeneous" population contains at least about 95% neural precursor cells as determined by analyzing the expression of neural cell markers. Part of the mechanism for generating homogeneous or nearly homogeneous cell populations can involve the elimination of undifferentiated cells and non-neural cells from the cell culture following exposure to the differentiation agent.

A culture of neural precursor cells prepared by exposing pluripotent stem cells or neural stem cells to a differentiation agent of the present invention can comprise a population of neural precursor cells synchronized or nearly synchronized at a particular developmental stage. As used herein, a "nearly synchronized" population contains at least about 95% neural precursor cells at a particular developmental stage. The proportion of neural precursor cells and the stage of development can be determined by analyzing the expression of stage specific neuronal precursor cell markers.

Cell Survival

In another aspect of the present invention, mammalian neural precursor cells are treated in vitro with an active agent to increase neural precursor cell survival over that which would occur in the absence of the active agent. The active agent is a compound having the structure (I) described herein. In preferred embodiments, $Z_1$ and $Z_2$ are both carbon triply bonded to each other. In other preferred embodiments, $Z_1$ and $Z_2$ are both nitrogen doubly bonded to each other.

Preferably, the active agent is: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

Because the active agent has the same structure as the differentiation agent described herein, mammalian neural precursor cells can be prepared by exposing undifferentiated mammalian pluripotent stem cells or neural stem cells to the active agent, and then allowing the cells to differentiate into neural precursor cells. Neural precursor cell populations prepared in this way can show increased cell survival as compared to control pluripotent or neural stem cells not exposed to the active agent.

In addition, neural precursor cells can be prepared in other ways. For example, neural precursor cells can be obtained from brain tissue (Johansson et al., 1999), or prepared by coculturing ES cells with murine bone marrow feeder cells (Perrier et al, 2004). Neural precursor cells can also be obtained from cultures of adult or embryonic neural stem cells (Rietze and Reynolds, 2006). A neural precursor cell prepared by any method can be exposed to the active agent to enhance survival of the precursor cell.

Neurons, Astrocytes and Oligodendrocytes

In another aspect, the present invention provides a method of preparing neuronal cells in vitro by exposing undifferentiated pluripotent stem cells or neural stem cells to the differentiation agent of structure (I), then culturing the exposed cells in the absence of the differentiation agent. Under appropriate conditions, the exposed cells differentiate into neurons, astrocytes and/or oligodendrocytes. In preferred embodiments, $Z_1$ and $Z_2$ are both carbon triply bonded to each other. In other preferred embodiments, $Z_1$ and $Z_2$ are both nitrogen doubly bonded to each other.

Preferably, the differentiation agent is: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl)diazenylpyridine-2,6-diamine; 3-[(2-methyl-1,3-thiazol-4-yl)ethynyl]pyridine (MTEP); a physiologically acceptable salt thereof; or any combination thereof.

Conditions for exposing undifferentiated pluripotent stem cells or neural stem cells to the differentiation agent, and for culturing exposed cells in the absence of the differentiation agent, are describe herein. Differentiation into neuronal and glial cells can be determined by the morphology of the differentiated cells, the expression of neuronal and glial cell markers in the differentiated cells, and the electrophysiological functioning of differentiated neuronal cells.

Methods for Screening Test Compounds and Assessing Toxicity

The present invention further comprises methods for evaluating the toxicity of a test compound in neuronal or neuronally committed cells which have been cultured and/or differentiated according to the present invention. These assays may comprise testing a single test compound or random screening of large libraries of candidate substances; alternatively, the assays may be used to focus on particular classes of compounds selected with an eye towards structural attributes that are believed to make them more likely to modulate the function of neurons or neuronally-committed cells. In certain embodiments, the toxicity of a test compound may be evaluated by contacting the compound with a plurality of neuronal or neuronally-committed cells, such as cells which have formed into an engineered neural tissue (ENTs) (e.g., derived from human embryonic stem cells. ENTs are 3-dimensional pieces of tissues derived from embryonic stem cells (ES) which resemble certain layers of human fetal brain which may be produced via the differentiation of cells according to the present invention. The toxicity testing may be utilized as a part of an in vitro drug-screening process, e.g., prior to the clinical administration of the test compound to a subject, such as a human patient.

Various attributes may be evaluated to determine if a test compound results in toxicity in cells of the central nervous system. Parameters including, for example, cell death (necrosis, apoptosis) excitotoxicity, cytotoxicity, altered neuronal function (e.g., altered generation of action potentials or long-term potentiation, etc.), altered brain receptor function, decreased resistance to challenge with a known toxic compound, synaptic toxicity, developmental neurotoxicity, or neural lineage-specific toxicity (e.g., in oligodendrocytes, astrocytes, or dopaminergic neurons) may be assessed in the cells to determine if a test compound results in toxicity or neurotoxicity. Electrophysiological techniques may be used to detect neuronal activity or function. Measure of synaptic markers may be used to detect compounds with a synaptic toxicity. Cells may be engineered to contain a promoter specific for a defined lineage (e.g., oligodendrocytes, dopaminergic neurons etc.) controlling the expression a reporter gene, such as a luminescent or fluorescent protein; in this way, neural lineage-specific toxicities may be more easily observed by changes in the expression of the reporter gene in vitro. In certain embodiments, reactive oxygen species may be measured to determine if a test compound results in increased cellular oxidative stress. In certain embodiments, dose-response relationships may be generated to assess the toxicity of a test compound. In certain embodiments, developmental neurotoxicity may be assessed by incubating a test compound cells during neural differentiation.

Multiple compounds or part or all of a small molecule library may be screened for toxicity or neuronal activity in cells cultured according to the present invention. Some or essentially all of the neuronal or neuronal-committed cells may be further differentiated into dopaminergic cells prior to the assessment of the toxicity of a test compound; this may be particularly useful in instances where it may be desirable to understand the dopaminergic toxicity of a compound.

The culturing and/or toxicity testing methods of the present invention may be automated. In certain embodiments, one or more of the steps involved with culturing cells, differentiating cells, and/or evaluating the a property (e.g., the toxicity) of a test compound may be automated, e.g., via the use of robotics, to facilitate high-throughput toxicity assessment in cells. For example, various robotics may be used to culture cells, add or remove media from the cells, add a test compound to media comprising neuronal or neuronally-committed cells differentiated according to the present invention. Specific robotics which may be used with the methods of the present invention include cell dispensers that allow automated and standardized distribution of cells in multiwells which typically range from 12 to 384 wells although a higher or lower number of wells can be used as desired (e.g., Matrix WellMate™ from Thermo Fisher Scientific, Inc.) and multichannel liquid handlers that allow automated distribution of library compounds into multiwell plates and automated dilutions of compounds, e.g., for $IC_{50}$ calculations (e.g., Zephyr from Caliper Life Sciences).

To assess the toxicity of a compound, one generally will determine the function and/or viability of cells in the presence and absence of the test compound. For example, a method generally comprises:

(a) providing a test compound;
(b) admixing the test compound with an isolated cell, plurality of cells, or one or more ENTs which have been cultured and/or differentiated according to the present invention;
(c) measuring whether or not the candidate modulator can alter or disrupt cell viability or function in the cell or cells in step (c); and
(d) comparing the characteristic measured in step (c) with the characteristic of the cell or cells in the absence of said candidate modulator,
wherein a difference between the measured characteristics indicates that said candidate modulator affects or exhibits toxicity against the cell or cells.

Screening may be carried out in a high-throughput assay using one or more multi-well plates, such as a 96 well plate. For example, ENTs may be produced in multi-well plates in order to establish a screening platforms to study the neurotoxic potential of a test compound (e.g., a small molecule, protein, peptide, antibody, putative therapeutic) or multiple compounds (e.g., from a compound bank, small molecule library, peptide library, antibody library, etc.). Test compounds may be synthetically produced or purified from natural sources. Methods for producing ENTs and/or evaluating the properties of a test compound may be automated; for example, steps of adding or removing a compound or solution to a multi-well plate, detecting luminescence or fluorescence in a multi-well plate, and/or producing ENTs in a multi-well plate may be automated, e.g., via robotics.

In various embodiments, combinations of test compounds may be evaluated to determine if the simultaneous or sequential application of 2, 3, 4, 5, 6, or more test compounds to a neural or neuronally-committed tissue results in a particular effect or toxicity. The sequential administration of multiple compounds to a tissue may vary from seconds to hours, weeks, or longer, as desired. For example, in such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several weeks (1, 2, 3, 4, 5, 6, 7 or 8) lapse between the respective administrations. Various combinations may be employed between test compound "A" and test compound "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

In other embodiments, test compounds may be separately contacted with different neural or neuronally-committed tissue(s).

Because differentiation agents of the present invention, such as phenazopyridin, can strongly promote ENTs formation, resulting ENTs may be tested for toxicity and may serve as a suitable in vitro model for toxicity testing on the human brain. The complex networks of neurons typically present in ENTs can resemble the human fetal brain in many aspects and thus may represent a more accurate model of the human brain which may be used for in vitro testing, such as evaluation of the neurotoxicity of a test compound. These methods may be a particularly tool for industry and drug development and/or for screening compounds for possible neurotoxicity.

Compounds of the present invention, such as phenazopyridin, can also improve the quality of ENTs and decrease the occurrence of contaminating non-neural tissues. As shown in further detail in the Examples, phenazopyridin has been systematically used by the inventors to produce ENTs. These methods may be utilized in large scale ENT production.

In certain embodiments ENTs may be engineered to include a neural-specific promoter coupled to a luminescent or fluorescent protein (e.g., GFP, eGFP, EBFP, EBFP2, Azurite, mKalama1, ECFP, Cerulean, CyPet, YFP, Citrine, Venus, YPet, Firefly luciferase, Renilla luciferase). In this way, the cellular identity and viability may be optically detected, e.g., via a microscope and/or automated optical detection method (e.g., fluorescent activated cell sorting or FACS). In the presence of a neurotoxic compound, decreased expression or of the luminescent protein in culture, such as an ENT, could be used to identify due to the death of neuronal or neuronally committed cells. Thus, as compared to a control tissue, increases or decreases in expression of a marker or "tag" protein (e.g., a spectrophotometrically detectable or enzymatic protein) may be used to identify compounds which promote or reduce neuronal survival.

Specific neuronal promoters which may be used for this purpose include, for example, the Tα1 α-tubulin promoter (Tα1) and the βIII-tubulin promoter. Various promoters for specific neuronal lineages may be used to evaluate responses in specific cell types, including, e.g., dopaminergic neuron-specific promoters (e.g., tyrosine hydroxylase promoter), synapse-specific promoters (e.g., synapsin I promoter), axon-specific promoters (e.g., MAP2 promoter), and non-neuronal-specific promoters (e.g., oligodendrocytes assessed by CNPase II promoter). The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

In certain embodiments a pluripotent stem cell may be transfected with a dual reporter system to detect differentiation of the stem cell into a neuronal or neuronally-committed cell. The dual reporter system may utilize a neuron-specific promoter to express a first luminescent or fluorescent protein and a second promoter (e.g., a promoter expressed by all cells or by a second cell type) can drive the expression of a second luminescent or fluorescent protein. In this way, the relative expression of neuronal markers may be observed. A reporter system may be transfected into a pluripotent cell via a variety of techniques including, e.g., liposomal transfection, microparticle bombardment, or viral transfection such as lentiviral transfection. In the below examples, a dual reporter system is used to observe expression of Firefly luciferase via the Tα1 promoter and Renilla luciferase via the EF1-α short promoter (EF1-αS).

Fluorescent proteins generally comprise a fluorescent chromophore, the chromophore being formed from at least 3 amino acids and typically characterized by a cyclization reaction creating a p-hydroxybenzylidene-imidazolidinone chromophore. The chromophore may not contain a prosthetic group and is capable of emitting light of selective energy, the energy having been stored in the chromophore by previous illumination from an outside light source comprising the correct wavelength(s). Spontaneously fluorescent proteins can vary widely in structure and the number of amino acids present in a chromophore, provided that the chromophore comprises the p-hydroxybenzylidene-imidazolidinone ring structure. In some instances, a fluorescent protein may comprise a β-barrel structure such as that found in green fluorescent proteins and described in Chalfie et al. (1994). Fluorescent proteins typically exhibit the ability to emit, in response to an incident light of a particular wavelength absorbed by the protein, a light of longer wavelength. Fluorescent activated cell sorting or (FACS) may be used to detect the expression of one or more neuron-specific markers in certain embodiments. FACS products are available, e.g., FACSCalibur™ (Becton Dickson) which may be used with the present invention.

Test compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other test compounds include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors. Peptidomimetics of peptide modulators or other compounds which are sterically similar to pharmacologically active compounds may also serve as test compounds.

It will, of course, be understood that all the screening methods of the present invention are useful in themselves notwithstanding the fact that toxicity or some other property may or may not be observed in a test compound.

Treatment of Nervous System Damage

In another aspect, the present invention provides a method of treating nervous system damage, comprising administering to a patient in need of such treatment an effective amount of a pyridine derivative of structure (I). In some embodiments, $Z_1$ and $Z_2$ are both carbon triply bonded to each other. In other embodiments, $Z_1$ and $Z_2$ are both nitrogen doubly bonded to each other.

The pyridine derivatives for treatment are preferably one or more of the following: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any combination thereof.

In some embodiments, the pyridine derivate of structure (I) does not include one or more of the following: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl) diazenylpyridine-2,6-diamine; 3-[(2-methyl-1,3-thiazol-4-yl)ethynyl]pyridine (MTEP); or a physiologically acceptable salt thereof. In other embodiments, the pyridine derivative of structure (I) does not include any derivative where $Z_1$ and $Z_2$ are both carbon triply bonded to each other.

The nervous system damage can be due to a neurodegenerative disorder or a nervous system injury. Neurodegenerative disorders include diseases such as Alzheimer's disease, frontotemporal dementia, dementia with Lewy bodies, amyotrophic lateral sclerosis (Lou Gehrig's disease), Parkinson's disease, Huntington's disease and multiple sclerosis. Nervous system injury includes injury due to ischemic cerebral stroke, spinal cord lesions, brain injury, post-hypovolemic and hypotensive brain damage (including post-operative brain damage), post-infectious complications (including post-meningitis hypocampus degeneration, brain parenchyma damage after abscesses and herpes simplex encephalitis). In essence, the pyridine derivatives of the present invention can be used to treat any nervous system damage that results from loss or injury of neural or glial cells.

With regard to treatment of a patient, an "effective amount" of a pyridine derivative of the present invention, or a pharmaceutical composition containing a pyridine derivative of the present invention, is an amount sufficient to produce newly formed neural cells in the damaged region of the nervous system.

During treatment, adult neural stem cells are exposed to the administered pyridine derivative. The pyridine derivative can act in various ways on the adult neural stem cells. For example, the pyridine derivative can act on the adult neural stem cells located in a patient's nervous system to cause differentiation of the adult neural stem cells into neural precursor cells, neurons, glial cells, astrocytes or oligodendrocytes. In some embodiments, the pyridine derivative can stimulate the proliferation of adult neural stem cells, radial glial cells, neuroepithelial cells or other neural precursor cells. Similar actions have been proposed for other factors that enhance the proliferation and differentiation of neural cells, such as interferon gamma (Kim et al., 2007), leukemia inhibitory factor (Bauer et al., 2006), TGF-alpha (Fallon et al., 2000). By enhancing proliferation and/or differentiation of neural cells in the damaged area of the nervous system, the treatments of the present invention may lead to regeneration of neurons and recovery of nervous system function.

A. Pharmaceutical Formulations

Pharmaceutical compositions and formulations of the pyridine derivatives can be administered by direct injection into damaged areas of the nervous system, or administered parenterally, intravenously, intradermally, intramuscularly, transdermally, intraperitoneally, intrathecally, or per os.

For injection, solutions of the active compounds as free base or pharmacologically acceptable salts can be prepared, for example, in water, glycerol, liquid polyethylene glycols, and mixtures thereof and in oils, to form a solution or suspension. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like. Methods of preparing formulations will be apparent to those skilled in the art (for example, see Remington's Pharmaceutical Sciences" 15th Edition).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared B. Administration For treatment of nervous system damage, adult neural stem cells are exposed to a pyridine derivative of the present invention. The routes of administration will vary, naturally, with the location and nature of the damage, and include, e.g., intradermal, transdermal, parenteral, intravenous, intramuscular, intranasal, subcutaneous, percutaneous, intratracheal, intraperitoneal, perfusion, lavage, direct injection, and oral administration and formulation.

The pyridine derivative can be given in a single dose, or multiple doses. Continuous administration also may be applied where appropriate. Generally, the dose of a therapeutic composition via continuous perfusion will be equivalent to that given by a single or multiple injections, adjusted over a period of time during which the perfusion occurs. The amount of pyridine derivative administered will be dependent on the subject being treated, the subject's weight, the manner of administration, and the judgment of the physician. Treatment regimens may vary as well, and often depend on the type of nervous system damage, location of the damage, disease progression, and health and age of the patient.

In some embodiments, a phenazopyridine or another pyridine derivative of the present invention is administered to a patient systemically or by local injection. Systemic administration can be by intravenous or intraperitoneal delivery. The pyridine derivative can be administered to reach a circulating level of about 2 to 20 mg/ml in blood, or a dose of about 100-300 mg can be delivered to a patient.

Differentiation Compounds

In another aspect, the present invention provides a method of directing the differentiation of pluripotent stem cells or neural stem cells to neural cells in vitro by exposing undifferentiated pluripotent stem cells or neural stem cells to an effective amount of a differentiation compound of structure (I) under conditions sufficient to enhance differentiation of the embryonic stem cells to neural cells as compared to differentiation under similar conditions without the differentiation compound. In some embodiments, $Z_1$ and $Z_2$ are both carbon triply bonded to each other. In other embodiments, $Z_1$ and $Z_2$ are both nitrogen doubly bonded to each other.

Preferably, the active agent is: phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No. 7,660,000); phenyldiazenylpyridin-2-amine; 3-(4-chlorophenyl)diazenylpyridine-2,6-diamine; 3-(2-chlorophenyl)diazenylpyridine-2,6-diamine; 3-[(2-methyl-1,3-thiazol-4-yl)ethynyl]pyridine (MTEP); a physiologically acceptable salt thereof or any combination thereof.

The term "neural cells" includes neural precursor cells, neuronal precursor cells, glial precursor cells, neurons, astrocytes and oligodendocytes.

SIB 1893 has the following structure:

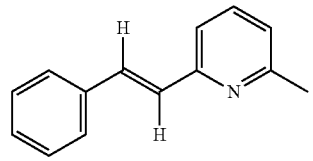

SIB 1757 has the following structure:

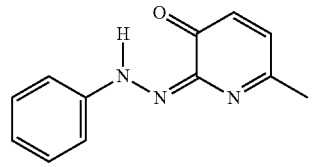 [SMILES: CC1=N/C(=N/Nc2ccccc2)C(=O)C=C1]

NSC41777 has the following structure:

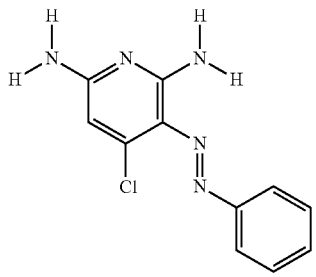

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

3-Dimensional Cultures

An aspect of the present invention relates to the culture of tissues which preferably display several features of fetal neural tissues. When evaluating neural differentiation using embryonic stem cells (ESC), it is generally desirable to mimic as closely as possible physiological cellular interactions involved in neurogenesis. As described herein, methods involving air/liquid interface-based cultures of human ESC are provided. These methods may involve exposing a tissue to a differentiation agent, such as phenazopyridine. Nonetheless, this culture system can allow for three-dimensional cell expansion and neural differentiation in the absence of added growth factors. In certain embodiments, culture methods such as those described in Eiraku et al. (2008), which is incorporated by reference in its entirety, may be used with the present invention.

As shown in the below examples, over a three month period, a macroscopically visible compact tissue was cultured. Histological examination revealed a dense neural-like neural tissue including immature tubular structures. Electron microscopy, immunochemistry and electrophysiological recordings demonstrated a dense network of neurons, astrocytes and oligodendrocytes able to propagate signals. Within this tissue, tubular structures were niches of cells resembling germinal layers of human fetal brain. Indeed, abundant proliferating cells expressing markers of neural progenitors were observed. The capacity to generate neural tissues on air/liquid interface displayed some variability for different ESC lines, confirming variations of neurogenic potential between cell lines. These approaches demonstrate the in vitro engineering of a human neural-like tissue with an organization similar to an early developing brain. These methods may provide advantages over previously used methods, as these methods: (i) allow or promote three-dimensional organization of cells in tissues, (ii) yield dense interconnected neural tissue with structurally and functionally distinct areas, and (iii) is spontaneously guided by endogenous developmental cues.

Undifferentiated ESC may be cultured via the following protocol. ESC cells (e.g., line H1, H9, HS-401) may be maintained in 80% DMEM/F12, 20% KnockOut-Serum Replacement, 2 mM L-glutamine, 1% non-essential amino acids, 0.1 mM β-mercaptoethanol, 4 ng/ml bFGF. Mouse embryonic fibroblasts may be used as feeders and isolated from embryos (e.g., of pregnant CF-1 mice). Human Foreskin Fibroblasts may be used as feeders in various embodiments. Fibroblasts may be cultured in DMEM, 10% fetal bovine serum and 1% penicillin/streptomycin. Feeders may be mitotically inactivated by irradiation (40 Gy) before seeding on a gelatin-coated plate.

Isolation of Gliomaspheres may be isolated via the following protocol. Viable fragments of high grade human glioblastoma may be transferred to a beaker containing 0.25% trypsin in 0.1 mM EDTA (4:1), and slowly stirred at 37° C. for 30-60 min. Dissociated cells may be plated in 75 cm$^2$ tissue culture flasks (at about 2500-5000 cells/cm$^2$) in DMEMF-12 medium (1:1) containing the N2, G5 and B27 supplements (available from Invitrogen). After a delay ranging from about 2 to 47 days, spheres may bloom from clusters of adherent cells and detach in the medium.

ESC-derived neural progenitor cells (NPC) induction may be performed via the following protocol. For a feeder-dependant method, a stromal cell line (e.g., MS5) may be maintained in αMEM (Invitrogen) containing 10% fetal bovine serum and 2 mM L-glutamine. NPC differentiation may be induced by co-culture with MS5. Five to ten clusters may be plated on a confluent layer of irradiated (50 Gy) MS5 in DMEM, 15% Knockout serum replacement (Invitrogen), 2 mM L-glutamine, 10 µM β-mercaptoethanol and 1% penicillin/streptomycin. After about 2 weeks, cultures may be switched for two additional weeks to N2 medium (DMEM with 4.5 g/l glucose, N2 supplement (Gibco), 10 ng/ml bFGF and 1% penicillin/streptomycin).

ESC may also be induced to NPC in feeder-independent conditions. Small ESC aggregates may be induced in neural induction medium (DMEMF12, N2-supplement (Gibco) and 1% penicillin) for about 4 days. Aggregates may then be plated on polyornithin 0.01%, laminin (1 µg/ml)-coated dishes containing neural induction medium.

Air/liquid interface expansion/differentiation of NPC may be performed via the following protocol. One or more rosettes-enriched clusters may be manually removed and multiple clusters (e.g., about 5-10 clusters) may be plated on a hydrophilic polytetrafluoroethylene (PTFE) membrane (e.g., 6 mm diameter, 0.4 µm, BioCell-Interface, La Chaux-de-Fonds, Switzerland). This membrane may be deposited on a Millicell®-CM (0.4 µm) Culture Plate Insert (Millipore) (FIG. 5A). N2 medium may preferably be added (e.g., about 1 ml) underneath the membrane insert.

Neural differentiation of ESC in two dimensions may be utilized in certain embodiments. Neural spheres may be generated via the following protocol: ESC may be detached with type IV collagenase (e.g., 1 mg/ml) and cultured in suspension, e.g., in ultra low attachment plates (Costar) for three weeks in neural induction medium Neural differentiation in adherent conditions may be performed using the following protocol: 4 days neural spheres may be plated at low density on 1 µg/ml laminin-coated plates. After one week, rosette-enriched clusters may be detached and dissociated with trypsin/EDTA before re-plating at low density on laminin in neural differentiation medium (neurobasal supplemented with B-27 and 10 µg/ml human recombinant BDNF).

A. Air/Liquid Interface Culture and Differentiation without Exogenous Factors

Air/liquid interface culture was originally developed for organotypic culture of brain slices and shown to retain many of their essential organizational features (Stoppini et al., 1991). The inventors demonstrate below that the technique can be adapted to perform three dimensional expansion/differentiation of human ESC-derived NPC. An important feature of the air/liquid interface culture is the improved exchange between air and tissue, allowing the development of a relatively thick three dimensional culture without hypoxic cell death. In contrast with most of the previously described differentiation protocols (Joannides et al., 2007; Nat et al., 2007; Perrier et al., 2004; Schulz and Noggle, 2004; Yan et al., 2005), the three-dimensional simplified method using ESC aggregates obtained in minimal conditions did not require exogenously added differentiating factors. Indeed, addition of FGF-2 or EGF did not induce phenotypic changes although a moderate increase of the size of engineered tissue was observed. In addition, Noggin, a polypeptide playing a key role in neural induction, had no influence on the self-organization and phenotype of air/liquid interface-induced tissue. Thus, these methods can favour spontaneous events driving the maintenance of NPC with mature neural cells.

The coexistence of proliferating stem cell niches and differentiated tissue in cultures provided, in certain embodiments and as performed in the below examples, the surprising result that the proliferating areas do not invade the mature tissue (e.g., as observed for 4 months). This observation suggests that endogenous cues regulate the stemness of germinal niches as well as their ability to generate a mature neuronal tissue. Thus, as observed in vivo, this method may allow spontaneous thin regulatory mechanisms associating at the same time germinal centers and mature cells.

B. Expansion Versus Differentiation Using Air/Liquid Interface Conditions

Differences exist between NPC expansion and neuronal/glial differentiation. Previous reports demonstrated the expansion of NPC as well as their differentiation into neurons and glia. However, although NPC, neurons, and glia normally co-exist in culture, different culture conditions may favour expansion rather than differentiation (or the contrary). Air/liquid interface culture of NPC in a minimal medium can favour neuronal/glial differentiation, associating in the same culture permanent niches of highly neurogenic NPC and highly mature or differentiated neuronal tissue.

C. The Role of Oxygen

Oxygen changes appear to have complex but poorly understood effects on precursor cell fate. In vitro studies on fetal precursors are typically performed in a non-physiological oxygen tension (20%). By comparison, lowered oxygen in the physiological range (<5%) has been shown to increase the expansion of NPCs (Storch et al., 2001; Studer et al., 2000). Conversely, lowered oxygen was described to prevent neuronal differentiation of rat neural progenitor cells (Gustafsson et al., 2005). Air/liquid interface is a distinct system where a small film or nanofilm of medium covers the tissue favouring extensive gas exchanges between tissue and air. NeuN and especially synaptophysin were predominantly expressed in cells in the below examples near the air side. Without wishing to be bound by any theory, these results support the idea that normoxia may favour the survival and/or differentiation of mature neuronal cells.

D. Fetal Brain vs. ESC-Derived Brain-Like Tissue

As shown in the below examples, similarities were observed between the fetal brain and the tissues obtained in vitro. The in vitro-generated tissue substantially reproduced the following spatial dynamics of neurogenesis: radial organization, proliferating precursors in distinct germinal centers, and production of differentiating neuroblasts which migrate away from the luminal regions towards apical mature zones. As observed in fetal brain, the mature regions form a real parenchyma with abundant intermingled neurites was observed. Expression of synaptophysin and markers of synaptic neurotransmitters demonstrate that the below-cultured differentiated neurons express the molecular machinery that is required for synaptic transmission.

Similarities between the tubular areas shown in the obtained tissue and the developing ventricular wall of the fetal brain were also observed, particularly with respect to the radial organization of the nestin- and vimentin-containing filaments. The BLBP, nestin- and vimentin-containing cells resembled in some respects radial glia. The time frame of appearance of glial cells also displayed similarities with fetal brain development. Indeed, in normal fetal brain development of neurons precedes that of astrocytes (Merkle and Alvarez-Buylla, 2006). Similarly, the appearance of GFAP-positive astrocytes was observed, at earliest, after two months of tissue formation. Immature oligodendrocyte were observed to be present after one month of tissue formation; however, myelinization was still absent after two months. Given the relatively short time for differentiation of the three-dimensional tissue, this is may not be surprising as myelinization occurs only after 22 weeks in fetal brain.

Certain differences were observed between developing fetal brain and the three dimensional culture, including the presence of some apoptosis within the tubes. Such apoptotic cells were not observed in the fetal brain. Without wishing to be bound by any theory, this apoptosis might be a peculiarity of the culture system, which might limit the expansion of the germinative centers. However, alternative explanations might also explain this finding; for example, microglia/macrophages, which are absent in the engineered tissue but present in the brain parenchyma as of the fourth month development, might rapidly remove the zone of apoptotic cells in the fetal brain (Rezaieand Male, 1999; Mallat et al., 2005). The establishment of the anterior to posterior and the dorsal to ventral axes, which is observed in normal fetal brain development, was not observed in these studies. Although a set of positional markers were found, it is likely that the positional identity (Roussa and Krieglstein, 2004) is not respected by the process, and no spatial specification of defined neuronal subtypes groups was observed.

E. The Differences Between ESC Lines.

In agreement with other studies (Osafune et al., 2008; Wu et al., 2007; Allegrucci and Young, 2007), the results supported the idea that ESC lines do not share identical capacity to generate neural cells. These differences do not appear to result from chromosomal abnormalities since karyotypes were normal for the three tested lines. Without wishing to be bound by any theory, the following explanations may explain some of the observations: i) different epigenetic modifications, possibly due to different techniques of derivation and maintenance culture or due to heterogeneity of cells from the inner cell mass yielding ES cells with different properties, ii) genetic modifications (e.g., point mutations) that are not accompanied by karyotype changes, or iii) the genetic heterogeneity of the human population as compared to the homogeneity of inbred mouse strains [34].

An aspect of the present invention thus relates to the engineering of three dimensional human nervous tissues from human embryonic stem cells. The system preferably relies on spontaneous differentiation cues and can imitate in space in time certain steps involved in early fetal brain development. These methods may thus be used to study early events of human neurogenesis and/or produce tissues which may be used to evaluate the pharmacology or toxicology of a test compound.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention

Example 1

Materials and Methods

Reagents

Reagents and their sources were as follows: the murine CGR8 embryonic stem cell line (European Collection of Cell Culture); the human H1 embryonic stem cell line (Wicell Research Institute Inc.); the stromal bone marrow MS5 cell line was provided by Katsuhiko Itoh (Itoh et al., 1989); cell culture media, fetal bovine serum, serum replacement, penicillin, streptomycin, N2 supplement, non-essential amino acids, sodium pyruvate, collagenase IV (Gibco, Paisley, Scotland); basic human fibroblast growth factor (Invitrogen corp.); recombinant brain derived neurotrophic factor (Sigma-Aldrich); L-Polyornithine, human laminin (Sigma-Aldrich). Antibodies and their sources were as follows: mouse anti-CNPase II, rabbit anti-Musashi, rabbit anti-nestin, mouse anti-Vglut-1, mouse anti-vimentin, rabbit anti-SOX-1, rabbit anti-tyrosine hydroxylase (Chemicon), mouse anti-Pax6 (Developmental studies Hybridoma bank); goat anti-double-cortin (Santa Cruz); rabbit anti-glial fibrillary acidic protein (GFAP) (Dako); mouse anti-βIII-tubulin (Sigma); rabbit anti-βIII-tubulin (Covance). The following fluorochrome-labeled secondary antibodies were used: AlexaFluor (555, 488 or 350)-labeled antibodies from goat or donkey against mouse, goat or rabbit (Invitrogen-Molecular probes). The sources of small organic molecules were as follows: NINDS custom collection II; phenazopyridine hydrochloride, daidzein (Microsource Discovery inc.); DFB, MSOP, CPPG, PHCCC, L-AP4 (Tocris); MTEP (Alexis corporation); Harmine, SIB1893, SIB1757, MPEP (Sigma-Aldrich).

Cell Cultures

The human H1 ES cell line was maintained in DMEM/F-12 medium supplemented with 20% serum replacement, L-glutamine, non-essential amino acids, and 4 ng/ml human basic fibroblast growth factor; H1 cells were cultured on irradiated mouse embryonic fibroblasts using standard techniques. Examples of such techniques can be found at the WiCell Research Institute web site (on the World Wide Web at wicell.org).

Immunofluorescence Microscopy

Immunofluorescence was carried out according to standard techniques. In brief, mouse ES cells were grown on glass coverslips coated polyornithin in six-well plates, and human ES cells were grown on plastic or glass coverslips coated with laminin/polyornithin in six-well plates. Cells were fixed with 2% paraformaldehyde for 30 min, washed with HBSS and permeabilized with 0.5% (v/v) Triton X-100 for 30 min. Cells were then exposed to primary antibodies overnight at 4° C. After two washes in HBSS containing 1% serum (blocking buffer), cells were stained with secondary antibodies at RT for 1 h (1:1000 dilution in blocking buffer). Cell nuclei were stained with 1 μg/ml 4'-6-Diamidino-2-phenylindole (DAPI) for 10 min. Pictures were taken on an ImageXpress Micro (Molecular Devices) or a Zeiss axioplan microscope equipped for epifluorescence.

Immunostaining Quantification

Immunostaining and nuclear staining quantifications were performed using the MetaXpress software (Molecular devices). Total neurite outgrowth was quantified using the neurite outgrowth analysis module, and total cell numbers were quantified with the count nuclei analysis module.

Quantitative Analysis of Cells Expressing Fluorescent Proteins

Fluorescence intensity in a given cell was quantified using the Metamorph® software.

Example 2

Differentiation of Human ES Cells to Neural Precursor Cells

Methods

Undifferentiated human H1 ES cells were cultured on irradiated mouse embryonic fibroblasts (MEF). To carry out neuronal differentiation, ES cells were mechanically dissociated into small aggregates (50-300 cells) and cultured in suspension on low-attachment six-well plates. For the first 4 days, the cells were cultured in neuronal induction medium (DMEM F-12 (Gibco), N2 supplement (Gibco), penicillin and streptomycin (Gibco), phenazopyridine 3:M). Then the medium was changed to simple neuronal proliferation medium (DMEM F-12, N2 supplement, 20 ng/ml human recombinant bFGF, penicillin and streptomycin, phenazopyridine 3:M) for 2 additional days. Subsequently, 15-20 6-day old cell aggregates were plated on polyornithine/laminin-coated six-well plates and maintained in simple neuronal proliferation medium for 7 days. Cells were then mechanically dissociated and replated in N2 medium (DMEM high glucose (Gibco), 10 ng/ml human recombinant bFGF (Gibco), N2 supplement (Gibco), penicillin and streptomycin (Gibco)) at a density of 20,000 cells per $cm^2$ on polyornithine/laminin-coated six-well plate. Cells were passaged when they reached 80-90% confluency, and were maintained in the same culture conditions for 2 additional weeks. Stock phenazopyridine (Microsource Discovery Inc.) was prepared by diluting phenazopyridine powder in DMSO (Sigma-Aldrich) at a concentration of 6 mM. The stock solution was diluted at 1:2000 in cell culture media to obtain a final concentration of 3:M Each of the components of the neuronal induction medium, the simple neuronal proliferation medium and the N2 medium can be replaced with clinical grade equivalents. Therefore, the foregoing procedure of carrying out neuronal differentiation is referred to herein as the "clinical grade protocol."

To prepare polyornithine/laminin-coated plates, six-well tissue culture plates were incubated for 45 minutes in a 0.0015% polyornithine solution diluted in sterile MiliQ water, washed twice with sterile MiliQ water, then incubated for 2-24 hours in a 1: g/ml solution of human recombinant laminin. The plates were then washed twice with sterile MiliQ water and three times with PBS. A 0.01% Polyornithine solution and human recombinant laminin were bought from Sigma-Aldrich.

Results

The effects of phenazopyridine on ES cell differentiation were investigated using the clinical grade-compatible protocol. The first step involved generation of spheres of cells grown in suspension for 6 days, followed by replating on polyornithine/laminin coated plastic. One week later, cells were passaged at $2 \times 10^4$ cells/$cm^2$ on polyornithine/laminin coated plastic, and during the following two weeks cells were passaged when they reached 80-90% confluency. Cells were treated with either DMSO (1:2000) or with phenazopyridine (PAP) at 3:M with equivalent final DMSO concentration throughout the 4 week period. FIG. 1 shows representative phase contrast pictures of human ES cells at different stages of differentiation. No apparent difference was observed after one week of differentiation between DMSO-treated spheres and phenazopyridine-treated spheres (FIGS. 1A and 1E). At two weeks of differentiation, control spheres remained relatively compact (FIG. 1B), whereas phenazopyridine-treated spheres developed into big areas of monolayer surrounding the plated spheres (FIG. 1F). After mechanical passaging, cells remained as aggregates in control cells (FIGS. 1C and 1D) as compared to phenazopyridine-treated cells (FIGS. 1G and 1H), which could easily be dissociated into single cells. There was a marked difference between the percentages of living single cells in control cells compared to phenazopyridine-treated cells when cells were passaged at different timepoints throughout the procedure (FIG. 1I), an indication that phenazopyridine promotes survival of dissociated cells.

Example 3

Phenotype of Control and Phenazopyridine-Treated Cells

The phenotype of control and phenazopyridine-treated cells was investigated through immunostaining for various neuronal markers after four weeks of differentiation. Immunostaining was performed for nestin, β3-tubulin, Sox1, Pax6, vimentin, GFAP and Musashi. Control-treated cells were mainly present as clusters. The clusters often contained typical rosette areas positive for nestin and β3-tubulin, but clusters negative for both markers were also observed. Musashi, Pax6, Sox 1, vimentin and GFAP were distributed heterogeneously. In contrast, phenazopyridine-treated cells were mainly present as isolated cells, with very few small clusters. Cells displayed a homogeneous distribution of most markers investigated, with the exception of few strongly β3-tubulin-positive cells, and some GFAP-positive cells. Virtually all cells were nestin, Sox 1 and vimentin-positive, expressed β3-tubulin and Pax6 at low levels, and were negative for musashi.

Example 4

Exposure of ES cells to Phenazopyridine Enhances Neuronal Differentiation

To investigate the potential of neural precursors generated through phenazopyridine treatment, cells exposed to DMSO or phenazopyridine for four weeks as in Example 2 were replated at low density ($5 \times 10^3$ cells/cm$^2$) on polyornithine/laminin coated support in neuronal differentiation medium, and investigated for their phenotype at different time points. Cells were then immunostained for neuronal markers and alkaline phosphatase (marking undifferentiated ES cells) after one week and four weeks of differentiation. Immunostaining was performed for nestin, β3-tubulin, Sox1, Pax6, vimentin, GFAP, CNPase, v-Glut1, GAD67, tyrosine hydroxylase and alkaline phosphatase. After one week of differentiation, control-treated cells developed into large neuronal networks, but other areas contained tightly packed neuronal precursors with few differentiating neurons, and a few isolated cells positive for Sox 1 and occasionally for Pax6. The monolayer of phenazopyridine-treated neural precursors started to differentiate into neurons. Subtypes of neurons included mainly glutamatergic, GABAergic and rarely dopaminergic neurons. After 4 weeks of differentiation, control-treated cells still contained cells at variable differentiation stages. Sox1 and Pax6 positive-cells, alkaline phosphatase-positive cells, large areas of rosettes stained for β3-tubulin positive cells at the periphery, and areas of well-developed neuronal networks coexisted in the same culture. In contrast, phenazopyridine-treated cells formed networks of neurons, astrocytes and oligodendrocytes, but also formed slow-growing clusters homogeneously positive for nestin, β3-tubulin, Sox1 and vimentin, with occasional mature neurons. Upon trypsinization of these structures, cells were able to generate neurons and astrocytes, indicative of cells representing a multipotent progenitor population. These results indicate that phenazopyridine treatment increases the homogeneity of the neural progenitor population to generate a homogeneous population of multipotent neural progenitors.

Example 5

Phenazopyridine Increases the Quality of Engineered Neural Tissues

Phenazopyridine (3 µM) substantially increased the quality of engineered neural tissues (ENTs) derived from human embryonic stem cells. ENTs are 3-dimensional pieces of tissues derived from embryonic stem cells (ES) which resemble certain layers of human fetal brain.

Figure 2:
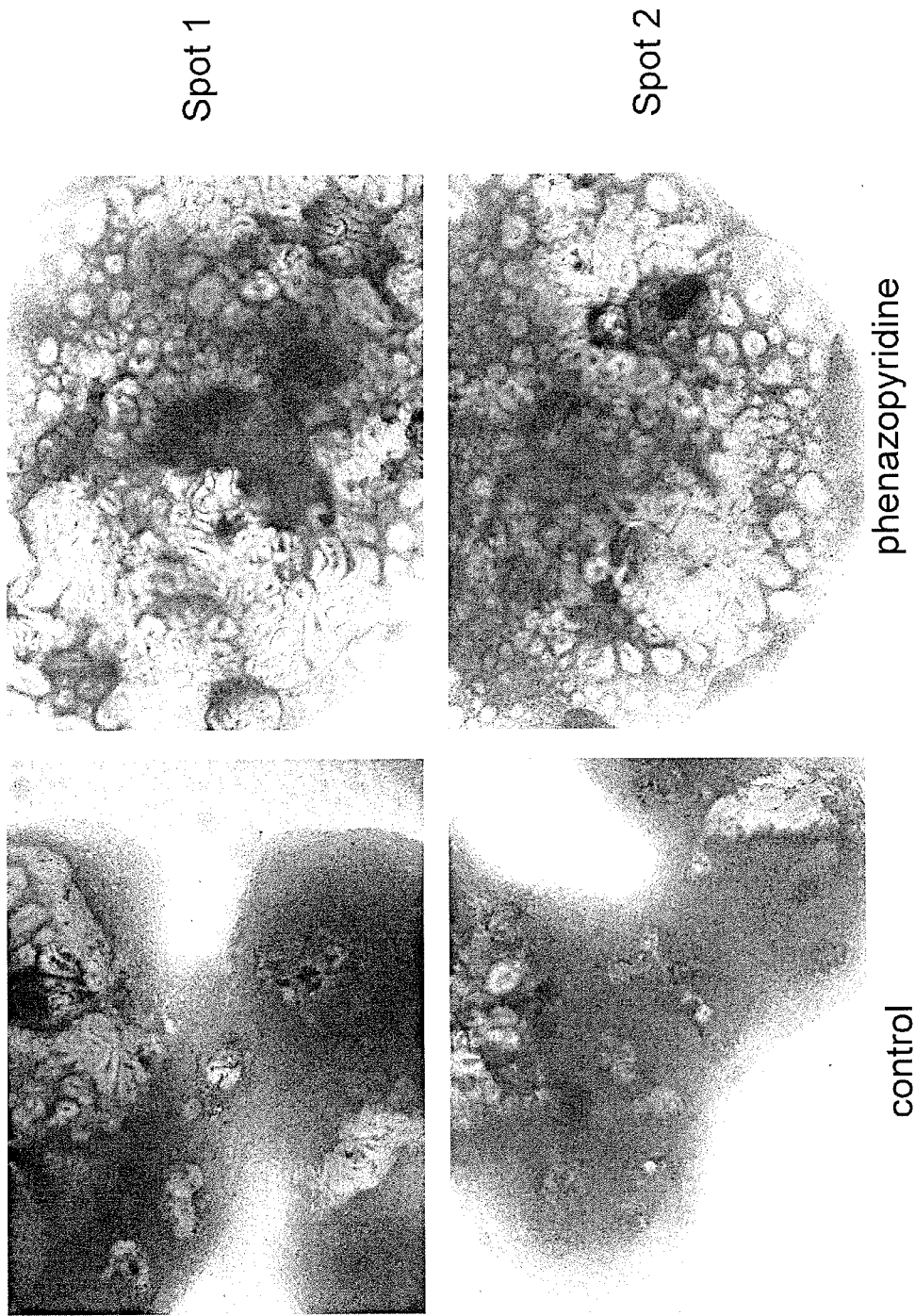
FIG. 2: A panel of photographs showing that phenazopyridine increases rosette formation in ENTs. 1 month old ENTs engineered with or without phenazopyridine are shown, and improved densities of rosettes were observed in cultures containing phenazopyridine.

Phenazopyridine increased the number of rosettes during the first steps of ENT formation. Rosettes are round tubular structures classically observed during the in vitro neural differentiation of stem cells. Rosettes include highly neurogenic neural stem cells. One of the main interests of ENTs is the presence of such rosettes within a dense neuronal and astroglial network which provides an integrated and organized tissue which associates with both germinatives neural stem cell niches (rosettes) and mature neural tissue. Phenazopyridine thus displays significant improvements in the presence of rosettes. FIG. 2 compares a ENT (1 month age) engineered with or without phenazopyridine, and improved densities of rosettes were observed in cultures containing phenazopyridine.

Phenazopyridine also decreased the incidence of cells differentiating into non-neuronal cells within ENT, thus reducing contamination of ENTs with non-neural tissue. In the absence of Phenazopyridine, the differentiation of ES into non-neural tissues was observed, thus contaminating ENTs. Specifically, dark pigmented tissues, possibly containing skin and or retinal cells, and immature mesenchyma which appeared to differentiate into cartilage were observed. FIG. 3 shows a macroscopic view of ENTs grown in the presence or absence of phenazopyridin. Exposure to phenazopridine resulted in ENT which were more homogenous and appeared to contain a reduced amount of non-neural cells; specifically, ENTs treated with phenazopridine displayed less mesenchyma (FIG. 3) and fewer dark pigmented zones.

FIG. 4 shows staining for the presence or absence of the cartilage marker tenascin C in ENTs grown in the presence or absence of phenazopyridine. As shown in FIG. 4, cartilage was not observed in ENTs grown in the presence of phenazopyridine based on immunofluorescent staining of tenascin C.

Phenazopyridine was used to increase the number and purity of neural stem cells in cultures. It is anticipated that these methods may be advantageously used in multiple applications, including the production of neural stem cells for immunogenicity studies, as well as the production of dopaminergic neurons for possible use in stem cell therapies of Parkinson's disease.

Example 6

Development of Human Nervous Tissue Upon Differentiation of Embryonic Stem Cells in Three Dimensional Culture Given the complexity of the central nervous system (CNS), the study of human brain development is a major challenge, which can only partially be addressed by extrapolation from animal experiments. Direct functional studies of human brain development are extremely difficult because of ethical reasons. Thus, relevant in vitro models of human brain development are needed. The potential of human ESC to provide such models has been readily recognized, however so far studies have focused on cellular development and not on tissue formation.

During embryogenesis, the CNS develops from neural progenitor cells (NPC) within the ectodermal germ layer. NPC are specified in space and time, becoming heterogeneous and generating a progressively restricted repertoire of mature neural cell subtypes (Merkle and Alvarez-Buylla, 2006). The CNS originates as a sheet of cells made up of primary NPC, also referred as neuroepithelial cells. The latter forms the neural tube, easily discernable in humans by the end of the third week of gestation (Stern, 2005; Wilson and Edlund, 2001). The evolving neural tube is a germinative center containing NPC that self-renew and produce both neurons and glia. The neural tube germinative activity progressively decreases during development, the latter being replaced by the ventricular system and spinal canal. Low amounts of NPC persist into the adult brain in the subventricular zone and the subgranular zone of the dentate gyms in the hippocampus (Gould, 2007).

NPC in the evolving neural tube are radially oriented and contact both the apical (ventricular) and basal surfaces (Merkle and Alvarez-Buylla, 2006). During brain development, they divide symmetrically or asymmetrically at the ventricular surface, forming a germinative center that produces radially neurons and glia (Haubensak et al., 2004). By the onset of neurogenesis, neuroepithelial cells are progressively replaced by radial glial cells (Anthony et al., 2004). Radial glial cells divide in the evolving ventricular zone and produce neurons and glia (Gotz et al., 2002; Malatesta et al., 2003).

NPC can be derived in vitro from ESC and can be expanded in the presence of growth factors such as bFGF, EGF or LIF. Subsequently they can be differentiated towards mature neurons, astrocytes or oligodendrocytes through treatment with externally added factors (Cho et al., 2008; Elkabetz et al., 2008; Joannides et al., 2007; Joannides et al., 2007; Nat et al., 2007; Perrier et al., 2004; Schulz et al., 2004; Yan et al., 2005). A fraction of ESC-derived NPC spontaneously organize in vitro into rosettes, these neurogenic structures (Elkabetz et al., 2008) being suggested to share some similarities with the neural tube. However, with techniques applied so far, differentiation of NPC does not lead to a dense neuronal tissue, but rather grow as highly heterogeneous neural cell cultures.

The below studies demonstrate that in vitro expansion/differentiation of human ESC-derived NPC using air/liquid interface system allows generation of an organized three-dimensional neural tissue. This tissue presents surprising and substantial phenotypic and structural similarities with the early developing human fetal brain.

Material and Methods

Culture of undifferentiated ESC. ESC cell line H1 and H9 were from WiCell Research Institute (Madison, Wis.), HS-401 cell line was provided from Dr Outi Hovatta, Karolinska Institute, Sweden). H1 and H9 were maintained in 80% DMEM/F12, 20% KnockOut-Serum Replacement, 2 mM L-glutamine, 1% non-essential amino acids, 0.1 mM β-mercaptoethanol, 4 ng/ml bFGF. Mouse embryonic fibroblasts were used as feeders and isolated from embryos of pregnant CF-1 mice (Charles River Laboratories, Wilmington, Mass.). Human Foreskin Fibroblasts were used as feeders for HS-401 and were from ATCC (CCL-110, Manassas, Va., USA). Fibroblasts were cultured in DMEM, 10% fetal bovine serum and 1% penicillin/streptomycin. Feeders were mitotically inactivated by irradiation (40 Gy) before seeding on a gelatin-coated plate.

Isolation of Gliomaspheres. Viable fragments of high grade human glioblastoma were transferred to a beaker containing 0.25% trypsin in 0.1 mM EDTA (4:1), and slowly stirred at 37° C. for 30-60 min. Dissociated cells were plated in 75 $cm^2$ tissue culture flasks plated at 2500-5000 cells/$cm^2$) in DMEMF-12 medium (1:1) containing the N2, G5 and B27 supplements (all from Invitrogen). After a delay ranging from 2 to 47 days, spheres bloomed from clusters of adherent cells and detached in the medium.

ESC-derived NPC induction. For the feeder-dependant method, MS5 stromal cell line (provided by Dr Katsuhiko Itoh, Kyoto University, Japan) (Itoh et al., 1989) were maintained in αMEM (Invitrogen) containing 10% fetal bovine serum and 2 mM L-glutamine. NPC differentiation was induced by co-culture with MS5. Five to ten clusters were plated on a confluent layer of irradiated (50 Gy) MS5 in DMEM, 15% Knockout serum replacement (Invitrogen), 2 mM L-glutamine, 10 μM β-mercaptoethanol and 1% penicillin/streptomycin. After 2 weeks, cultures were switched for two additional weeks to N2 medium (DMEM with 4.5 g/l glucose, N2 supplement (Gibco), bFGF (Invitrogen) 10 ng/ml and 1% penicillin/streptomycin).

ESC were also induced to NPC in feeder-independent conditions. Small ESC aggregates were induced in neural induction medium (DMEMF12, N2-supplement (Gibco) and 1% penicillin) during 4 days. Aggregates were then plated on polyornithin 0.01%, laminin (1 μg/ml)-coated dishes containing neural induction medium.

Air/liquid interface expansion/differentiation of NPC. Rosettes-enriched cluster were manually removed and 5-10 clusters were plated on a hydrophilic polytetrafluoroethylene (PTFE) membrane (6 mm diameter, 0.4 μm, BioCell-Interface, La Chaux-de-Fonds, Switzerland). This membrane was deposited on a Millicell®-CM (0.4 μm) Culture Plate Insert (Millipore) (FIG. 1). One ml of N2 medium was added underneath the membrane insert.

Neural differentiation of ESC in two dimensions. Generation of neural spheres: ESC were detached with type IV collagenase (1 mg/ml) and cultured in suspension in ultra low attachment plates (Costar) for three weeks in neural induction medium Neural differentiation in adherent conditions: 4 days neural spheres were plated at low density on 1 μg/ml laminin-coated plates. After one week, rosette-enriched clusters were detached and dissociated with trypsin/EDTA before re-plating at low density on laminin in neural differentiation medium (neurobasal supplemented with B-27 (all from Gibco) and 10 μg/ml human recombinant BDNF (RnD systems)).

Immunofluorescence. Samples were fixed in PBS-4% paraformaldehyde for 30 min at room temperature, dehydrated and embedded in paraffin. The sections (10 μm) were then deparaffined and rehydrated, heated in citrate buffer (0.01M; pH 6.0) within 620 W microwave oven for 15 min. The sections were then incubated overnight at +4° C. with appropriate dilutions of primary antibodies in PBS containing 0.2% Triton X-100 and 10% serum from the species corresponding to the secondary antibody. After washing in PBS, sections were incubated in PBS-0.2% Triton X-100 for 1 h30 at room temperature with appropriate dilution of secondary antibody, washed again and incubated with DAPI 300 nM for 15 minutes. Sections were finally washed in PBS, rinsed with water before mounting in Fluor Save® medium (Calbiochem). For fetal brains analysis, the brains of human aborted fetuses were obtained from the Neuropathology Unit, in accordance with the institutional ethic comity.

Real Time PCR. Real time PCR were performed on different old stage samples. Reactions were run on an ABI Prism 7900 HT detection system (Applied Biosystems). ALAS and GusB were used as housekeeping genes. As these genes behaved similarly in all samples examined, data was normalized to ALAS level. Sequences of the primers are described in supplementary Table I.

Electrophysiological Recordings. Samples were transferred to a multi-electrode array system and maintained at 33° C. The tissues were positioned so that their different regions were in contact with electrodes. Evoked field potentials could be recorded as described (Thiebaud et al., 1997; van Vliet et al., 2007).

Transmission electron microscopy. Fixation of the membrane-associated tissue was performed by incubation in 3% glutaraldehyde for 2 hour. The fixed tissue was washed 3 times with PBS, dehydrated in ethanol, embedded in epoxy resin and processed for electron microscopy as described previously (Foti et al., 1997). Sections were contrasted with uranyl acetate and lead citrate and observed with a Technai 20 electron microscope (FEI, Eindhoven, Netherlands).

Antibodies. The following primary antibodies against human antigens were used: rabbit anti-cleaved caspase-3 (Cell Signaling), mouse anti CNPase II, rabbit anti Musashi, mouse anti myelin oligodendrocyte specific protein, rabbit anti nestin, mouse anti neuronal nuclei specific protein (NeuN), mouse anti VGlut-1, mouse anti vimentin, rabbit anti Sox-1, mouse anti synaptophysin, rabbit anti tyrosine hydroxylase (all from Chemicon), goat anti Pax-6, goat anti double-cortin (all from Santa Cruz), mouse anti PCNA, rabbit anti GFAP (all from Dako), mouse anti βIII-tubulin (Sigma), rabbit anti βIII-tubulin (Covance). The following fluorochrome-labeled secondary antibodies were used: AlexaFluor (555 or 488)-labeled antibodies from goat or donkey against mouse, goat or rabbit (Invitrogen-Molecular probes).

Results

ESC-derived neural progenitor cells (NPC) expand on air/liquid interface cell culture system. ESC-derived NPC were either induced by feeder or feeder-independent conditions (FIG. 5A). The two methods allowed rosette clusters formation after one month (FIG. 5B). These rosettes consisted mainly of cells expressing NPC markers such as nestin, Sox-1, Musashi-1 and Pax-6. The inventors proceeded them towards an air-liquid interface culture system of rosette-clusters, similarly to that previously used for tissue explants (Stoppini et al., 1991). For that purpose, clusters were manually isolated and plated on pre-cut patches of hydrophilic PTFE membranes before deposition on culture insert (FIG. 5A). By adding the culture medium only underneath the insert, the clusters were covered by capillarity by a very thin film of medium, allowing important air diffusion. One week after insert plating, neuroepithelial clusters had increased in size. FIG. 1C shows a culture that consisted initially of four plated clusters that grew and merged within one week. After one month in culture, most of the initial cell clusters had merged, generating a compact cellular mass, covering the membrane, with numerous newly formed rosettes (FIG. 5D).

To investigate whether the method could be further simplified, early ESC aggregates were obtained using a minimal neural induction medium (FIG. 5E). Such aggregates were only deposited on the membrane (FIG. 5F). After two days, they merged (FIG. 5G) and, after one month, developed into a cell mass (FIG. 5H, I).

NPC cultured on air/liquid interface develop into a three dimensional tissue. Cell masses obtained by the three different methods were processed for histological investigation. In the case of feeder-induced NPC, hemalun/eosin staining showed cells organized in a three dimensional tissue-like structure. The tissue was heterogeneous since immature mesenchymal zones and dark pigmented zones could be observed within the cell mass. Feeder-free induced rosettes or directly-plated ESC aggregates generated tissues with significantly less mesenchymal and dark pigmented zones. Higher magnification revealed regions with distinct histological features. First, there were tubular structures including radially-oriented cells. Their dense nuclear staining and weaker cytoplasmic staining suggested immature structures. Second, there were more mature zones devoid of organization, with less nuclear, but more pronounced cytoplasmic staining.

Other sources of NPC were also tested in their ability to generate a tissue using air/liquid interface cell culture system. Neurospheres including progenitors that were isolated from gliomas developed into a dense three-dimensional tissue. However, no organization was observed.

Air/liquid interface culture induces a neural tissue including germinative niches of NPC. The phenotype of cells forming the tubes obtained in the liquid/air interphase culture was first analyzed in detail. Many cells of the tube walls expressed the Proliferation Cell Nuclear Antigen (PCNA), indicative of their mitotic activity. In contrast, mature zones contained few PCNA-positive cells. The radially-organized cells forming the tubes were positive for molecules expressed in NPC: nestin, Musashi-1. Note the radial organization of nestin-expressing filaments inside the tube walls. Pax-6 was the most documented transcription factor involved in neurogenesis and found to be expressed in the germinal layer of human developing fetal brain (Bayatti et al., 2007; Mo and Zecevic, 2007). Pax-6 was expressed in all cells forming tubes, confirming a NPC identity of such structures. Sox-1 was found either in tubes and cells outside the tubes (few PCNA staining). Cells within tubes co-expressed Pax-band Sox-1. Cells of the tube expressed also the intermediate filament vimentin, but not the astrocytic protein GFAP. BLBP was observed in proliferating cells as well as filament around tubes. In the developing mouse CNS, this protein has been correlated with neuronal differentiation in many parts of the mouse CNS and studies showed that BLBP is transiently expressed in radial glia in the embryonic VZ (Feng et al., 1994).

Together, these observations strongly suggest a proliferating NPC identity for cells within tubular structures. Such NPC resemble early rather than late fetal or adult brain NPC in-as-much as they do not express astrocytic markers (Merkle and Alvarez-Buylla, 2006).

The nature of the tissue around tubes was next investigated. It was constituted of cells expressing the neuronal marker βIII-tubulin. The post-mitotic cells being adjacent to tubes expressed the neuroblast marker double-cortin, but not PCNA. The neuronal nature of such cells was confirmed by electron microscopy, showing densely packed neurites.

Strikingly, cells expressing the astrocytic markers GFAP were observed earliest after 2 month NPC culture. This delayed expression is reminiscent of the in vivo situation[1]. Moreover, the early oligodendrocyte marker CNPase II was expressed, suggesting the presence of immature oligodendrocytes within the differentiated tissue. In addition, coloration of tissue sections with Luxol Blue and Bielchowski methods did not show any myelinization process.

Some cells distant from tubes expressed NeuN and synaptophysin which are indicative of mature stage of neuronal development. The glutamatergic and cholinergic nature of neurons was evidenced by immunostaining of vesicular neurotransmitter transporters VGlut1 (glutamate) and VAchT (acetylcholine). Few tyrosine hydroxylase-positive neurons were observed, indicating that dopaminergic and/or other catecholaminergic neurons were rare. The presence of mature neurons establishing connections was suggested by electron microscopy observation of structures resembling synapses and the ability of the tissue to receive and propagate electrical signals. Indeed, successive electrical stimulations (2V, 200 μsec) with 50 ms or 10 ms interval induced the propagation of an electrical signal that is typical of a group of neurons. It is noteworthy that the reduced propagation intensity after a short interval (10 ms) indicated a paired-pulse inhibition process, suggesting the presence of a negative regulatory loop.

To confirm the neural phenotype of the ESC-derived tissue, expression of genes involved in early brain development was analyzed 2 weeks and four weeks after plating on the insert. The pluripotency marker Oct-4 decreased upon air-liquid interface differentiation, while, genes indicative of neural development increased, including Pax-6, Pax-2, Pax-7, HoxB4, Nkx6.1, Olig-2, MAP-2, Sox-1 and Mash-1. Note the anterior, midbrain, posterior identity of Pax-6, Pax-2 and HoxB4, respectively and that Pax-7 is indicative for a dorsal identity. Mash-1 is a forebrain marker. The mesodermal marker Meox-1 increased upon differentiation probably accounted for by the observed regions of mesenchymal appearance. Olig2 which is indicative of oligodendrocytes lineage increased also upon differentiation. However, differentiation toward radial glia-like progenitors was also suggested by this increase of Olig2 expression. Expression of the endodermal AFP was found to be maintained. In contrast, the glial marker GFAP, the early mesodermal brachyury, the myelin-binding protein expressed by mature oligodendrocytes and the endodermal Sox-17 were detected at very low level. Together, these observations confirm the neural identity but exclude organization according the positional identity along the dorso-ventral or antero-posterior axes.

Expression of the used markers in human fetal brain. With the ultimate goal to compare the in-vitro induced tissue with the in-vivo situation, the expression the neural markers described above was investigated in human fetal brain. Coronal sections at the level of the human periventricular germinal layer at different developmental stages (from 12 to 34 weeks), including the adjacent cortical layers were immuno-stained. Ventricular (VZ) and subventricular zones (SVZ) were characterized by a high density of immature cells with a strong nuclear and a weak cytoplasmic staining Adjacent there was the subplate (SP) including migrating young neuroblasts, with a lower density of nuclei and a more pronounced cytoplasmic staining Neurons in the cortical plate (CP) could be localized at 12 and 14 weeks stage. Germinal layers were clearly distinct from the other cortical layers at later stages. Results for all immunostainings at each stage are summarized in supplementary table I. As expected, cells of the germinal layer expressed the proliferation marker PCNA (e.g., 12 weeks) and the neuroepithelial marker nestin (e.g., 12 weeks). Note the radial organization of nestin expression close to the ventricle similarly to that observed in tubular structures. In fetal brain, the expression of Musashi-1 was strictly restricted to germinal layers as it was restricted to the germinal niches of ESC-derived tissue. Sox-1, that was found in and outside germinal niches, was predominantly detected in nuclei of cells of the CP, even though some cells of the SP were also positive (e.g., 12 weeks). Note that βIII-tubulin was outside germinative layers, being expressed as expected in SP and upper layers (e.g., 22 weeks). Such distinction between germinal and maturing layers was also observed in the induced tissue. Similarly, double-cortin immunoreactivity (Quinones-Hinojosa et al., 2006) was restricted to the SP (e.g., 12 weeks), being absent in germinal and other layers.

NPC are known to progressively generate astrocytes upon brain development as seen by GFAP expression in late stage fetal brain and adult SVZ (Quinones-Hinojosa et al., 2006; Garcia et al., 2004; Doetsch et al., 1999). In accordance with these previously-described observations, expression of the GFAP was delayed. Indeed, GFAP was only weakly detected in germinative layers at week 14 whereas late fetal stage (weeks 22, 34) showed a strong increase of the protein expression in the VZ. Similarly to GFAP, the expression of vimentin was delayed in the VZ, being observed only at week 34. In comparison, the absence of GFAP in germinal niches of the ESC-derived tissue suggests structures corresponding to early developmental stages, although the expression of vimentin does not correlate with the in vivo situation. Together, these observations reveal some phenotypic similarities between ESC-induced neural tissue and early fetal brain, especially at the interface between germinal and young migrating neuroblasts layers.

Differences between differentiation on air/liquid interface culture as compared to two dimension methods in cell culture dishes. In vitro neural differentiation of ESC has been performed in numerous studies. The air/liquid interface method was compared with previously published studies. Globally, two kinds of methods were described: (i) neural differentiation of adherent cells (ii) neural differentiation in suspension (Elkabetz et al., 2008; Nat et al., 2007; Perrier et al., 2004; Lee et al., 2007; Lee et al., 2007; Sonntag et al., 2007; Vazin et al., 2008; Yang et al., 2008). In the case of neural differentiation in adherent conditions, cells grew and differentiate as mono- or paucilayers on feeder cells or substrate-coated plastic, inducing NPC that spontaneously organize into rosette and non-rosette structures. The cells included in rosettes are neuroepithelial NPC with a high neurogenic potential (Elkabetz et al., 2008). On the other hand, neural differentiation in suspension was shown to be efficient to obtain NPC and neurons inside three-dimension clusters called "embryoid bodies", "spheres" or "aggregates" (Cho et al., 2008; Joannides and Webber, 2007; Nat et al., 2007).

Expansion/differentiation of NPC on air/liquid interface shared some characteristics with previously published methods (self-organization of NPC into rosettes, a neuroepithelial phenotype, and mature neurons at the periphery of rosettes). However, the air/liquid interface-based method had unique properties that were not previously described:

(i) The number of rosettes for one air/liquid interface-derived tissue (Sup. FIG. 3A) was found to be significantly higher than that observed for one sphere in suspension.

(ii) Neural differentiation in suspension induced highly heterogeneous spheres in term of size and neurogenic potential. Indeed, some small spheres were found to resemble air/liquid interface-induced tissue: rosettes of neuroepithelial cells (nestin+) included into a dense tissue of mature neurons (βIII-tubulin+). However, such structures were rare (<10%) and mixed together with numerous other kinds of spheres including non-neural tubular structures that (nestin-) and few neurons, as well as spheres without any neural features (nestin-, βIII-tubulin-). Moreover, astrocytes and the expression of synaptophysin and double-cortin were not found within the small areas of neurons. In contrast, air/liquid interface culture was a more reproducible method providing a tissue rich in NPC rosettes within a mature neural tissue.

(iii) The heterogeneity of cell cultures is also a major feature of neural differentiation in adherent conditions. In addition to the absence of synchronization between cells starting/stopping differentiation, multiple types of structures resulted from spatial organization of cells. The following structures coexisted in culture during neuronal differentiation: rosettes aggregates, monolayer of flat cells with a NPC phenotype, floating spheres that spontaneously re-organize, neuronal scaffolds that are mixed with flat cells and aggregates. Immunofluorescent staining confirmed that neurons (βIII-tubulin +) were detected predominantly as dispersed cells that are intermingled with NPC (nestin +) apparently in a random fashion. In contrast, the air/liquid conditions favors compartmentalization between the two subpopulations, providing a more organized structure with a clear distinction between NPC niches and a dense neuronal network.

Table I summarizes the differences between air liquid interface and both adherent/non adherent previously described conditions for in vitro neural differentiation. In certain embodiments, it may be desirable to use pluripotent cells which result in the greater expression of a certain neural phenotype; for example, in embodiments where rosettes are preferably produced in a tissue, pluripotent cells such as H1 or H9 cells may be preferentially used as compared to HS-401 cells.

2007), this new system confirms the idea that ESC lines do not share identical capacity to generate neural cells. Finally, ESC-derived NPC were compared with that derived from adult glioma. Gliomaspheres differentiated on air/liquid interface culture induced a dense tissue including nestin and βIII-tubulin positive cells. In this case, nestin positive NPC versus βIII-tubulin positive neurons were mixed together without apparently organized structures. Note that the low organization of gliomaspheres-derived tissue was confirmed using GFAP, vimentin and PCNA staining.

Example 7

Phenazopyridine Induces and Synchronizes Neuronal Differentiation of Embryonic Stem Cells Embryonic stem (ES) cells are powerful tools to understand mechanisms of neuronal differentiation and to engineer neurons for in vitro studies and cell therapy. The inventors developed a screening approach to identify small organic molecules driving neuronal differentiation of ES cells. For this purpose, a lentivector carrying a dual luciferase reporter

TABLE I comparison between conventional and air/liquid interface methods for neuroal differentiation of human embryonic stem cells

| | | conventional method (H1 cell line) | | | air/liquid interface | |
|---|---|---|---|---|---|---|---|
| | | adherent cultures | spheres (one week) | spheres (two weeks) | H1 | HS-401 | H9 |
| cell organization in three dimensions | | +/− | +++ | +++ | +++ | ++ | +++ |
| presence of rosettes | | + | + | + | +++ | +/− | +++ |
| heterogeneity | | +++ | +++ | +++ | + | − | + |
| immunoreactivity | nestin | ++ | ++ | ++ | +++ | ++ | +++ |
| | βIII-tubulin | + | + | + | +++ | + | +++ |
| | Pax-6 | ++ | ++ | ++ | ++ | − | ++ |
| | Sox-1 | ++ | ++ | ++ | ++ | − | ++ |
| | GFAP | + | − | − | +/− | + | +/− |
| | PCNA | + | + | + | + | + | + |
| | double cortin | +/− | − | − | + | − | ++ |
| | vimentin | + | + | + | ++ | + | ++ |
| | synaptophysin | +/− | − | − | +++ | − | +++ |
| dense neuronal tissue | | − | − | + | +++ | − | +++ |
| astrocytes within neuronal tissue | | − | − | − | + | − | + |
| segregation between niches and neuronal tissue | | + | − | + | +++ | − | +++ |
| presence of non-neural cells | | + | ++ | ++ | + | +++ | ++ |

Different ESC lines do not share the same capacity to generate a neural tissue under air/liquid interface conditions. The following ESC lines were compared for their ability to be differentiated using air/liquid interface system: H1, HS-401 and H9. Each step of culture as well as the phenotype of structures within the tissue were compared and observations are summarized in table I. H9-derived spheres plated on the membrane provided a similar tissue than that observed for H1 in term of cell organization and phenotype (Table I). Stained sections from a H9-derived tissue where proliferating tubes (PCNA+) were distinct from a network of young migrating neuroblasts (double cortin+). In contrast, HS-401 differed from H1 and H9. HS-401-derived spheres were able to grew and merge on the membrane giving a tissue in three dimensions. However, the number of rosettes observed within the cell was dramatically low. Cells within the tissue did not organize in tubes and were immunoreactive for nestin and vimentin. No mature neurons expressing βIII-tubulin were observed. Thus, in line with studies reporting similar differences (Gustafsson et al., 2005; Osafune et al., 2008; Wu et al., system was used to engineer an ES cell line which allowed the inventors to screen for small organic molecules enhancing neuronal differentiation. One of them, phenazopyridine, was further analyzed in human ES cells. Phenazopyridine: i) enhanced neuronal differentiation, ii) increased cell survival, iii) decreased the amount of non-neuronal and undifferentiated cells, and iv) synchronized the cellular differentiation state. Phenazopyridine allowed the development of a differentiation protocol compatible with the generation of clinical grade neural precursors, which were able differentiate into different neuronal subtypes, astrocytes and oligodendrocytes. In summary, a very useful approach for identifying small molecules directing stem cell differentiation is described below. This led to the establishment of a new application for an old drug and the development of a novel clinical grade protocol for neuronal differentiation of ES cells.

Methods

Reagents. Reagents and their sources were as follows: the pDONR221 vector (Invitrogen corp.); the pGEM®-T Easy plasmid, the pRL-CMV Vector (Promega corp.) (Campbell et al., 2002). The pENTR eGFP, pENTR mRFP1, pENTR EF1-αS, pENTR Tα1 α-tubulin, 2K7$_{bsd}$, have been described before (Suter et al., 2006). The murine CGR8 ES cell line (European Collection of Cell Culture); the human H1 ES cell line (Wicell Research Institute Inc.); the human HS401 ES cell line (kindly provided by Outi Hovatta, Karolinska Institute); the bone marrow stromal MS5 cell line (kindly provided by Itoh et al., 1989); cell culture media, fetal bovine serum, serum replacement, penicillin, streptomycin, N2 supplement, non-essential amino acids, sodium pyruvate, collagenase IV (Gibco, Paisley, Scotland); basic human fibroblast growth factor (Invitrogen corp.); recombinant brain derived neurotrophic factor (Sigma-Aldrich); Gateway® clonase enzymes (Invitrogen corp.); Dual-Luciferase° Reporter Assay System (Promega); L-Polyornithine, human laminin (Sigma-Aldrich). Antibodies and dilutions were as follows: mouse anti-CNPase II (1:1000), rabbit anti-Musashi (1:500), rabbit anti-nestin (1:500), mouse anti-Vglut-1 (1:1000), mouse anti-GAD67 (1:2000), mouse anti-vimentin (1:200), rabbit anti-Sox1 (1:100), rabbit anti-tyrosine hydroxylase (1:1000) (Chemicon), mouse anti-Pax6 (1:50) (Developmental studies Hybridoma bank), rabbit anti-glial fibrillary acidic protein (GFAP) (1:1000) (Dako), mouse anti-βIII-tubulin (1:1000) (Sigma), rabbit anti-βIII-tubulin (1:3000) (Covance). The following fluorochrome-labeled secondary antibodies were used: AlexaFluor (555, 488 or 350)-labelled antibodies from goat or donkey against mouse, goat or rabbit (Invitrogen-Molecular probes). Small organic molecules: NINDS custom collection II, phenazopyridine hydrochloride, (Microsource Discovery inc.).

Vector constructs. The construction of the 2K7$_{GFP}$ has been described (Suter et al., 2007). To generate the 2K7$_{EFSGFP}$, the SV40 promoter sequence was replaced by the EF1-αS promoter sequence. To generate the $^2$K7$_{EFSRluc}$, the GFP coding sequence from 2K7$_{EFSGFP}$ was replaced by the Renilla luciferase coding sequence from pRL-CMV. The construction of pENTR mRFP1, pENTR Tα1 α-tubulin and pENTR Fluc were described before; Suter et al., 2007). The resulting entry vectors were then recombined into 2K7$_{EFSGFP}$ or 2K7$_{EFSRluc}$ lentivectors using the Gateway® LR plus clonase enzyme mix.

Cell cultures and neuronal differentiation. CGR8 mouse ES cells and H1 human ES cells were cultured as described (Suter et al., 2006), and human HS401 ES cells were cultured on irradiated human foreskin fibroblasts. For the primary screening assay, CGR8 cells were seeded in 96-well plates at 10$^3$ cells per well in differentiation medium (BHK-21 medium supplemented with 20% fetal calf serum, L-glutamine, non-essential amino acids, sodium pyruvate, penicillin and streptomycin). 48 hours later, medium was removed and replaced by 330 µl of fresh differentiation medium. 1 µl of the drug library diluted in DMSO at 3.3 mM was added to each well to obtain a final drug concentration of 10 µM. 72 hours later, cells were assayed for Firefly and Renilla luciferase activity.

To perform the secondary screening assay, neuronal differentiation of CGR8 cells was carried out in SR medium (DMEM high glucose supplemented with 15% KO serum (Gibco), non-essential amino acids, penicillin and streptomycin). Cells were plated at 10$^5$ cells per 10 cm cell culture dish and maintained is SR medium for 5 days with compounds found in the primary screen. Cells were subsequently dissociated and replated at 4×10$^4$ cells/cm$^2$ in N2 medium (DMEM high glucose, N2 supplement, 10 ng/ml basic fibroblast growth factor, penicillin and streptomycin) and cultured for four additional days without compound addition.

Two different protocols were used to induce neuronal differentiation of human ES cells. In the first protocol, human ES cells were mechanically dissociated into small aggregates and plated on laminin/polyornithine coated six-well plates. Cells were cultured 2 weeks in human SR medium (DMEM F-12 supplemented with 15% knockout serum (Gibco), non-essential amino acids, penicillin and streptomycin), followed by 4 weeks in N2 medium. Compounds were added throughout these first 6 weeks. Subsequently, cells were mechanically dissociated and replated on polyornithine/laminin-coated 6 well plates. Throughout the text, this first differentiation protocol will be referred to as "differentiation protocol 1". The second differentiation protocol was derived from previously described differentiation conditions (Nat et al., 2007). In the second differentiation protocol, undifferentiated human ES cells were mechanically dissociated into small aggregates and cultured in suspension on low-attachment six-well plates. For the first 4 days, they were cultured in neuronal induction medium (DMEM F-12, N2 supplement, penicillin and streptomycin), which was changed to simple neuronal proliferation medium (DMEM F-12, N2 supplement, 20 ng/ml bFGF, penicillin and streptomycin) for 2 additional days. Subsequently, aggregates were plated on polyornithine/laminin-coated six-well plates and maintained in simple neuronal proliferation medium for 7 days. Cells were then mechanically dissociated and replated in N2 medium at a density of 2×10$^4$ cells per cm$^2$ for two additional weeks. Compounds were added throughout these first 4 weeks. Cells were then replated at a density of 5'000 cells per cm$^2$ in neuronal differentiation medium (Neurobasal medium, B-27 supplement, BDNF (10 ng/ml), penicillin and streptomycin). Throughout the text, this second differentiation protocol will be referred as to "differentiation protocol 2".

For three-dimensional neuronal differentiation, 5-10 spheres were generated as described in differentiation protocol 2 and plated on a pre-cut patch of hydrophilic polytetrafluoroethylene (PTFE) membrane (confetti, 6 mm diameter, 0.4 µm, BioCell-Interface, La Chaux-de-Fonds, Switzerland). Next, the membrane was placed in a Millicell®-CM (0.4 µm) Culture Plate Insert (Millipore) on one ml of N2 medium. The medium was changed every 2-3 days. This method has been described for tissue slices previously (Stoppini et al., 1991) and has been recently adapted to ES cell-derived neural tissue by Preynat-Seauve et al. (attached manuscript).

ES cell transductions. ES cell transductions were performed as previously described (Suter et al., 2006). To generate the CGR8$_{EFSGFP}$Tα1mRFP1 cell line, ES cells were transduced with the 2K7$_{EFSGFP}$Tα1mRFP1 lentivector and eGFP-positive cells were subsequently sorted by flow cytometry. To generate the CGR8$_{EFSRluc}$Tα1Fluc cell line, ES cells were transduced with the 2K7$_{EFSRluc}$Tα1Fluc lentivector and subsequently grown as clones in 96-well plates. Four weeks later, cells were assayed for Renilla luciferase activity. Several clones were found to be positive and the clone with the highest activity was chosen to perform the primary screen.

Dual Luciferase assays. CGR8ES cells were lyzed in 96-well plates according to the manufacturer's instructions. Luminescence measurements were performed on a Fluostar Optima (BMG Labtech GmbH, Hanns-Martin-Schleyer-Str. 10, D-77656 Offenburg/Germany).

Immunofluorescence microscopy. Immunofluorescence was carried out according to standard techniques. Briefly, mouse ES cells were grown on polyornithine-coated glass coverslips in six-well plates, and human ES cells were grown on plastic or glass coverslips coated with laminin/polyornithine in six-well plates. Cells were fixed with 2% paraformaldehyde for 30 min, washed with HBSS and permeabilized with 0.5% (v/v) Triton X-100 for 30 min. Cells were then exposed to primary antibodies overnight at 4° C. After two washes in HBSS containing 1% FBS (blocking buffer), cells were stained with secondary antibodies at RT for 1 h (1:1000 dilution in blocking buffer). Cell nuclei were stained with 1 µg/ml 4'-6-Diamidino-2-phenylindole (DAPI) for 10 min. Pictures were taken on an ImageXpress Micro (Molecular Devices) or a Zeiss axioplan microscope equipped for epifluorescence.

Immunostaining quantification. Immunostaining and nuclear staining quantifications were performed using the MetaXpress software (Molecular devices). Total neurite outgrowth was quantified using the neurite outgrowth analysis module, and total cell numbers were quantified with the count nuclei analysis module.

Quantitative analysis of cells expressing fluorescent proteins. For the studies investigating the activity of the Tα1 α-tubulin and the EF1-αS promoter during neuronal differentiation of the CGR8$_{EFSGFP}$Tα1mRFP1 cell line, fluorescence intensity of eGFP and mRFP1 in a given cell was quantified using the Metamorph® software.

Real Time PCR. Reactions were run on an ABI Prism 7900 HT detection system (Applied Biosystems). ALAS and GusB were used as housekeeping genes. As these genes behaved similarly in all samples examined, data was normalized to ALAS level. Sequences of the primers are shown in supplementary table.

Results

Primary screening of neuronal differentiation of ES cells. A method was first developed to screen for small molecules that affect neural lineage commitment of ES cells. For this purpose, the 2K7 lentivectors (Suter et al., 2006) were used to generate dual reporter mouse ES cell lines. A cell line in which GFP is expressed under the control of the ubiquitous EF1-α short promoter and mRFP1 under the control of the neuron-specific Tα1 α-tubulin promoter was generated (FIG. 6A). To validate this cell line, it was differentiated towards neurons using an established protocol based on coculture with the MS5 stromal cell line (Barberi et al., 2003), and monitored changes of fluorescence in cells undergoing neuronal differentiation. Immunofluorescence was analyzed in the cells on day 5 and investigated the correlation between the red/green fluorescence ratio and the staining for β3-tubulin, revealed by a blue secondary antibody (FIG. 6B). The red/green fluorescence ratio in undifferentiated cells was quantified as well as in β3-tubulin-negative and positive cells during neuronal differentiation (FIG. 6C). The correlation between the red/green ratio and β3-tubulin staining was good, allowing the inventors to monitor neuronal differentiation of ES cells. The use of fluorescent proteins allowed to verify the general validity of this approach. However, the inventors hypothesized that the use of luminescent reporter genes could enhance the sensitivity of the system. A second lentivector was therefore constructed using luminescence rather than fluorescence reporters. For this purpose, the above-described vector was modified by replacing mRFP1 with firefly luciferase (Fluc) and GFP by renilla luciferase (Rluc) (FIG. 6D), and generated a cell line carrying this construct (see materials and methods). To validate this cell line, cells were cultured either on MS5 stromal cells to induce neuronal differentiation, or on mouse embryonic fibroblasts (MEF) which do not induce neuronal differentiation. A time-course experiment was performed in both conditions, and observed an up to 46-fold increase of Fluc/Rluc when ES cells were cultured on MS5 but not when cultured on MEF (FIG. 6E). Therefore, this cell line was used to perform the primary screening assay. It will be referred to as to CGR8$_{dual\ luc}$ throughout the text.

Next, CGR8$_{dual\ luc}$ was used to screen a small molecule library containing compounds approved by the food and drug administration (FDA). The advantages of such a library include the fact that the compounds are proven to be bioactive and may readily be used under clinical grade conditions. 1040 compounds were screened, among which 975 compounds gave analyzable results and 65 compounds resulted in the absence of any luciferase signal, probably due to cellular toxicity. FIG. 1F shows values of the Fluc/Rluc ratio for 975 compounds, normalized to the mean Fluc/Rluc ratio found in control-treated cells.

For further studies, 32 compounds were selected with high Fluc/Rluc ratio. A dose-response analysis of Fluc/Rluc ratio was performed in the same conditions as used for the primary screen, using concentrations ranging from 100 nM to 100 µM. For each compound whose activity was confirmed, the best concentration was selected to further investigate its activity in a neuronal differentiation protocol of mouse ES cells (see Methods above). The amounts of neurons were quantified by calculating total neurite outgrowth identified by β3-tubulin immunoreactivity using an automated imaging system (see Methods above). One compound, phenazopyridine, resulted in an increase of total neurite outgrowth as compared to control cells and its activity was further investigated on human ES cell differentiation.

Phenazopyridine enhances neuronal differentiation of human ES cells. The effects of phenazopyridine on neuronal differentiation of H1 ES cells was investigated in a system with relatively low basal neuronal differentiation ("differentiation protocol 1", described in material and methods). Human ES cells were treated either with DMSO alone or phenazopyridine for the first 6 weeks of differentiation, and cells were subsequently immunostained for neuronal markers at different time points. After 8 weeks of differentiation, the DMSO-treated cell population was highly heterogeneous as assessed by immunostaining for β3-tubulin, nestin, vimentin and GFAP. In contrast, phenazopyridine-treated cells were more homogeneous, most cells being positive for nestin, β3-tubulin, and vimentin, with occasional neuronal networks. After 10 weeks, further neuronal networks formed in phenazopyridine-treated cells, but not in DMSO-treated cells. To quantify neuronal differentiation, the inventors chose to measure total neurite outgrowth and divided it by total cell number at different time points in three independent experiments (FIG. 7A). Efficiency of differentiation of phenazopyridine-treated cells into mature neurons was variable, but always superior to DMSO-treated cells, as confirmed by Kruskal-Wallis analysis of ranks statistical analysis (p=0.045).

Next, the activity of phenazopyridine was tested on neuronal differentiation in a three-dimensional culture system. At two different time points (FIG. 7B), the inventors observed a significant increase in the total number of neural tubes when phenazopyridine was added to the culture medium. These results demonstrate that phenazopyridine can enhance neuronal differentiation of human ES cells.

Phenazopyridine permits the generation of homogeneous and synchronous populations of neuronal precursors. The effects of phenazopyridine (3 µM) was investigated using a differentiation protocol in which all components can be replaced by clinical grade equivalents (differentiation protocol 2, described in materials and methods). Phase contrast pictures of human ES cells were taken at different stages of differentiation. DMSO-treated and phenazopyridine-treated spheres were morphologically indistinct after one week of differentiation. At two weeks of differentiation, control spheres remained relatively compact, whereas phenazopyridine-treated spheres developed bigger areas of monolayer at their periphery. Interestingly, many mitotic figures and PCNA-positive cells could be found in this area of phenazopyridine-treated cells, whereas only very few were present in DMSO-treated cells. After mechanical passaging, cells remained as aggregates in DMSO-treated cells while phenazopyridine-treated cells could easily be dissociated into single cells. These observations were also confirmed in the HS401 cell line. Interestingly, there was a marked difference between the percentages of living single cells in control cells compared to phenazopyridine-treated cells as assessed by trypan blue staining at different time-points throughout the procedure. This suggests that phenazopyridine favours cell growth in monolayers and promotes survival of dissociated cells.

To investigate the phenotype of control and phenazopyridine-treated cells, immunostainings were performed for several neuronal markers after four weeks of differentiation in three independent experiments. Control-treated cells were mainly present as clusters, which were often containing typical rosette areas positive for nestin and β3-tubulin, but there were also clusters negative for both markers. Musashi, Pax6, Sox1, vimentin and GFAP were distributed heterogeneously. In contrast, phenazopyridine-treated cells were mainly present as isolated cells, with only very few small clusters. Virtually all cells were nestin, Sox 1 and vimentin-positive, expressed β3-tubulin and Pax6 at low levels, and were negative for musashi. Cells therefore displayed a homogeneous distribution of neuronal markers, at the exception of few strongly β3-tubulin-positive, and some GFAP-positive cells. To quantify the synchronization of the cell population induced by phenazopyridine, the number of cells negative for nestin and β3-tubulin (non-neural cells), positive for nestin with low levels of β3-tubulin (early neuronal precursors), positive for both markers at high levels (young neurons), or expressing β3-tubulin only (differentiated neurons) were counted (FIGS. 8A and 8B). In DMSO-treated cells, all expression patterns were well represented (FIG. 8A), reflecting a highly heterogeneous cell population. In contrast, approximately 98% of phenazopyridine-treated cells were nestin-positive with low levels of β3-tubulin, and no non-neural cells or differentiated neurons were observed. In conclusion, phenazopyridine treatment resulted in the generation of a homogeneous neuronal precursor cell population.

Phenazopyridine accelerates emergence of early neuronal markers and decreases markers of undifferentiated and non-neural cells. The kinetics of emergence of neural and non-neural markers in DMSO and 3 µM phenazopyridine-treated H1 ES cells were evaluated using real time PCR. After 2 weeks of differentiation, the inventors observed an upregulation of markers of early neuronal differentiation (Pax6, nestin), intermediate (β3-tubulin, vimentin) and late differentiation (β3-tubulin, Map2) in phenazopyridine-treated cells as compared to control cells (FIG. 9A). Markers for forebrain (Mash1), ventral hindbrain (Nkx2.2, HoxB4, Olig2), were also upregulated, whereas Pax7 (marking the dorsal neural tube) and Pax2 (marking midbrain) were similar to control-treated cells. However, significant differences in the expression of the same markers at 4 weeks of differentiation were not observed; the latter observation fits well with the observed induction of synchronized differentiation by phenazopyridine (FIG. 4). Expression of non-neural markers was next evaluated. Unexpectedly, after 2 weeks of differentiation, Oct-4 (marking undifferentiated ES cells) and brachyury (marking early mesoderm) were increased in phenazopyridine-treated cells, and α-fetoprotein (AFP, marking primitive endoderm) did not vary between both conditions (FIG. 9B). The inventors reasoned that the persistence of these markers could be temporary and therefore investigated their expression after four weeks of differentiation. Indeed, all three markers were markedly downregulated in phenazopyridine-treated cells (>1000 fold for Oct4 and α-fetoprotein, and >10 fold for brachyury; FIG. 9C). These results suggest that i) phenazopyridine accelerates the emergence of neural markers and that ii) 4 weeks of treatment with phenazopyridine decreases the amount of undifferentiated and non-neural cells.

Phenazopyridine-treated cells can differentiate into all three neural lineages. To investigate the potential of neuronal precursors generated through phenazopyridine treatment, the inventors devised a two step differentiation protocol. Cells were first treated with 3 µM phenazopyridine for 4 weeks and subsequently replated in the absence of phenazopyridine. For the second step, the inventors cultured cells at low density ($5 \times 10^3$ cells/cm$^2$) on polyornithine/laminin-coated support in neuronal differentiation medium and investigated their phenotype at different time points in three independent experiments. The inventors analyzed several markers of neuronal differentiation as well as alkaline phosphatase, which is considered to be one of the best markers of undifferentiated ES cells (O'Connor et al., 2008). In control-treated cells after one week of differentiation, the inventors observed a heterogeneous cell population: neuronal networks in some regions juxtaposed to areas containing tightly packed neuronal precursors, and very few isolated cells positive for Sox1 and occasionally for Pax6. After 4 weeks of differentiation, control-treated cells still contained cells at variable stages of differentiation. Well-developed neuronal networks, alkaline phosphatase-positive cell areas, and Sox1 and Pax6-positive neuronal precursors coexisted in the same culture. In contrast, after one week, the phenazopyridine-treated cells developed into a relatively homogenous monolayer of neural precursors and early neurons with short neurites. The inventors analyzed subtypes of neurons in the phenazopyridine-treated cells and observed glutamatergic, GABAergic and—more rarely—TH-positive neurons. The inventors did not observe the presence of astrocytes or oligodendrocytes precursors, as assessed by GFAP and CNPase immunostaining, respectively. After 4 weeks, the inventors also observed slow-growing cell clusters homogeneously positive for nestin, β3-tubulin, Sox1 and vimentin, together with more mature neurons, astrocytes and oligodendrocyte progenitors. The majority of cells were belonging to the neuronal lineage. However, the proportion of the different cell types was variable. Importantly, in phenazopyridine-treated cells, the inventors never detected alkaline phosphatase-positive cells.

Discussion

In this example, a dual reporter screening approach was used to discover small molecules modulating ES cell differentiation. The screening of a FDA-approved drug library allowed the inventors to discover the neurogenic potential of phenazopyridine. This molecule not only enhanced and synchronized neuronal differentiation of ES cells, but also decreased the amount of non-neuronal and undifferentiated cells. Phenazopyridine was utilized in the development of a novel differentiation protocol of human ES cells using only media formulations which are compatible with clinical grade.

Over the past years, small organic molecules have been of increasing interest in stem cell biology as tools to direct cell fate (Ding et al., 2003; Chen et al., 2004; Chen et al., 2006a; Sachinidis et al., 2006; Chen et al., 2007; Chen et al., 2006b; Desbordes et al., 2008). So far, such approaches have been applied to mouse ES cells and molecules which maintain cells in an undifferentiated state (Chen et al., 2006a; Desbordes et al., 2008) or enhance their differentiation (Ding et al., 2003; Sachinidis et al., 2006; Desbordes et al., 2008) have been described. One study demonstrated that the GSK3β inhibitor TWS119 enhanced neuronal differentiation of mouse ES cells (Ding et al., 2003). Based on experiments by the inventors, TWS119 was not observed to be applicable to human ES cells (decreased cell growth and only small effect on neuronal differentiation). In this study a collection of FDA-approved compounds were screened. The advantages of using compounds derived from such a collection include their proven bioactivity, low toxicity, and compatibility with future clinical applications. A key aspect of this screening method is the use of a double promoter/reporter system that allows ratio measurements. In contrast to studies using single promoter-reporter modules (Ding et al., 2003; Sachinidis et al., 2006), this system allows the activity of the neuronal promoter to be normalized and therefore allows the extent of neuronal differentiation and the size of the cell population analyzed to be discriminated. The use of the 2K7 lentivector system (Suter et al., 2006) was instrumental for the construction of the cell lines, as it can carry two independent expression modules. It therefore allows the same copy numbers of the neuronal and the ubiquitously expressed reporter to be obtained. As demonstrated by the results, this leads to a reliable and sensitive primary screen. It is anticipated that this approach may be more widely used in ES cell research.

The inventors used mouse rather than human ES cells for the primary screen and confirmed the results subsequently in human ES cells. The choice of mouse ES cells for the primary screen was dictated by the long time required for human ES cell differentiation. Even if occasionally compounds active in the mouse system might not work in human cells (TWS119, see above), the striking effects of phenazopyridine in human ES cells validates the approach. Phenazopyridine is an old molecule which has been widely used for symptomatic pain relief caused by irritation of the lower urinary tract mucosa (Gaines, 2004). In the U.S., it is still available as an over-the-counter drug, however the molecular mechanism of action of this common drug remains to date unknown. The molecular structure of phenazopyridine can provide some hints about its possible targets. First, it shares important structural similarities with some non-Competitive metabotropic glutamate receptor 5 (mGluR5) antagonists such as SIB-1757 and SIB-1893. It was recently reported that treatment of mouse ES cells with the non-Competitive mGluR5 antagonist MPEP enhances their differentiation towards neurons (Sarichelou et al., 2008). It remains to be seen whether phenazopyridine acts through this pathway.

One of the striking properties of phenazopyridine is its capacity to synchronize ES cell differentiation. These results suggest that phenazopyridine provides a powerful exogenous cue that might be involved in this synchronization. However, the fact that in the presence of phenazopyridine, differentiating ES cells are capable of growing as a monolayer rather than as self-organizing cell clusters with hierarchical internal organization might also participate in this effect. The ability to obtain homogenous cell populations is of fundamental importance both for the study of defined differentiation stages in vitro and for cell therapy applications. One study proposed a cell sorting approach to allow synchronous neuronal precursor populations to be obtained (Pruszak et al., 2007). However, such strategies remain tedious. Here the inventors show that the simple addition of phenazopyridine to the differentiation medium resulted in the synchronization of cell differentiation, generating a homogenous population of neuronal progenitors virtually devoid of non neural cells. Thus, this method is an important step towards the engineering of high quality human neuronal cell populations derived from ES cells.

Classical tools for ES cell differentiation include growth factors, matrix proteins and, coculture with stromal cells. The results shown here provide strong evidence that small organic molecules should be added to this list. The chemical space is of enormous size and it is likely that for many biological processes, small molecular agonists or antagonists exist. So far, the efficient use of the chemical variety in stem cell research was limited because of low throughput procedures. Thus, innovative assays allowing to search chemical libraries for active substances are key to take advantage of this promising interface between the chemical and the biological world. These studies provide both a useful assay and identifies a compound that directs the cell fate of differentiating ES cells.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 5,843,780
U.S. Pat. No. 6,200,806
U.S. Pat. No. 6,833,269
U.S. Pat. No. 6,833,269
U.S. Pat. No. 7,029,913
U.S. Patent Application 2008/0233610
European Patent Application EP1970446A1
*A practical approach* (Robertson, Ed.), IRL Press Ltd. 1987.
Allegrucci and Young, *Hum. Reprod. Update*, 13:103-120, 2007.
Amit et al., *Dev. Bio.*, 227:271-278, 2000.
*Animal Cell Culture* (Freshney, Ed., 1987)
Anthony et al., *Neuron.*, 41:881-890, 2004.
Barberi et al., *Nat. Biotechnol.*, 21(10):1200-1207, 2003.
Bauer and Patterson, *J. Neurosci.*, 26(46):12089-12099, 2006.
Bayatti et al., *Cereb. Cortex*, 18(7):1536-1548, 2007.
Byrne et al., *Nature*, 450(7169):497-502, 2007.
Campbell et al., *Proc. Natl. Acad. Sci. USA*, 99(12):7877-7882, 2002.
Chalfie et al., *Science*, 263(5148):802-805, 1994.
Chen et al., *J. Am. Chem. Soc.*, 126(2):410-411, 2004.
Chen et al., *Mol. Biosyst.*, 2(1):18-24, 2006b.
Chen et al., *Proc. Natl. Acad. Sci. USA*, 103(46):17266-17271, 2006a.
Chen et al., *Proc. Natl. Acad. Sci. USA*, 104(25):10482-10487, 2007.
Cho et al., *Proc. Natl. Acad. Sci. USA*, 105:3392-3397, 2008.
*Current Protocols in Molecular Biology and Short Protocols in Molecular Biology*, 3rd Edition (Ausubel et al., Eds.), 1987 & 1995.
Desbordes et al., *Cell Stem Cell*, 2(6):602-612, 2008.

Ding et al., *Proc. Natl. Acad. Sci. USA,* 100(13):7632-76337, 2003.
Doetsch et al., *Cell,* 97:703-716, 1999.
Eiraku et al. *Cell Stem Cell.* 3(5):519-32, 2008.
Elkabetz et al., *Genes Dev.,* 22:152-165, 2008.
Fallon et al., *Proc. Natl. Acad. Sci. USA,* 97(26):14686-14691, 2000.
Feng et al., *Neuron.,* 12:895-908, 1994.
Foti et al., *J. Cell Biol.,* 139:37-47, 1997.
Gaines, *Urol Nurs.,* 24(3):207-209, 2004.
Garcia et al., *Nat. Neurosci.,* 7:1233-1241, 2004.
*Gene Transfer Vectors for Mammalian Cells* (Miller & Calos, Eds.), 1987.
Gotz et al., *Brain Res Bull.,* 57:777-788, 2002.
Gould, *Nat. Rev. Neurosci.,* 8:481-488, 2007.
*Guide to Techniques in Mouse Development* (Wasserman et al. Eds.), Academic Press 1993.
Gustafsson et al., *Dev. Cell.,* 9:617-628, 2005.
*Handbook of Pharmaceutical Salts: Properties, Selection and Use* (Stahl & Wermuth, Eds., Verlag Helvetica Chimica Acta, 2002.
Haubensak et al., *Proc. Natl. Acad. Sci. USA,* 101:3196-3201, 2004.
Innis et al., *Proc. Natl. Acad. Sci. USA,* 85(24):9436-9440, 1988.
Itoh et al., *Exp. Hematol.,* 17(2):145-153, 1989.
Itoh et al., *Exp. Hematol.,* 17:145-153, 1989.
Itskovitz-Eldor et al., *Mol. Med.,* 6:88B95, 2000.
Joannides et al., *Stem Cells,* 25:731-737, 2007.
Joannides et al., *Brain,* 130:1263-1275, 2007.
Johansson et al., *Cell,* 96:25-340, 1999.
Kim et al., *Neurochem. Res.,* 32(8):1399-1406, 2007.
Lee et al., *Nat. Biotechnol.,* 25:1468-1475, 2007.
Lee et al., *Stem Cells,* 25:1931-1939, 2007.
Malatesta et al., *Neuron.,* 37:751-764, 2003.
Mallat et al., *Curr. Opin. Neurobiol.,* 15:101-107, 2005.
Martin, *Proc. Natl. Acad. Sci. USA,* 78:7634B7638; 1982.
Merkle and Alvarez-Buylla, *Curr. Opin. Cell Biol.,* 18:704-709, 2006.
Metallo et al., *Stem Cells,* 2007 (Epub ahead of print)
Mo and Zecevic, *Cereb Cortex,* 18(6):1455-1465, 2007.
Nat et al., *Glia.,* 55(4):385-399, 2007.
O'Connor et al., *Stem Cells,* 26(5):1109-1116, 2008.
Osafune et al., *Nat. Biotechnol.,* 26:313-315, 2008.
Perrier et al., *Proc. Natl. Acad. Sci. USA,* 101:12543-12548, 2004.
Perrier et al, *Proc. Natl. Acad. Sci. USA,* 101(34):12543-12125, 2004.
Pruszak et al., *Stem Cells,* 25(9):2257-2268, 2007.
Quinones-Hinojosa et al., *J. Comp. Neurol.,* 494:415-434, 2006.
Rathjen et al., *Reprod. Fertil. Dev.,* 10:31, 1998.
Remington's Pharmaceutical Sciences" 15th Edition, pages 1035-1038 and 1570-1580
Reubinoff et al, *Nature Biotech.,* 18:399, 2000.
Reubinoff et al., *Nat. Biotechnol.,* 18:399B404, 2000.
Rezaie et al., *Microsc. Res. Tech.,* 45:359-382, 1999.
Rietze and Reynolds, *Methods Enzymol.,* 419:3-23, 2006.
Roach et al., *Eur. Urol.,* 23:82B87, 1993.
Roussa and Krieglstein, *Cell Tissue Res.,* 318:23-33, 2004.
Sachinidis et al., *Cell Physiol. Biochem.,* 18(6):303-314, 2006.
Sarichelou et al., *Cell Death Differ.,* 15(4):700-707, 2008.
Schulz et al., *Stem Cells,* 22:1218-1238, 2004.
Smith, In: *Origins and Properties of Mouse Embryonic Stem Cells, Annu Rev. Cell. Dev. Biol.,* 2000.
Sonntag et al., *Stem Cells,* 25:411-418, 2007.
Stern, *Development,* 132:2007-2021, 2005.
Stoppini et al., *J. Neurosci. Methods,* 37(2):173-182, 1991.
Storch et al., *Exp. Neurol.,* 170:317-325, 2001.
Studer et al., *J. Neurosci.,* 20:7377-7383, 2000.
Suter et al., *J Stem Cells.* January, 63-72, 2007.
Suter et al., *Stem Cells,* 24(3):615-623, 2006.
Svendsen et al., *Brain Pathol.,* 9(3):499-513, 1999.
Takahashi and Yamanaka, *Cell,* 126:663-676, 2006.
Takahashi et al., *Cell,* 126(4):663-676, 2006.
Takahashi et al., *Cell,* 126(4):663-76, 2007.
Takahashi et al., *Cell,* 131:861-872, 2007.
Thiebaud et al., *IEEE Trans. Biomed. Eng.,* 44:1159-1163, 1997.
Thomson and Marshall, *Curr. Top. Dev. Biol.,* 38:133-165, 1998.
Thomson and Odorico, *J. Trends. Biotechnol.,* 18:53B57, 2000.
Thomson et al. *Proc. Natl. Acad. Scie. USA,* 92:7844-7848, 1995.
Thomson et al., *Science,* 282:1145, 1998.
van Vliet et al., *Neurotoxicology,* 28:1136-1146, 2007.
Vazin et al., *Stem Cells,* 26:1517-1525, 2008.
Wiles, *Meth. Enzymol.,* 225:900, 1993.
Wilson and Edlund, *Nat. Neurosci.,* 4(Suppl):1161-1168, 2001.
Wu et al., *Proc. Natl. Acad. Sci. USA,* 104:13821-13826, 2007.
Xu et al., *Nat. Biotechnol.,* 19:971-974, 2001.
Yan et al., *Stem Cells,* 23:781-790, 2005.
Yang et al., *Stem Cells,* 26:55-63, 2008.
Ying et al., *Cell,* 115:281-292, 2003.
Yu and Thompson, *Genes Dev.* 22(15):1987-97, 2008.
Yu et al., *Science,* 318:1917-1920, 2007.

The invention claimed is:

1. A method of preparing one or more neuronal cells in vitro, comprising:
   a) exposing substantially or essentially undifferentiated mammalian pluripotent or neural stem cells to an effective amount of a differentiation agent under conditions sufficient to enhance differentiation of the stem cells to neural precursor cells as compared to differentiation under similar conditions without the differentiation agent; and
   b) incubating the neural precursor cells in the absence of the differentiation agent under conditions sufficient to differentiate the neural precursor cells into neurons, astrocytes or oligodendrocytes;
   wherein the differentiation agent is a pyridine derivative having the following structure:

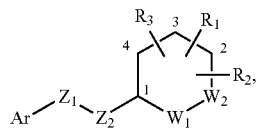

wherein:
   the six membered ring defined by $W_1$, $W_2$ and carbon atoms 1, 2, 3 and 4, may be aromatic or non-aromatic, and further wherein any two neighboring atoms of this six membered ring may be singly or doubly bonded to one another;
   $Z_1$ and $Z_2$ are either carbon or nitrogen, further wherein $Z_1$ and $Z_2$ may be singly, doubly, or triply bonded to one another and wherein $Z_2$ and carbon atom 1 may be singly or doubly bonded to one another, provided that the bond between $Z_1$ and $Z_2$ is not triple when $Z_1$ and $Z_2$ are nitrogen, further provided that the bond between $Z_1$ and $Z_2$ is single when the bond between $Z_2$ and carbon atom 1 is double;

Ar is a heteroatom-substituted or heteroatom-unsubstituted aryl$_{(C1-C12)}$;

one of either $W_1$ and $W_2$ is nitrogen and the other is carbon;

$R_1$, $R_2$, and $R_3$ are independently hydrogen, hydroxy, amino, cyano, halo, nitro, mercapto, or a heteroatom-substituted or heteroatom-unsubstituted alkyl$_{(C1-C8)}$, aryl$_{(C1-C8)}$, aralkyl$_{(C2-C8)}$, acyl$_{(C1-C8)}$, alkoxy$_{(C1-C8)}$, alkylamino$_{(C1-C8)}$, or =O;

or pharmaceutically acceptable salts, hydrates, tautomers, acetals, ketals, hemiacetals, hemiketals, or optical isomers thereof.

2. The method of claim 1, wherein $Z_1$ and $Z_2$ are both carbon triply bonded to each other.

3. The method of claim 1, wherein $Z_1$ and $Z_2$ are both nitrogen doubly bonded to each other.

4. The method of claim 1, wherein the differentiation agent is:

phenazopyridine; SIB 1893; SIB 1757; 2-methyl-6-(phenylethynyl)-pyridine (MPEP); NSC41777; 6-methyl-3-phenyldiazenylpyridin-2-amine; 2,6-Diamino-3-(4-iodophenylazo)pyridine (U.S. Pat. No.7,660,000); phenyldiazenylpyridin-2-amine ; 3-(4-chlorophenyl) diazenylpyridine-2,6-diamine; 3-(2-chlorophenyl) diazenylpyridine-2,6-diamine; 3-[(2-methyl-1,3-thiazol-4-yl)ethynyl]pyridine (MTEP); a physiologically acceptable salt thereof; or any mixture thereof.

5. The method of claim 1, wherein the stem cells are embryonic stem (ES) cells, induced pluripotent stem (iPS) cells, or embryonic stem cells derived by somatic cell nuclear transfer.

6. The method of claim 5, wherein the stem cells are ES cells.

7. The method of claim 6, wherein the ES cells are obtained from an embryo or a blastocyst.

8. The method of claim 6, wherein the ES cells are obtained from a cell culture comprising undifferentiated ES cells.

9. The method of claim 6, wherein the ES cells are mouse cells.

10. The method of claim 6, wherein the ES cells are human cells.

11. The method of claim 6, wherein the ES cells are monkey cells.

12. The method of claim 6, wherein neural precursor cells prepared by exposure to the differentiation agent are synchronized.

13. The method of claim 6, wherein undifferentiated cells and non-neural cells are eliminated by exposure to the differentiation agent.

14. The method of claim 1, wherein the stem cells are adult or embryonic neural stem cells.

15. The method of claim 1, wherein the stem cells are mouse, human or primate stem cells.

16. The method of claim 1, wherein neural precursor cells prepared by exposure to the differentiation agent are synchronized.

17. The method of claim 1, wherein undifferentiated cells and non-neural cells are eliminated by exposure to the differentiation agent.

18. The method of claim 1, wherein the pluripotent or neural stem cells are differentiated into neural precursor cells.

19. The method of claim 1, wherein the pluripotent or neural stem cells are differentiated into neurons.

\* \* \* \* \*

UNITED STATES PATENT AND TRADEMARK OFFICE
CERTIFICATE OF CORRECTION

Page 1 of 2

PATENT NO. : 8,609,413 B2
APPLICATION NO. : 12/747116
DATED : December 17, 2013
INVENTOR(S) : Suter It is certified that error appears in the above-identified patent and that said Letters Patent is hereby corrected as shown below:

In title page, item [54] and in the specification, column 1, lines 1-5, Title, delete "NEURONS, ASTROCYTES AND OLIGODENDROCYTES DIFFERENTIATED FROM A MAMMALIAN PLURIPOTENT OR NEURAL STEM CELLS EXPOSED TO A PYRIDINE DERIVATIVE" and replace with --NEURONS, ASTROCYTES AND OLIGODENDROCYTES DIFFERENTIATED FROM MAMMALIAN PLURIPOTENT OR NEURAL STEM CELLS EXPOSED TO A PYRIDINE DERIVATIVE-- therefor In title page, item [75] Inventors, delete "Habare-Lullin" and replace with --Habere-Lullin-- therefor.

In title page, item [73] Assignee, delete "Carson Clty" and replace with --Carson City-- therefor.

In title page, item [56] References Cited - Other Publications, delete the 11th reference on page 1 "Cappuccio et al., "Context-dependent regulation of embryonic stem cell differentiation by mGLu5R metabotropic glutamate receptors." Neuropharmacology, 51(3):606-611, 2006." and replace with --Cappuccio et al., "Context-dependent regulation of embryonic stem cell differentiation by mGlu5R metabotropic glutamate receptors." Neuropharmacology, 51(3):606-611, 2006.-- therefor.

In title page, item [56] References Cited - Other Publications, delete the 2nd reference on page 2 "Ding et al., "Synthetic small molecules that control stem cell fate," Proc. Natl. Acad. Sci. USA, 100 (13): 7632-76337, 2003." and replace with --Ding et al., "Synthetic small molecules that control stem cell fate," Proc. Natl. Acad. Sci. USA, 100 (13): 7632-7637, 2003.-- therefor.

In title page, item [56] References Cited - Other Publications, delete the 13th reference on page 2 "Metallo et al., "Retinoic Acid and Bone Morphogenetic Protein Signaling Synergize to Efficiently Direct Epithelial Differentiation of Human Embryonic Stem Cells," Stem Cells, 26(2):372-380." and replace with --Metallo et al., "Retinoic Acid and Bone Morphogenetic Protein Signaling Synergize to Efficiently Direct Epithelial Differentiation of Human Embryonic Stem Cells," Stem Cells, 26(2):372-380, 2008.-- therefor.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,609,413 B2

In title page, item [56] References Cited - Other Publications, delete the 15th reference on page 2 "Nat et al., "Neurogenic neuroepithetial and radial glial cells generated from six human embryonic stem cell lines in serum-free suspension and adherent cultures," Glia, 55(4):385-399, 2007." and replace with -- Nat et al., "Neurogenic neuroepithelial and radial glial cells generated from six human embryonic stem cell lines in serum-free suspension and adherent cultures," Glia, 55(4):385-399, 2007.-- therefor.

In title page, item [56] References Cited - Other Publications, delete the 18th reference on page 2 "Perrier et al., "Derivation of midbrain dopamine neurons from human embryonic stem cells," Proc. Natl. Acad. Sci. USA, 101 (34):12543-12125, 2004." and replace with --Perrier et al., "Derivation of midbrain dopamine neurons from human embryonic stem cells," Proc. Natl. Acad. Sci. USA, 101(34):12543-12548, 2004.-- therefor.

In the Claims

In Claim 4, column 63, line 26, delete "U.S. Pat. No.7,660,000" and replace with --US76600000-- therefor.

UNITED STATES PATENT AND TRADEMARK OFFICE
CERTIFICATE OF CORRECTION

PATENT NO. : 8,609,413 B2
APPLICATION NO. : 12/747116
DATED : December 17, 2013
INVENTOR(S) : David M. Suter, Olivier Preynat-Seauve and Karl-Heinz Krause It is certified that error appears in the above-identified patent and that said Letters Patent is hereby corrected as shown below:

In the Specification

In column 5, line 39; column 5, lines 66-67; column 6, line 31; column 6, lines 52-53; column 10, line 42; column 28, lines 40-41; column 29, lines 11-12; column 33, lines 23-24; column 33, line 34; and column 36, lines 23-24, delete "U.S. Pat. No. 7,660,000" and replace with --US76600000-- therefor.

Signed and Sealed this
Thirteenth Day of January, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,609,413 B2 | Page 1 of 1 |
| APPLICATION NO. | : 12/747116 | |
| DATED | : December 17, 2013 | |
| INVENTOR(S) | : David M. Suter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 607 days.

Signed and Sealed this
Twelfth Day of May, 2015

Michelle K. Lee
*Director of the United States Patent and Trademark Office*